United States Patent [19]
Jørgensen

[11] Patent Number: 5,882,888
[45] Date of Patent: Mar. 16, 1999

[54] DNA INTEGRATION BY TRANSPOSITION

[75] Inventor: Steen Troels Jørgensen, Allerød, Denmark

[73] Assignee: Novo Nordisk A/S, Bagsvaerd, Denmark

[21] Appl. No.: 875,154

[22] PCT Filed: Jan. 23, 1996

[86] PCT No.: PCT/DK96/00038

§ 371 Date: Jul. 17, 1997

§ 102(e) Date: Jul. 17, 1997

[87] PCT Pub. No.: WO96/23073

PCT Pub. Date: Aug. 1, 1996

[30] Foreign Application Priority Data

Jan. 23, 1995 [DK] Denmark .................................. 0083/95
Jul. 6, 1995 [DK] Denmark .................................. 0799/95

[51] Int. Cl.$^6$ .............................. C12P 21/00; C12N 1/21; C12N 15/70; C07H 21/04
[52] U.S. Cl. ........................ 435/69.1; 435/91.4; 435/243; 435/252.31; 435/320.1; 435/172.3; 536/23.1; 536/24.2
[58] Field of Search ................................ 435/69.1, 91.41, 435/172.3, 243, 320.1, 252.31; 536/23.1, 24.2

[56] References Cited

U.S. PATENT DOCUMENTS 5,102,797 4/1992 Tucker et al. ........................ 435/172.3
5,527,695 6/1996 Hodges et al. ....................... 435/172.3

FOREIGN PATENT DOCUMENTS

WO 95/02058 1/1995 WIPO .

OTHER PUBLICATIONS

Kristensen et al. Site–specific deletion of chromosomally ligated DNA segments with the multimer resolution system of briad–host range plasmid RP4. J. Bacteriol. Vol. 177(1):52–58, Jan. 12, 1995.

Primary Examiner—George C. Elliott
Assistant Examiner—William Sandals
Attorney, Agent, or Firm—Steve T. Zelson, Esq.; Valeta Gregg, Esq.

[57] ABSTRACT

Multicopy strains of gram-positive bacteria carrying multiple copies of a DNA sequence of interest may be constructed by use of a method involving introduction of a DNA construct comprising the DNA sequence of interest into the genome of the recipient cell by transposition and subsequent deletion of a marker gene used for selection of the cells having received the DNA construct by a resolution system. The multicopy strains are preferably free from a gene encoding an undesirable marker such as an antibiotic resistance marker.

6 Claims, 31 Drawing Sheets

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
    ( A ) LENGTH: 10216 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "pMOL553"

( x i ) SEQUENCE DESCRIPTION: SEQ ID NO: 1:

```
TTCTCATGTT  TGACAGCTTA  TCATCGACTG  CACGGTGCAC  CAATGCTTCT  GGCGTCAGGC    60

AGCCATCGGA  AGCTGTGGTA  TGGCTGTGCA  GGTCGTAAAT  CACTGCATAA  TTCGTGTCGC   120

TCAAGGCGCA  CTCCCGTTCT  GGATAATGTT  TTTTGCGCCG  ACATCATAAC  GGTTCTGGCA   180

AATATTCTGA  AATGAGCTGT  TGACAATTAA  TCATCGGCTC  GTATAATGTG  TGGAATTGTG   240

AGCGGATAAC  AATTTCACAC  AGGAAACAGG  ATCAAATGGT  TTCGAATTCA  TTAAAGAGGA   300

GAAATTAACT  ATGTGCGAAC  TCGATATTTT  ACACGACTCT  CTTTACCAAT  TCTGCCCCGA   360

ATTACACTTA  AAACGACTCA  ACAGCTTAAC  GTTGGCTTGC  CACGCATTAC  TTGACTGTAA   420

AACTCTCACT  CTTACCGAAC  TTGGCCGTAA  CCTGCCAACC  AAAGCGAGAA  CAAAACATAA   480

CATCAAACGA  ATCGACCGAT  TGTTAGGTAA  TCGTCACCTC  CACAAAGAGC  GACTCGCTGT   540

ATACCGTTGG  CATGCTAGCT  TTATCTGTTC  GCGCAATACG  ATGCCCATTG  TACTTGTTGA   600

CTGGTCTGAT  ATTCGTGAGC  AAAAACGACT  TATGGTATTG  CGAGCTTCAG  TCGCACTACA   660

CGGTCGTTCT  GTTACTCTTT  ATGAGAAAGC  GTTCCCGCTT  TCAGAGCAAT  GTTCAAAGAA   720

AGCTCATGAC  CAATTTCTAG  CCGACCTTGC  GAGCATTCTA  CCGAGTAACA  CCACACCGCT   780

CATTGTCAGT  GATGCTGGCT  TTAAAGTGCC  ATGGTATAAA  TCCGTTGAGA  AGCTGGGTTG   840

GTACTGGTTA  AGTCGAGTAA  GAGGAAAAGT  ACAATATGCA  GACCTAGGAG  CGGAAAACTG   900

GAAACCTATC  AGCAACTTAC  ATGATATGTC  ATCTAGTCAC  TCAAAGACTT  TAGGCTATAA   960
```

-continued

| | | | | | | |
|---|---|---|---|---|---|---|
| GAGGCTGACT | AAAAGCAATC | CAATCTCATG | CCAAATTCTA | TTGTATAAAT | CTCGCTCTAA | 1020 |
| AGGCCGAAAA | AATCAGCGCT | CGACACGGAC | TCATTGTCAC | CACCCGTCAC | CTAAAATCTA | 1080 |
| CTCAGCGTCG | GCAAGGAGC | CATGGTTCTA | GCAACTAACT | TACCTGTTGA | AATTCGAACA | 1140 |
| CCCAAACAAC | TTGTTAATAT | CTATTCGAAG | CGAATGCAGA | TTGAAGAAAC | CTTCCGAGAC | 1200 |
| TTGAAAAGTC | CTGCCTACGG | ACTAGGCCTA | CGCCATAGCC | GAACGAGCAG | CTCAGAGCGT | 1260 |
| TTTGATATCA | TGCTGCTAAT | CGCCCTGATG | CTTCAACTAA | CATGTTGGCT | TGCGGGCGTT | 1320 |
| CATGCTCAGA | AACAAGGTTG | GGACAAGCAC | TTCCAGGCTA | ACACAGTCAG | AAATCGAAAC | 1380 |
| GTACTCTCAA | CAGTTCGCTT | AGGCATGGAA | GTTTTGCGGC | ATTCTGGCTA | CACAATAACA | 1440 |
| AGGGAAGACT | TACTCGTGGC | TGCAACCCTA | CTAGCTCAAA | ATTTATTCAC | ACATGGTTAC | 1500 |
| GCTTTGGGGA | AATTATGAGG | GGATCTTCGA | CCGTGACCAA | AGGTGCCTTT | TATCATCACT | 1560 |
| TTAAAAATAA | AAAACAATTA | CTCAGTGCCT | GTTATAAGCA | GCAATTAATT | ATGATTGATG | 1620 |
| CCTACATCAC | AACAAAAACT | GATTAACAA | ATGGTTGGTC | TGCCTTAGAA | AGTATATTTG | 1680 |
| AACATTATCT | TGATTATATT | ATTGATAATA | ATAAAAACCT | TATCCCTATC | CAAGAAGTGA | 1740 |
| TGCCTATCAT | TGGTTGGAAT | GAACTTGAAA | AAATTAGCCT | TGAATACATT | ACTGGTAAGG | 1800 |
| TAAACGCCAT | TGTCAGCAAA | TTGATCCAAG | AGAACCAACT | TAAAGCTTTC | CTGACGGAAT | 1860 |
| GTTAATTCTC | GTTGACCCTG | AGCACTGATG | AATCCCCTAA | TGATTTGGT | AAAAATCATT | 1920 |
| AAGTTAAGGT | GGATACACAT | CTTGTCATAT | GATCCCGGAT | CTGGGCAATA | GTTACCCTTA | 1980 |
| TTATCAAGAT | AAGAAAGAAA | AGGATTTTTC | GCTACGCTCA | AATCCTTTAA | AAAAACACAA | 2040 |
| AAGACCACAT | TTTTTAATGT | GGTCTTTATT | CTTCAACTAA | AGCACCCATT | AGTTCAACAA | 2100 |
| ACGAAAATTG | GATCCAAGGG | GTGATCGGTC | GGCGGAAATG | AAGGCCTGCG | GCGAGTGCGG | 2160 |
| GCCTTCTGTT | TTGAGGATTA | TAATCAGAGT | ATATTGAAAG | TTTCGCGATC | TTTTCGTATA | 2220 |
| ATTGTTTTAG | GCATAGTGCA | ATCGATTGTT | TGAGAAAAGA | AGAAGACCAT | AAAAATACCT | 2280 |
| TGTCTGTCAT | CAGACAGGGT | ATTTTTTATG | CTGTCCAGAC | TGTCCGCTGT | GTAAAAATAA | 2340 |
| GGAATAAAGG | GGGGTTGTTA | TTATTTTACT | GATATGTAAA | ATATAATTTG | TATAAGAAAA | 2400 |
| TGAGAGGGAG | AGGAAACATG | ATTCAAAAAC | GAAAGCGGAC | AGTTTCGTTC | AGACTTGTGC | 2460 |
| TTATGTGCAC | GCTGTTATTT | GTCAGTTTGC | CGATTACAAA | AACATCAGCC | GTAAATGGCA | 2520 |
| CGCTGATGCA | GTATTTTGAA | TGGTATACGC | CGAACGACGG | CCAGCATTGG | AAACGATTGC | 2580 |
| AGAATGATGC | GGAACATTTA | TCGGATTAAC | TTAACGTTAA | TATTTGTTTC | CCAATAGGCA | 2640 |
| AATCTTTCTA | ACTTTGATAC | GTTTAAACTA | CCAGCTTGGA | CAAGTTGGTA | TAAAAATGAG | 2700 |
| GAGGGAAACC | GAATGAAGAA | ACCGTTGGGG | AAAATTGTCG | CAAGCACCGC | ACTACTCATT | 2760 |
| TCTGTTGCTT | TTAGTTCATC | GATCGCATCG | GCTGCTGAAG | AAGCAAAAGA | AAAATATTTA | 2820 |
| ATTGGCTTTA | ATGAGCAGGA | AGCTGTCAGT | GAGTTTGTAG | AACAAGTAGA | GGCAAATGAC | 2880 |
| GAGGTCGCCA | TTCTCTCTGA | GGAAGAGGAA | GTCGAAATTG | AATTGCTTCA | TGAATTTGAA | 2940 |
| ACGATTCCTG | TTTTATCCGT | TGAGTTAAGC | CCAGAAGATG | TGGACGCGCT | TGAACTCGAT | 3000 |
| CCAGCGATTT | CTTATATTGA | AGAGGATGCA | GAAGTAACGA | CAATGGCGCA | ATCGGTACCA | 3060 |
| TGGGGAATTA | GCCGTGTGCA | AGCCCCAGCT | GCCCATAACC | GTGGATTGAC | AGGTTCTGGT | 3120 |
| GTAAAAGTTG | CTGTCCTCGA | TACAGGGATA | TCCACTCATC | CAGATCTAAA | TATTCGTGGT | 3180 |
| GGCGCAAGCT | TTGTACCAGG | GGAACCGTCG | ACTCAAGATG | GGAATGGGCA | TGGCACGCAT | 3240 |
| GTGGCCGGGA | CGATCGCTGC | TTTAAACAAT | TCGATTGGCG | TTCTTGGCGT | AGCGCCAGC | 3300 |
| GCTGAGCTAT | ACGCTGTTAA | AGTCCTAGGG | GCGAGCGGTT | CAGGTTCGGT | CAGCTCGATT | 3360 |

| | | | | | | |
|---|---|---|---|---|---|---|
| GCCCAAGGAT | TGGAATGGGC | AGGGAACAAT | GGCATGCACG | TTGCTAATTT | GAGTTTAGGA | 3420 |
| AGCCCTTCGC | CAAGTGCCAC | ACTCGAGCAA | GCTGTTAATA | GCGCGACTTC | TAGAGGCGTT | 3480 |
| CTTGTTGTAG | CGGCATCTGG | GAATTCAGGT | GCAGGCTCAA | TCAGCTATCC | GGCGCGCTAT | 3540 |
| GCGAACGCAA | TGGCAGTCGG | AGCTACTGAT | CAAAACAACA | ACCGCGCTAG | CTTTTCACAG | 3600 |
| TATGGCGCAG | GCCTTGACAT | TGTCGCACCC | GGGGTAAACG | TGCAGAGCAC | ATACCCAGGT | 3660 |
| TCAACATATG | CCAGCTTAAA | CGGTACATCG | ATGGCTACTC | CTCATGTTGC | AGGTGCGGCC | 3720 |
| GCCCTTGTTA | AACAAAGAA | CCCATCTTGG | TCTAATGTAC | AAATTCGAAA | TCATCTAAAG | 3780 |
| AATACGGCAA | CTAGTTTAGG | AAGCACGAAC | TTGTATGGAA | GCGGACTTGT | TAACGCAGAA | 3840 |
| GCGGCAACGC | GTTAATCAAT | AAAAAAACGC | TGTGCGGTTA | AAGGGCACAG | CGTTTTTTTG | 3900 |
| TGTATGGATC | CAGTGGGATA | TTTTTAAAAT | ATATATTTAT | GTTACAGTAA | TATTGACTTT | 3960 |
| TAAAAAGGA | TTGATTCTAA | TGAAGAAAGC | AGACAAGTAA | GCCTCCTAAA | TTCACTTTAG | 4020 |
| ATAAAAATTT | AGGAGGCATA | TCAAATGAAC | TTTAATAAAA | TTGATTTAGA | CAATTGGAAG | 4080 |
| AGAAAGAGA | TATTTAATCA | TTATTGAAC | CAACAAACGA | CTTTTAGTAT | AACCACAGAA | 4140 |
| ATTGATATTA | GTGTTTTATA | CCGAAACATA | AAACAAGAAG | GATATAAATT | TTACCCTGCA | 4200 |
| TTTATTTTCT | TAGTGACAAG | GGTGATAAAC | TCAAATACAG | CTTTTAGAAC | TGGTTACAAT | 4260 |
| AGCGACGGAG | AGTTAGGTTA | TTGGGATAAG | TTAGAGCCAC | TTTATACAAT | TTTTGATGGT | 4320 |
| GTATCTAAAA | CATTCTCTGG | TATTTGGACT | CCTGTAAAGA | ATGACTTCAA | AGAGTTTTAT | 4380 |
| GATTTATACC | TTTCTGATGT | AGAGAAATAT | AATGGTTCGG | GAAATTGTT | TCCCAAAACA | 4440 |
| CCTATACCTG | AAAATGCTTT | TTCTCTTTCT | ATTATTCCAT | GGACTTCATT | TACTGGGTTT | 4500 |
| AACTTAAATA | TCAATAATAA | TAGTAATTAC | CTTCTACCCA | TTATTACAGC | AGGAAAATTC | 4560 |
| ATTAATAAAG | GTAATTCAAT | ATATTTACCG | CTATCTTTAC | AGGTACATCA | TTCTGTTTGT | 4620 |
| GATGGTTATC | ATGCAGGATT | GTTTATGAAC | TCTATTCAGG | AATTGTCAGA | TAGGCCTAAT | 4680 |
| GACTGGCTTT | TATAATATGA | GATAATGCCG | ACTGTACTTT | TTACAGTCGG | TTTTCTAATG | 4740 |
| TCACTAACCT | GCCCGTTAG | TTGAAGAAGG | TTTTTATATT | ACAGCTCCAG | ATCCGGGATC | 4800 |
| ATATGACAAG | ATGTGTATCC | ACCTTAACTT | AATGATTTTT | ACCAAAATCA | TTAGGGGATT | 4860 |
| CATCAGTGCT | CAGGGTCAAC | GAGAATTAAC | ATTCCGTCAG | GAAAGCTTAG | CTTATGATGA | 4920 |
| TGATGTGCTT | AAAAACTTAC | TCAATGGCTG | GTTTATGCAT | ATCGCAATAC | ATGCGAAAAA | 4980 |
| CCTAAAAGAG | CTTGCCGATA | AAAAGGCCA | ATTTATTGCT | ATTTACCGCG | GCTTTTTATT | 5040 |
| GAGCTTGAAA | GATAAATAAA | ATAGATAGGT | TTTATTTGAA | GCTAAATCTT | CTTTATCGTA | 5100 |
| AAAAATGCCC | TCTTGGGTTA | TCAAGAGGGT | CATTATATTT | CGCGGAATAA | CATCATTTGG | 5160 |
| TGACGAAATA | ACTAAGCACT | TGTCTCCTGT | TTACTCCCCT | GAGCTTGAGG | GGTTAACATG | 5220 |
| AAGGTCATCG | ATAGAAAGCG | TGAGAAACAG | CGTACAGACG | ATTTAGAGAT | GTAGAGGTAC | 5280 |
| TTTTATGCCG | AGAAAACTTT | TTGCGTGTGA | CAGTCCTTAA | AATATACTTA | GAGCGTAAGC | 5340 |
| GAAAGTAGTA | GCGACAGCTA | TTAACTTTCG | GTTGCAAAGC | TCTAGGATTT | TTAATGGACG | 5400 |
| CAGCGCATCA | CACGCAAAAA | GGAAATTGGA | ATAAATGCGA | AATTTGAGAT | GTTAATTAAA | 5460 |
| GACCTTTTTG | AGGTCTTTTT | TTCTTAGATT | TTTGGGGTTA | TTTAGGGGAG | AAAACATAGG | 5520 |
| GGGGTACTAC | GACCTCCCCC | CTAGGTGTCC | ATTGTCCATT | GTCCAAACAA | ATAAATAAAT | 5580 |
| ATTGGGTTTT | TAATGTTAAA | AGGTTGTTTT | TTATGTTAAA | GTGAAAAAAA | CAGATGTTGG | 5640 |
| GAGGTACAGT | GATAGTTGTA | GATAGAAAAG | AAGAGAAAAA | AGTTGCTGTT | ACTTTAAGAC | 5700 |
| TTACAACAGA | AGAAAATGAG | ATATTAAATA | GAATCAAAGA | AAAATATAAT | ATTAGCAAAT | 5760 |

| | | | | | | |
|---|---|---|---|---|---|---|
| CAGATGCAAC | CGGTATTCTA | ATAAAAAAAT | ATGCAAAGGA | GGAATACGGT | GCATTTTAAA | 5820 |
| CAAAAAAGA | TAGACAGCAC | TGGCATGCTG | CCTATCTATG | ACTAAATTTT | GTTAAGTGTA | 5880 |
| TTAGCACCGT | TATTATATCA | TGAGCGAAAA | TGTAATAAAA | GAAACTGAAA | ACAAGAAAAA | 5940 |
| TTCAAGAGGA | CGTAATTGGA | CATTTGTTTT | ATATCCAGAA | TCAGCAAAAG | CCGAGTGGTT | 6000 |
| AGAGTATTTA | AAAGAGTTAC | ACATTCAATT | TGTAGTGTCT | CCATTACATG | ATAGGGATAC | 6060 |
| TGATACAGAA | GGTAGGATGA | AAAAGAGCA | TTATCATATT | CTAGTGATGT | ATGAGGGTAA | 6120 |
| TAAATCTTAT | GAACAGATAA | AATAATTAA | CAGAAGAATT | GAATGCGACT | ATTCCGCAGA | 6180 |
| TTGCAGGAAG | TGTGAAAGGT | CTTGTGAGAT | ATATGCTTCA | CATGGACGAT | CCTAATAAAT | 6240 |
| TTAAATATCA | AAAAGAAGAT | ATGATAGTTT | ATGGCGGTGT | AGATGTTGAT | GAATTATTAA | 6300 |
| AGAAAACAAC | AACAGATAGA | TATAAATTAA | TTAAAGAAAT | GATTGAGTTT | ATTGATGAAC | 6360 |
| AAGGAATCGT | AGAATTTAAG | AGTTTAATGG | ATTATGCAAT | GAAGTTTAAA | TTTGATGATT | 6420 |
| GGTTCCCGCT | TTTATGTGAT | AACTCGGCGT | ATGTTATTCA | AGAATATATA | AAATCAAATC | 6480 |
| GGTATAAATC | TGACCGATAG | ATTTTGAATT | TAGGTGTCAC | AAGACACTCT | TTTTCGCAC | 6540 |
| CAGCGAAAAC | TGGTTTAAGC | CGACTGCGCA | AAAGACATAA | TCGGGAATTC | CCGATTCACA | 6600 |
| AAAATAGGC | ACACGAAAAA | CAAGTTAAGG | GATGCAGTTT | ATGCATCCCT | TAACTTACTT | 6660 |
| ATTAAATAAT | TTATAGCTAT | TGAAAAGAGA | TAAGAATTGT | TCAAAGCTAA | TATTGTTTAA | 6720 |
| ATCGTCAATT | CCTGCATGTT | TTAAGGAATT | GTTAAATTGA | TTTTTTGTAA | ATATTTTCTT | 6780 |
| GTATTCTTTG | TTAACCCATT | TCATAACGAA | ATAATTATAC | TTTTGTTTAT | CTTTGTGTGA | 6840 |
| TATTCTTGAT | TTTTTTCTAC | TTAATCTGAT | AAGTGAGCTA | TTCACTTTAG | GTTAGGATG | 6900 |
| AAAATATTCT | CTTGGAACCA | TACTTAATAT | AGAAATATCA | ACTTCTGCCA | TAAAAGTAA | 6960 |
| TGCCAATGAG | CGTTTTGTAT | TTAATAATCT | TTTAGCAAAC | CCGTATTCCA | CGATTAAATA | 7020 |
| AATCTCATTA | GCTATACTAT | CAAAAACAAT | TTGCGTATT | ATATCCGTAC | TTATGTTATA | 7080 |
| AGGTATATTA | CCATATATTT | TATAGGATTG | GTTTTTAGGA | AATTTAAACT | GCAATATATC | 7140 |
| CTTGTTTAAA | ACTTGGAAAT | TATCGTGATC | AACAAGTTTA | TTTTCTGTAG | TTTTGCATAA | 7200 |
| TTTATGGTCT | ATTTCAATGG | CAGTTACGAA | ATTACACCTC | TTTACTAATT | CAAGGGTAAA | 7260 |
| ATGGCCTTTT | CCTGAGCCGA | TTTCAAAGAT | ATTATCATGT | TCATTTAATC | TTATATTTGT | 7320 |
| CATTATTTTA | TCTATATTAT | GTTTTGAAGT | AATAAAGTTT | TGACTGTGTT | TTATATTTTT | 7380 |
| CTCGTTCATT | ATAACCCTCT | TTAATTTGGT | TATATGAATT | TTGCTTATTA | ACGATTCATT | 7440 |
| ATAACCACTT | ATTTTTTGTT | TGGTTGATAA | TGAACTGTGC | TGATTACAAA | AATACTAAAA | 7500 |
| ATGCCCATAT | TTTTTCCTCC | TTATAAAATT | AGTATAATTA | TAGCACGAGC | TCTGATAAAT | 7560 |
| ATGAACATGA | TGAGTGATCG | TTAAATTTAT | ACTGCAATCG | GATGCGATTA | TTGAATAAAA | 7620 |
| GATATGAGAG | ATTTATCTAA | TTTCTTTTTT | CTTGTAAAAA | AAGAAAGTTC | TTAAAGGTTT | 7680 |
| TATAGTTTTG | GTCGTAGAGC | ACACGGTTTA | ACGACTTAAT | TACGAAGTAA | ATAAGTCTAG | 7740 |
| TGTGTTAGAC | TTTATGAAAT | CTATATACGT | TTATATATAT | TTATTATCCG | GAGGTGTAGC | 7800 |
| ATGTCTCATT | CAATTTTGAG | GGTTGCCAGA | GTTAAAGGAT | CAAGTAATAC | AAACGGGATA | 7860 |
| CAAAGACATA | ATCAAAGAGA | GAATAAAAAC | TATAATAATA | AAGACATAAA | TCATGAGGAA | 7920 |
| ACATATAAAA | ATTATGATTT | GATTAACGCA | CAAAATATAA | AGTATAAAGA | TAAAATTGAT | 7980 |
| GAAACGATTG | ATGAGAATTA | TTCAGGGAAA | CGTAAAATTC | GGTCAGATGC | AATTCGACGA | 8040 |
| TAAGCTAGCT | TTAATGCGGT | AGTTTATCAC | AGTTAAATTG | CTAACGCAGT | CAGGCACCGT | 8100 |
| GTATGAAATC | TAACAATGCG | CTCATCGTCA | TCCTCGGCAC | CGTCACCCTG | GATGCTGTAG | 8160 |

-continued

| | | | | | | |
|---|---|---|---|---|---|---|
| GCATAGGCTT | GGTTATGCCG | GTACTGCCGG | GCCTCTTGCG | GGATGCTCTT | CCGCTTCCTC | 8220 |
| GCTCACTGAC | TCGCTGCGCT | CGGTCGTTCG | GCTGCGGCGA | GCGGTATCAG | CTCACTCAAA | 8280 |
| GGCGGTAATA | CGGTTATCCA | CAGAATCAGG | GGATAACGCA | GGAAAGAACA | TGTGAGCAAA | 8340 |
| AGGCCAGCAA | AAGGCCAGGA | ACCGTAAAAA | GGCCGCGTTG | CTGGCGTTTT | TCCATAGGCT | 8400 |
| CCGCCCCCCT | GACGAGCATC | ACAAAAATCG | ACGCTCAAGT | CAGAGGTGGC | GAAACCCGAC | 8460 |
| AGGACTATAA | AGATACCAGG | CGTTTCCCCC | TGGAAGCTCC | CTCGTGCGCT | CTCCTGTTCC | 8520 |
| GACCCTGCCG | CTTACCGGAT | ACCTGTCCGC | CTTTCTCCCT | TCGGGAAGCG | TGGCGCTTTC | 8580 |
| TCAATGCTCA | CGCTGTAGGT | ATCTCAGTTC | GGTGTAGGTC | GTTCGCTCCA | AGCTGGGCTG | 8640 |
| TGTGCACGAA | CCCCCCGTTC | AGCCCGACCG | CTGCGCCTTA | TCCGGTAACT | ATCGTCTTGA | 8700 |
| GTCCAACCCG | GTAAGACACG | ACTTATCGCC | ACTGGCAGCA | GCCACTGGTA | ACAGGATTAG | 8760 |
| CAGAGCGAGG | TATGTAGGCG | GTGCTACAGA | GTTCTTGAAG | TGGTGGCCTA | ACTACGGCTA | 8820 |
| CACTAGAAGG | ACAGTATTTG | GTATCTGCGC | TCTGCTGAAG | CCAGTTACCT | TCGGAAAAG | 8880 |
| AGTTGGTAGC | TCTTGATCCG | GCAAACAAAC | CACCGCTGGT | AGCGGTGGTT | TTTTGTTTG | 8940 |
| CAAGCAGCAG | ATTACGCGCA | GAAAAAAGG | ATCTCAAGAA | GATCCTTTGA | TCTTTTCTAC | 9000 |
| GGGGTCTGAC | GCTCAGTGGA | ACGAAAACTC | ACGTTAAGGG | ATTTTGGTCA | TGAGATTATC | 9060 |
| AAAAGGATC | TTCACCTAGA | TCCTTTTAAA | TTAAAAATGA | AGTTTTAAAT | CAATCTAAAG | 9120 |
| TATATATGAG | TAAACTTGGT | CTGACAGTTA | CCAATGCTTA | ATCAGTGAGG | CACCTATCTC | 9180 |
| AGCGATCTGT | CTATTTCGTT | CATCCATAGT | TGCCTGACTC | CCCGTCGTGT | AGATAACTAC | 9240 |
| GATACGGGAG | GGCTTACCAT | CTGGCCCCAG | TGCTGCAATG | ATACCGCGAG | ACCCACGCTC | 9300 |
| ACCGGCTCCA | GATTTATCAG | CAATAAACCA | GCCAGCCGGA | AGGGCCGAGC | GCAGAAGTGG | 9360 |
| TCCTGCAACT | TTATCCGCCT | CCATCCAGTC | TATTAATTGT | TGCCGGGAAG | CTAGAGTAAG | 9420 |
| TAGTTCGCCA | GTTAATAGTT | TGCGCAACGT | TGTTGCCATT | GCTGCAGGCA | TCGTGGTGTC | 9480 |
| ACGCTCGTCG | TTTGGTATGG | CTTCATTCAG | CTCCGGTTCC | CAACGATCAA | GGCGAGTTAC | 9540 |
| ATGATCCCCC | ATGTTGTGCA | AAAAAGCGGT | TAGCTCCTTC | GGTCCTCCGA | TCGTTGTCAG | 9600 |
| AAGTAAGTTG | GCCGCAGTGT | TATCACTCAT | GGTTATGGCA | GCACTGCATA | ATTCTCTTAC | 9660 |
| TGTCATGCCA | TCCGTAAGAT | GCTTTTCTGT | GACTGGTGAG | TACTCAACCA | AGTCATTCTG | 9720 |
| AGAATAGTGT | ATGCGGCGAC | CGAGTTGCTC | TTGCCCGGCG | TCAACACGGG | ATAATACCGC | 9780 |
| GCCACATAGC | AGAACTTTAA | AAGTGCTCAT | CATTGGAAAA | CGTTCTTCGG | GGCGAAAACT | 9840 |
| CTCAAGGATC | TTACCGCTGT | TGAGATCCAG | TTCGATGTAA | CCCACTCGTG | CACCCAACTG | 9900 |
| ATCTTCAGCA | TCTTTTACTT | TCACCAGCGT | TTCTGGGTGA | GCAAAAACAG | GAAGGCAAA | 9960 |
| TGCCGCAAAA | AAGGGAATAA | GGGCGACACG | GAAATGTTGA | ATACTCATAC | TCTTCCTTTT | 10020 |
| TCAATATTAT | TGAAGCATTT | ATCAGGGTTA | TTGTCTCATG | AGCGGATACA | TATTTGAATG | 10080 |
| TATTTAGAAA | AATAAACAAA | TAGGGGTTCC | GCGCACATTT | CCCCGAAAAG | TGCCACCTGA | 10140 |
| CGTCTAAGAA | ACCATTATTA | TCATGACATT | AACCTATAAA | AATAGGCGTA | TCACGAGGCC | 10200 |
| CTTTCGTCTT | CAAGAA | | | | | 10216 |

( 2 ) INFORMATION FOR SEQ ID NO: 2:

( i ) SEQUENCE CHARACTERISTICS:
        ( A ) LENGTH: 6169 base pairs
        ( B ) TYPE: nucleic acid
        ( C ) STRANDEDNESS: single
        ( D ) TOPOLOGY: linear ( i i ) MOLECULE TYPE: other nucleic acid (A) DESCRIPTION: /desc = "pSJ2739"

(vi) ORIGINAL SOURCE:
  (A) ORGANISM: pSJ2739

(xi) SEQUENCE DESCRIPTION: SEQ ID NO: 2:

| | | | | | |
|---|---|---|---|---|---|
| TCTGGACTGT | CCAAACATGG | TTTAAGCCGC | TTGCTTACGC | TTTTATTCTC | ACAAGGGAAT | 60 |
| CTGGATACCC | TCAGGTTTTC | TACGGGGATA | TGTACGGGAC | GAAAGGAGAC | TCCCAGCGCG | 120 |
| AAATTCCTGC | CTTGAAACAC | AAAATTGAAC | CGATCTTAAA | AGCGAGAAAA | CAGTATGCGT | 180 |
| ACGGAGCACA | GCATGATTAT | TTCGACCACC | ATGACATTGT | CGGCTGGACA | AGGGAAGGCG | 240 |
| ACAGCTCGGT | TGCAAATTCA | GGTTTGGCGG | CATTAATAAC | AGACGGACCC | GGTGGGGCAA | 300 |
| AGCGAATGTA | TGTCGGCCGG | CAAAACGCCG | GTGAGACATG | GCATGACATT | ACCGGAAACC | 360 |
| GTTCGGAGCC | GGTTGTCATC | AATTCGGAAG | GCTGGGGAGA | GTTTCACGTA | AACGGCGGGT | 420 |
| CGGTTTCAAT | TTATGTTCAA | AGATAGAAGA | GCAGAGAGGA | CGGATTTCCT | GAAGGAAATC | 480 |
| CGTTTTTTTA | TTTTGCCCGT | CTTATAAATT | TCGTTGATTA | CATTTTATAA | TTAATTTTAA | 540 |
| CAAAGTGTCA | TAAGCCCTCA | GGAATATTGC | TGACAGTTTA | GAATCCCTAG | GTAAGGCGGG | 600 |
| GATGAAATGG | CAACGTTATC | TGATGTAGCA | AAGAAAGAAA | TGTGTCGAAA | ATGACGGTAT | 660 |
| CGCGGGTGAT | CAATCATCCT | GAGACTGTGA | CGGATGAATT | GAAAAGCTT | GCATGCCTGC | 720 |
| AGGTCGATTC | ACAAAAAATA | GGCACACGAA | AAACAAGTTA | AGGGATGCAG | TTTATGCATC | 780 |
| CCTTAACTTA | CTTATTAAAT | AATTTATAGC | TATTGAAAAG | AGATAAGAAT | TGTTCAAAGC | 840 |
| TAATATTGTT | TAAATCGTCA | ATTCCTGCAT | GTTTTAAGGA | ATTGTTAAAT | TGATTTTTG | 900 |
| TAAATATTTT | CTTGTATTCT | TTGTTAACCC | ATTTCATAAC | GAAATAATTA | TACTTTTGTT | 960 |
| TATCTTTGTG | TGATATTCTT | GATTTTTTC | TACTTAATCT | GATAAGTGAG | CTATTCACTT | 1020 |
| TAGGTTTAGG | ATGAAAATAT | TCTCTTGGAA | CCATACTTAA | TATAGAAATA | TCAACTTCTG | 1080 |
| CCATTAAAAG | TAATGCCAAT | GAGCGTTTTG | TATTTAATAA | TCTTTTAGCA | AACCCGTATT | 1140 |
| CCACGATTAA | ATAAATCTCA | TTAGCTATAC | TATCAAAAAC | AATTTTGCGT | ATTATATCCG | 1200 |
| TACTTATGTT | ATAAGGTATA | TTACCATATA | TTTTATAGGA | TTGGTTTTTA | GGAAATTTAA | 1260 |
| ACTGCAATAT | ATCCTTGTTT | AAAACTTGGA | AATTATCGTG | ATCAACAAGT | TTATTTTCTG | 1320 |
| TAGTTTTGCA | TAATTTATGG | TCTATTTCAA | TGGCAGTTAC | GAAATTACAC | CTCTTTACTA | 1380 |
| ATTCAAGGGT | AAAATGGCCT | TTTCCTGAGC | CGATTTCAAA | GATATTATCA | TGTTCATTTA | 1440 |
| ATCTTATATT | TGTCATTATT | TTATCTATAT | TATGTTTTGA | AGTAATAAAG | TTTTGACTGT | 1500 |
| GTTTTATATT | TTTCTCGTTC | ATTATAACCC | TCTTTAATTT | GGTTATATGA | ATTTGCTTA | 1560 |
| TTAACGATTC | ATTATAACCA | CTTATTTTTT | GTTGGTTGA | TAATGAACTG | TGCTGATTAC | 1620 |
| AAAAATACTA | AAAATGCCCA | TATTTTTTCC | TCCTTATAAA | ATTAGTATAA | TTATAGCACG | 1680 |
| AGCTCTGATA | AATATGAACA | TGATGAGTGA | TCGTTAAATT | TATACTGCAA | TCGGATGCGA | 1740 |
| TTATTGAATA | AAAGATATGA | GAGATTTATC | TAATTTCTTT | TTTCTTGTAA | AAAAAGAAAG | 1800 |
| TTCTTAAAGG | TTTTATAGTT | TTGGTCGTAG | AGCACACGGT | TTAACGACTT | AATTACGAAG | 1860 |
| TAAATAAGTC | TAGTGTGTTA | GACTTTATGA | AATCTATATA | CGTTTATATA | TATTTATTAT | 1920 |
| CCGGAGGTGT | AGCATGTCTC | ATTCAATTTT | GAGGGTTGCC | AGAGTTAAAG | GATCAAGTAA | 1980 |
| TACAAACGGG | ATACAAAGAC | ATAATCAAAG | AGAGAATAAA | AACTATAATA | ATAAAGACAT | 2040 |
| AAATCATGAG | GAAACATATA | AAAATTATGA | TTTGATTAAC | GCACAAAATA | TAAAGTATAA | 2100 |
| AGATAAAATT | GATGAAACGA | TTGATGAGAA | TTATTCAGGG | AAACGTAAAA | TTCGGTCAGA | 2160 |
| TGCAATTCGA | CATGTGGACG | GACTGGTTAC | AAGTGATAAA | GATTTCTTTG | ATGATTTAAG | 2220 |

```
CGGAGAAGAA ATAGAACGAT TTTTTAAAGA TAGCTTGGAG TTTCTAGAAA ATGAATACGG   2280
TAAGGAAAAT ATGCTGTATG CGACTGTCCA TCTGGATGAA AGAGTCCCAC ATATGCACTT   2340
TGGTTTTGTC CCTTTAACAG AGGACGGGAG ATTGTCTGCA AAAGAACAGT TAGGCAACAA   2400
GAAAGACTTT ACTCAATTAC AAGATAGATT TAATGAGTAT GTGAATGAGA AAGGTTATGA   2460
ACTTGAAAGA GGCACGTCCA AAGAGGTTAC AGAACGAGAA CATAAAGCGA TGGATCAGTA   2520
CAAGAAAGAT ACTGTATTTC ATAAACAGGA ACTGCAAGAA GTTAAGGATG AGTTACAGAA   2580
GGCAAATAAG CAGTTACAGA GTGGAATAGA GCATATGAGG TCTACGAAAC CCTTTGATTA   2640
TGAAAATGAG CGTACAGGTT TGTTCTCTGG ACGTGAAGAG ACTGGTAGAA AGATATTAAC   2700
TGCTGATGAA TTTGAACGCC TGCAAGAAAC AATCTCTTCT GCAGAACGGA TTGTTGATGA   2760
TTACGAAAAT ATTAAGAGCA CAGACTATTA CACAGAAAAT CAAGAATTAA AAAAACGTAG   2820
AGAGAGTTTG AAAGAAGTAG TGAATACATG GAAAGAGGGG TATCACGAAA AAAGTAAAGA   2880
GGTTAATAAA TTAAAGCGAG AGAATGATAG TTTGAATGAG CAGTTGAATG TATCAGAGAA   2940
ATTTCAAGCT AGTACAGTGA CTTTATATCG TGCTGCGAGG GCGAATTTCC CTGGGTTTGA   3000
GAAAGGGTTT AATAGGCTTA AAGAGAAATT CTTTAATGAT TCCAAATTTG AGCGTGTGGG   3060
ACAGTTTATG GATGTTGTAC AGGATAATGT CCAGAAGGTC GATAGAAAGC GTGAGAAACA   3120
GCGTACAGAC GATTAGAGA TGTAGAGGTA CTTTATGCC GAGAAACTT TTTGCGTGTG   3180
ACAGTCCTTA AAATATACTT AGAGCGTAAG CGAAAGTAGT AGCGACAGCT ATTAACTTTC   3240
GGTTTCAAAG CTCTAGGATT TTTAATGGAC GCAGCGCATC ACACGCAAAA AGGAAATTGG   3300
AATAAATGCG AAATTTGAGA TGTTAATTAA AGACCTTTTT GAGGTCTTTT TTTCTTAGAT   3360
TTTTGGGGTT ATTTAGGGGA GAAAACATAG GGGGGTACTA CGACCTCCCC CCTAGGTGTC   3420
CATTGTCCAT TGTCCAAACA AATAAATAAA TATTGGGTTT TTAATGTTAA AAGGTTGTTT   3480
TTTATGTTAA AGTGAAAAAA ACAGATGTTG GGAGGTACAG TGATGGTTGT AGATAGAAAA   3540
GAAGAGAAAA AAGTTGCTGT TACTTTAAGA CTTACAACAG AAGAAAATGA GATATTAAAT   3600
AGAATCAAAG AAAAATATAA TATTAGCAAA TCAGATGCAA CCGGTATTCT AATAAAAAAA   3660
TATGCAAAGG AGGAATACGG TGCATTTTAA ACAAAAAAG ATAGACAGCA CTGGCATGCT   3720
GCCTATCTAT GACTAAATTT TGTTAAGTGT ATTAGCACCG TTATTATATC ATGAGCGAAA   3780
ATGTAATAAA AGAAACTGAA AACAAGAAAA ATTCAAGAGG ACGTAATTGG ACATTTGTTT   3840
TATATCCAGA ATCAGCAAAA GCCGAGTGGT TAGAGTATTT AAAAGAGTTA CACATTCAAT   3900
TTGTAGTGTC TCCATTACAT GATAGGGATA CTGATACAGA AGGTAGGATG AAAAAAGAGC   3960
ATTATCATAT TCTAGTGATG TATGAGGGTA ATAAATCTTA TGAACAGATA AAAATAATTA   4020
CAGAAGAATT GAATGCGACT ATTCCGCAGA TTGCAGGAAG TGTGAAAGGT CTTGTGAGAT   4080
ATATGCTTCA CATGGACGAT CCTAATAAAT TTAAATATCA AAAAGAAGAT ATGATAGTTT   4140
ATGGCGGTGT AGATGTTGAT GAATTATTAA AGAAAACAAC AACAGATAGA TATAAATTAA   4200
TTAAAGAAAT GATTGAGTTT ATTGATGAAC AAGGAATCGT AGAATTTAAG AGTTAATGG   4260
ATTATGCAAT GAAGTTTAAA TTTGATGATT GGTTCCCGCT TTTATGTGAT AACTCGGCGT   4320
ATGTTATTCA AGAATATATA AAATCAAATC GGTATAAATC TGACCGATAG ATTTTGAATT   4380
TAGGTGTCAC AAGACACTCT TTTTTCGCAC CAGCGAAAAC TGGTTTAAGC CGACTGCGCA   4440
AAAGACATAA TCGACTCTAG AGGATCCCCG GGTACCGAGC TCTGCCTTTT AGTCCAGCTG   4500
ATTTCACTTT TTGCATTCTA CAAACTGCAT AACTCATATG TAAATCGCTC CTTTTAGGT   4560
GGCACAAATG TGAGGCATTT TCGCTCTTTC CGGCAACCAC TTCCAAGTAA AGTATAACAC   4620
```

| | | | | | | |
|---|---|---|---|---|---|---|
| ACTATACTTT | ATATTCATAA | AGTGTGTGCT | CTGCGAGGCT | GTCGGCAGTG | CCGACCAAAA | 4680 |
| CCATAAAACC | TTTAAGACCT | TTCTTTTTTT | TACGAGAAAA | AAGAAACAAA | AAAACCTGCC | 4740 |
| CTCTGCCACC | TCAGCAAAGG | GGGGTTTTGC | TCTCGTGCTC | GTTTAAAAAT | CAGCAAGGGA | 4800 |
| CAGGTAGTAT | TTTTTGAGAA | GATCACTCAA | AAAATCTCCA | CCTTTAAACC | CTTGCCAATT | 4860 |
| TTTATTTTGT | CCGTTTGTC | TAGCTTACCG | AAAGCCAGAC | TCAGCAAGAA | TAAAATTTTT | 4920 |
| ATTGTCTTTC | GGTTTTCTAG | TGTAACGGAC | AAAACCACTC | AAAATAAAAA | AGATACAAGA | 4980 |
| GAGGTCTCTC | GTATCTTTTA | TTCAGCAATC | GCGCCCGATT | GCTGAACAGA | TTAATAATGA | 5040 |
| GCTCGAATTC | ATGAGATCCA | AATGTAAAAG | TTCAAATGAT | TCGACCGAAA | AATAAATATA | 5100 |
| AATCGGATAT | ACAATCGGCA | ATTGACGAAA | CTGCAAAATA | TCCTGTAAAG | GATACGGATT | 5160 |
| TTATGACCGA | TGATGAAGAA | AAGAATTTGA | AACGTTTGTC | TGATTTGGAG | GAAGGTTTAC | 5220 |
| ACCGTAAAAG | GTTAATCTCC | TATGGTGGTT | TGTTAAAAGA | AATACATAAA | AAATTAAACC | 5280 |
| TTGATGACAC | AGAAGAAGGC | GATTTGATTC | ATACAGATGA | TGACGAAAAA | GCCGATGAAG | 5340 |
| ATGGATTTTG | TATTATTGCA | ATGTGGAATT | GGGAACGGAA | AAATTATTTT | ATTAAAGAGT | 5400 |
| AGTTCAACAA | ACGGGCCAGT | TTGTTGAAGA | TTAGATGCTA | TAATTGTTAT | TAAAAGGATT | 5460 |
| GAAGGATGCT | TAGGAAGACG | AGTTATTAAT | AGCTGAATAA | GAACGGTGCT | CTCCAAATAT | 5520 |
| TCTTATTTAG | AAAAGCAAAT | CTAAAATTAT | CTGAAAAGGG | AATGAGAATA | GTGAATGGAC | 5580 |
| CAATAATAAT | GACTAGAGAA | GAAAGAATGA | AGATTGTTCA | TGAAATTAAG | GAACGAATAT | 5640 |
| TGGATAAATA | TGGGGATGAT | GTTAAGGCTA | TTGGTGTTTA | TGGCTCTCTT | GGTCGTCAGA | 5700 |
| CTGATGGGCC | CTATTCGGAT | ATTGAGATGA | TGTGTGTCAT | GTCAACAGAG | GAAGCAGAGT | 5760 |
| TCAGCCATGA | ATGGACAACC | GGTGAGTGGA | AGGTGGAAGT | GAATTTTGAT | AGCGAAGAGA | 5820 |
| TTCTACTAGA | TTATGCATCT | CAGGTGGAAT | CAGATTGGCC | GCTTACACAT | GGTCAATTTT | 5880 |
| TCTCTATTTT | GCCGATTTAT | GATTCAGGTG | GATACTTAGA | GAAAGTGTAT | CAAACTGCTA | 5940 |
| AATCGGTAGA | AGCCCAAACG | TTCCACGATG | CGATTTGTGC | CCTTATCGTA | GAAGAGCTGT | 6000 |
| TTGAATATGC | AGGCAAATGG | CGTAATATTC | GTGTGCAAGG | ACCGACAACA | TTTCTACCAT | 6060 |
| CCTTGACTGT | ACAGGTAGCA | ATGGCAGGTG | CCATGTTGAT | TGGTCTGCAT | CATCGCATCT | 6120 |
| GTTATACGAC | GAGCGCTTCG | GTCTTAACTG | AAGCAGTTAA | GCAATCAGA | | 6169 |

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "LWN5037"

(xi) SEQUENCE DESCRIPTION: SEQ ID NO: 3:

| | | |
|---|---|---|
| CCCACTGGAT | CCAATTTTCG | TTTGTTG | 27 |

(2) INFORMATION FOR SEQ ID NO: 4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "LWN5038"

( x i ) SEQUENCE DESCRIPTION: SEQ ID NO: 4:

GCAAATTGAT CCAAGAGAAC CAAC 24

( 2 ) INFORMATION FOR SEQ ID NO: 5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "LWN5036"

( x i ) SEQUENCE DESCRIPTION: SEQ ID NO: 5:

CAACAAACGA AAATTGGATC CAGTGGG 27

( 2 ) INFORMATION FOR SEQ ID NO: 6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "LWN5039"

( x i ) SEQUENCE DESCRIPTION: SEQ ID NO: 6:

GCACATCATC ATCATAAGC 19

( 2 ) INFORMATION FOR SEQ ID NO: 7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "LWN5136"

( x i ) SEQUENCE DESCRIPTION: SEQ ID NO: 7:

CCGGCGGATC CAAGGGGTGA TCG 23

( 2 ) INFORMATION FOR SEQ ID NO: 8:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "LWN2043"

( x i ) SEQUENCE DESCRIPTION: SEQ ID NO: 8:

GGGGTACTAG TAACCCGGGC CCGGCGTAGA GGATCCATAC ACAAA 45

( 2 ) INFORMATION FOR SEQ ID NO: 9:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "LWN5232"

( x i ) SEQUENCE DESCRIPTION: SEQ ID NO: 9:

GTCGGAGCTC ATTATTAATC TGTTCAGCAA TCGGGC                                        36

( 2 ) INFORMATION FOR SEQ ID NO: 10:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "LWN5233"

( x i ) SEQUENCE DESCRIPTION: SEQ ID NO: 10:

GTCGGAGCTC TGCCTTTTAG TCCAGCTGAT TTCAC                                         35

( 2 ) INFORMATION FOR SEQ ID NO: 11:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "LWN7839"

( x i ) SEQUENCE DESCRIPTION: SEQ ID NO: 11:

GACGGGATCC CTGCAGTATC CAATTTATTT TTTTCTTAAC AAGG                               44

( 2 ) INFORMATION FOR SEQ ID NO: 12:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "LWN7840"

( x i ) SEQUENCE DESCRIPTION: SEQ ID NO: 12:

GACGGATTCA AAGCTTAAAG CACTTGCATA GGCTAATGCC                                    40

( 2 ) INFORMATION FOR SEQ ID NO: 13:

( i ) SEQUENCE CHARACTERISTICS:
    ( A ) LENGTH: 98 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "LWN7794"

( x i ) SEQUENCE DESCRIPTION: SEQ ID NO: 13:

GACGGGTACC ACGCGTTAAT CAATAAAAAA ACGCTGTGCG GTTAAAGGGC ACAGCGTTTT              60

TTTGTGTATG GATCCTTCTA TCTTTTATAG GTCATTAG                                     98

( 2 ) INFORMATION FOR SEQ ID NO: 14:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear (i i) MOLECULE TYPE: other nucleic acid
  (A) DESCRIPTION: /desc = "LWN7790"

(x i) SEQUENCE DESCRIPTION: SEQ ID NO: 14:

TATATATTTT AAAAATATCC CACGGTTCTT CAAATATTTC TCC    43

(2) INFORMATION FOR SEQ ID NO: 15:

(i) SEQUENCE CHARACTERISTICS:
    (A) LENGTH: 44 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "LWN7789"

(x i) SEQUENCE DESCRIPTION: SEQ ID NO: 15:

GGAGAAATAT TTGAAGAACC GTGGGATATT TTTAAAATAT ATAT    44

(2) INFORMATION FOR SEQ ID NO: 16:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "LWN7788"

(x i) SEQUENCE DESCRIPTION: SEQ ID NO: 16:

CAAGTGTTCG CTTCGCTCTC ACGGAGCTGT AATATAAAAA CCTTC    45

(2) INFORMATION FOR SEQ ID NO: 17:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "LWN7787"

(x i) SEQUENCE DESCRIPTION: SEQ ID NO: 17:

GAAGGTTTTT ATATTACAGC TCCGTGAGAG CGAAGCGAAC ACTTG    45

(2) INFORMATION FOR SEQ ID NO: 18:

(i) SEQUENCE CHARACTERISTICS:
    (A) LENGTH: 45 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "LWN7784"

(x i) SEQUENCE DESCRIPTION: SEQ ID NO: 18:

CATATGATCA AATGGTTCGG ATCTGATTTT CCTCCTCTAA TATGC    45

(2) INFORMATION FOR SEQ ID NO: 19:

(i) SEQUENCE CHARACTERISTICS:
    (A) LENGTH: 55 base pairs
    (B) TYPE: nucleic acid
    (C) STRANDEDNESS: single
    (D) TOPOLOGY: linear (i i) MOLECULE TYPE: other nucleic acid
    (A) DESCRIPTION: /desc = "LWN8197"

(x i) SEQUENCE DESCRIPTION: SEQ ID NO: 19:

GCATATTAGA GGAGGAAAAT CAGATCCGAA CCATTTGATC ATATGACAAG ATGTG    55

(2) INFORMATION FOR SEQ ID NO: 20:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "LWN7791"

(x i) SEQUENCE DESCRIPTION: SEQ ID NO: 20:

GACGGAATTC CCGCGGTAAA TAGCAATAAA TTGGC    35

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "LWN7780"

(x i) SEQUENCE DESCRIPTION: SEQ ID NO: 21:

GACGGGTACC ACGCGTTAAT C    21

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "LWN5067"

(x i) SEQUENCE DESCRIPTION: SEQ ID NO: 22:

CCAGAACCTG TCAATCCACG    20

(2) INFORMATION FOR SEQ ID NO: 23:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "LWN8524"

(x i) SEQUENCE DESCRIPTION: SEQ ID NO: 23:

GACTGAATTC GGATCCACGC GTATAATAAA GAATAATTAT TAATCTGTAG    50

(2) INFORMATION FOR SEQ ID NO: 24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (  i  i  ) MOLECULE TYPE: other nucleic acid
            ( A ) DESCRIPTION: /desc = "LWN8528"

( x i ) SEQUENCE DESCRIPTION: SEQ ID NO: 24:

GACTAAGCTT GAGCTCCACT AATATTAATA AACTATCGAA GG 42

( 2 ) INFORMATION FOR SEQ ID NO: 25:

( i ) SEQUENCE CHARACTERISTICS:
            ( A ) LENGTH: 42 base pairs
            ( B ) TYPE: nucleic acid
            ( C ) STRANDEDNESS: single
            ( D ) TOPOLOGY: linear (  i  i  ) MOLECULE TYPE: other nucleic acid
            ( A ) DESCRIPTION: /desc = "LWN8529"

( x i ) SEQUENCE DESCRIPTION: SEQ ID NO: 25:

GACTGAATTC CTGCAGGAGC TCAGTGAGAG CGAAGCGAAC AC 42

( 2 ) INFORMATION FOR SEQ ID NO: 26:

( i ) SEQUENCE CHARACTERISTICS:
            ( A ) LENGTH: 88 base pairs
            ( B ) TYPE: nucleic acid
            ( C ) STRANDEDNESS: single
            ( D ) TOPOLOGY: linear (  i  i  ) MOLECULE TYPE: other nucleic acid
            ( A ) DESCRIPTION: /desc = "LWN8531"

( x i ) SEQUENCE DESCRIPTION: SEQ ID NO: 26:

GACTAAGCTT TGATCAAATG GTTGCGGCCG CGTCGACTCT AGACCCGGGT ACCAGATCTG 60

GATCCTCGGG TTCTTCAAAT ATTTCTCC 88

( 2 ) INFORMATION FOR SEQ ID NO: 27:

( i ) SEQUENCE CHARACTERISTICS:
            ( A ) LENGTH: 39 base pairs
            ( B ) TYPE: nucleic acid
            ( C ) STRANDEDNESS: single
            ( D ) TOPOLOGY: linear (  i  i  ) MOLECULE TYPE: other nucleic acid
            ( A ) DESCRIPTION: /desc = "LWN8518"

( x i ) SEQUENCE DESCRIPTION: SEQ ID NO: 27:

GACTAAGCTT ACGCGTTCGG GTTCTTCAAA TATTTCTCC 39

( 2 ) INFORMATION FOR SEQ ID NO: 28:

( i ) SEQUENCE CHARACTERISTICS:
            ( A ) LENGTH: 44 base pairs
            ( B ) TYPE: nucleic acid
            ( C ) STRANDEDNESS: single
            ( D ) TOPOLOGY: linear (  i  i  ) MOLECULE TYPE: other nucleic acid
            ( A ) DESCRIPTION: /desc = "LWN8527"

( x i ) SEQUENCE DESCRIPTION: SEQ ID NO: 28:

GACTGAATTC TGATCAAATG GTTCAGTGAG AGCGAAGCGA ACAC 44

( 2 ) INFORMATION FOR SEQ ID NO: 29:

( i ) SEQUENCE CHARACTERISTICS:
            ( A ) LENGTH: 17 base pairs
            ( B ) TYPE: nucleic acid
            ( C ) STRANDEDNESS: single (D) TOPOLOGY: linear (ii) MOLECULE TYPE: other nucleic acid
(A) DESCRIPTION: /desc = "LWN7191"

(xi) SEQUENCE DESCRIPTION: SEQ ID NO: 29:

GTTTTCCCAG TCACGAC                                                                                    17

(2) INFORMATION FOR SEQ ID NO: 30:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "LWN8516"

(xi) SEQUENCE DESCRIPTION: SEQ ID NO: 30:

GACTGAATTC GGATCCACGC GTGAGTAGTT CAACAAACGG GCC                                                        43

(2) INFORMATION FOR SEQ ID NO: 31:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "LWN8517"

(xi) SEQUENCE DESCRIPTION: SEQ ID NO: 31:

GACTAAGCTT GAGCTCCAAC ATGATTAACA ATTATTAGAG G                                                          41

(2) INFORMATION FOR SEQ ID NO: 32:

(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "LWN8760"

(xi) SEQUENCE DESCRIPTION: SEQ ID NO: 32:

GACGGAATTC TCTAGAGTCG ACAGATCCGA ACCATTTGAT CATATGACAA GATGTG                                          56

(2) INFORMATION FOR SEQ ID NO: 33:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "LWN8761"

(xi) SEQUENCE DESCRIPTION: SEQ ID NO: 33:

GACGGAATTC GCGGCCGCGG TAAATAGCAA TAAATTGGCC                                                            40

(2) INFORMATION FOR SEQ ID NO: 34:

(i) SEQUENCE CHARACTERISTICS:
(A) LENGTH: 24 base pairs
(B) TYPE: nucleic acid
(C) STRANDEDNESS: single ( D ) TOPOLOGY: linear ( i i ) MOLECULE TYPE: other nucleic acid
    ( A ) DESCRIPTION: /desc = "LWN4123"

( x i ) SEQUENCE DESCRIPTION: SEQ ID NO: 34:

AGCGGATAAC AATTTCACAC AGGA 24

( 2 ) INFORMATION FOR SEQ ID NO: 35:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Tnase1"

( x i ) SEQUENCE DESCRIPTION: SEQ ID NO: 35:

TGACGGATCC ACGCGTGGCG CACTCCCGTT CTGG 34

( 2 ) INFORMATION FOR SEQ ID NO: 36:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Tnase2"

( x i ) SEQUENCE DESCRIPTION: SEQ ID NO: 36:

GTACGGATCC ACGCGTAAAG GCACCTTTGG TCACGG 36

( 2 ) INFORMATION FOR SEQ ID NO: 37:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "LWN8906"

( x i ) SEQUENCE DESCRIPTION: SEQ ID NO: 37:

GGTTTTTCGC ATGTATTGCG 20

( 2 ) INFORMATION FOR SEQ ID NO: 38:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "LWN8907"

( x i ) SEQUENCE DESCRIPTION: SEQ ID NO: 38:

GTTCATTTGA TATGCCTCC 19

DNA INTEGRATION BY TRANSPOSITION

CROSS-REFERENCE TO RELATED APPLICATIONS

This application is a 35 U.S.C. 371 national application of PCT/DK96/00038 filed Jan. 23, 1996 and claims priority under 35 U.S.C. 119 of Danish applications 0083/95 and 0799/95 filed Jan. 23, 1996 and Jul. 6, 1995, respectively, the contents of which are fully incorporated herein by reference.

FIELD OF THE INVENTION

The present invention relates to a novel DNA construct useful for the construction of a bacterial cell having integrated more than one copy of a DNA sequence of interest into its genome, which cell may be free of any selection markers, and a method of constructing such cells.

BACKGROUND OF THE INVENTION

Prokaryotic transposable elements are discrete DNA sequences capable of insertion at single or multiple sites within a prokaryotic genome. Normally, such elements consist of a gene encoding a transposase protein and a transposable cassette comprising a resistance gene flanked by sequences recognized by the transposase protein. Transposition of the transposable cassette into the genome of a host cell (which may, e.g. take place at random or at hot spot sites) occurs via recognition and interaction with the flanking sequences of the transposable cassette by the transposase protein.

Different classes of transposable elements exist. One class comprises i) insertion sequences (IS) which are small (less than 2 kb) DNA fragments encoding transposase proteins or other determinants mediating transposition, and ii) composite transposons, i.e. DNA fragments flanked by two copies of an insertion sequence. The terminal portions of all IS sequences comprises inverted repeat sequences. The transposase protein functions by recognizing these terminal sequences and interacting with the sequences to effect transpositions within the genome.

The second class of transposons is the Tn3 family of tranposons. These transposons encode two products involved in a two-step transposition process: a transposase and a resolvase.

Transposons belonging to this second class have inverted terminal repeats of approximately 35–40 bp.

The third class includes bacteriophage Mu and related phages. Bacteriophage Mu is large relative to other transposons with a genome of 36 kb. Mu encodes two gene products which are involved in the transposition process, a 70 kDa transposase and an accessory protein of approximately 33 kDa. An unusual feature of Mu that distinguishes it from other tranposons is that its ends are not inverted repeat sequences. The Mu transposase has, however, been shown to bind to both ends in an in vitro binding assay.

Transposons have been used extensively for mutagenesis and cloning in gram-positive and gram-negative bacteria: Youngman, P. J., Perkins, J. B., Losick, R. (1983) Genetic transposition and insertional mutagenesis in *Bacillus subtilis* with *Streptococcus faecalis* transposon Tn917, Proc. Natl. Acad. Sci. USA, 80, 2305–2309; Youngman, P., Perkins, J. B., Losick, R. (1984), Construction of a cloning site near one end of Tn917 into which foreign DNA may be inserted without affecting transposition in *Bacillus subtilis* or expression of the transposon-borne erm gene, Plasmid 12, 1–9; Youngman, P. (1985) Plasmid vectors for recovering and expoliting Tn917 transpositions in *Bacillus subtilis* and other gram positives, p. 79–103 in K. Hardy (ed.), Plasmids: a practical approach, IRL Press, Oxford; Kleckner, N., Roth, J., Botstein, D. (1977) Genetic engineering in vivo using translocatable drug-resistance elements. New methods in bacterial genetics, J. Mol. Biol., 116, 125–159; Wati, M. R., Priest, F. G., Mitchell, W. J. (1990) Mutagenesis using Tn917 in *Bacillus licheniformis*. FEMS microbiol. Lett., 71, 211–214; Petit, M.-A., Bruand, C., Janniere, L., Ehrlich, S. D. (1990) Tn10-derived transposons active in *Bacillus subtilis*. J. Bacteriol., 172, 6736–6740.

The latter reference describes pHV1248 and pHV1249, plasmids that are thermosensitive for replication, which carry a transposase gene from Tn10 modified to be expressed in *B. subtilis*, and sufficient sequences from the IS10 elements of Tn10 flanking a chloramphenicol resistance gene (mini-Tn10) to allow transposition of mini-Tn10 into the *B. subtilis* chromosome.

Maguin et al. (Maguin, E., Duwat, P., Hege, T., Ehrlich, D, Gruss, A. (1992) New thermosensitive plasmid for gram-positive bacteria, J. Bacteriol. 174, 5633–5638) describe an alternative version of this system.

EP 485 701 discloses the use of transposons for introduction of single copies of a DNA sequence into a prokaryotic cell genome, the transposase protein being encoded in cis.

Slugenova et al., ((1993), Enhanced α-amylase production by chromosomal integrtation of PTVA1 in industrial strain in *B. subtilis*, Biotechnology Letters, 15, 483–488) describe the multiple integration of plasmid pTVA1 comprising a modified transposon Tn917 and an α-amylase gene of interest located outside the transposon. Antibiotic resistance marker genes are present in the resulting strain.

EP 0 332 488 describes a transposition based system for construction of multicopy bacterial strains, i.e. strains comprising multiple copies of a gene of interest, which strains further comprise multiple copies of a selectable marker gene introduced with the gene of interest. The system is exemplified by use of a phage Mu transposon for modification of gramnegative bacteria.

WO 95/01095 describes the use of a minitransposon as a vector for stably tranforming an exogenous gene into a eukaryotic (e.g. animal) chromosome.

Simon, R., Priefer, U., Pühler, A. ((1983), A broad host range mobilization system for in vivo genetic enginering: Transposon mutagenesis in gram-negative bacteria, Bio/Technology, 1, 784–791) describe the use of *E. coli* specific vectors to transfer transposons into other gram-negative strains by conjugation.

Several of the above described multicopy strains have been produced by integration of a genetic construct comprising the gene of interest and an antibiotic selectable marker and amplifying said construct by culturing the cell in the presence of increasing dosages of antibiotic. Thus, the resulting cell typically comprises a number of antibiotic resistance genes. The presence of such genes are undesirable, in particular from an environmental and a product approval point of view.

Non-antibiotic selection markers have been used for construction of multicopy strains. Herrero, M., de Lorenzo, V., Timmis, K. N. ((1990), Transposon vectors containing non-antibiotic resistance selection markers for cloning and stable chromosomal insertion of foreign genes in gram-negative bacteria, J. Bacteriol., 172, 6557–6567) describe such as system in which herbicide or heavy metal resistances are used as selection markers.

Another alternative to the use of antibiotic resistance markers are described in DE 4 231 764 in which an alternating selection of Thy⁻ (trimethoprim resistance) and Thy⁺ (thy prototrophy) is used for introduction of product genes in *Bacillus spp.* thereby avoiding the need for selectable markers.

Specific deletion of DNA segments from the chromosomes of bacterial species have traditionally been performed by the methods of homologous recombination (Hamilton, C. H., Aldea, M., Washburn, B. K., Babitzke, P. (1989). New method of generating deletions and gene replacement in *Escherichia coli*. J. Bacteriol., 171, 4617–4622.; Maguin, E., Duwat, P., Hege, T., Ehrlich, D, Gruss, A. (1992). New thermosensitive plasmid for gram-positive bacteria. J. Bacteriol. 174, 5633–5638.). However, the use of homologous recombination to delete resistance marker genes from strains having multiple, tandem copies of such genes each linked to a copy of the gene of interest is hardly applicable, as homologous recombination would delete also the extra copies of the gene of interest.

The concept of using site specific recombination systems for integration and retrieval of sequences from the bacterial chromosome, using elements from either phage lambda or P1, and some specific methods of achieving this, has been described (Hasan, N., Koob, M., Szybalski, W. (1994), *Escherichia coli* genome targeting, I. Cre-lox-mediated in vitro generation of ori⁻ plasmids and their in vivo chromosomal integration and retrieval. Gene, 150, 51–56). The cre-lox system is further described by Abremski, K., Hoess, R., Sternberg, N. (1983), Studies on the properties of P1 site-specific recombination: Evidence for topologically unlinked products following recombination, Cell, 32, 1301–1311. An alternative system is based on the recombination system of the broad-host range plasmid RP4 (Eberl, L., Kristensen, C. S., Givskov, M., Grohmann, E., Gerlitz, M., Schwab, H. (1994), Analysis of the multimer resolution system encoded by the parCBA operon of broad-host-range plasmid RP4, Mol. Microbiol., 12, 131–141)). Stark, W. M., Boocock, M. R., Sherratt, D. J. (1992), Catalysis by site-specific recombinases, Trends in Genetics, 8, 432–439) is a review article on the mechanism of resolvase action. Camilli et al. ((1994), Use of genetic recombination as a reporter of gene expression, Proc. Natl. Acad. Sci. USA, 91, 2634–2638) describe the use of res sites and resolvase from the γδ transposon in *Vibrio cholera* as a permanent, heritable marker of gene expression from a chromosomal gene. The resolution system is not used for excision of marker genes. Chang, L.-K. et al. ((1994, Construction of Tn917as1, a transposon useful for mutagenesis and cloning of *Bacillus subtilis* genes, Gene, 150, 129–134) describe the plasmids (pE194) containing erm-res-tnpA (transposase)-tnpR (resolvase) samt IR-res-ori colE1-AB$^R$1-AB$^R$2-IR (pD917; Tn917ac1). The two res sites are there to allow the transposon to function properly, not for excision of intervening DNA.

The broad host range, gram-positive plasmid pAMβ1 (Clewell, D. B., Yagi, Y., Dunny, G. M., Schultz, S. K. (1974) Characterization of three plasmid deoxyribonucleic acid molecules in a strain of *Streptococcus faecalis*: identification of a plasmid determining erythromycin resistance. J. Bacteriol. 117, 283–289) has been described to contain a resolution system, that resolves plasmid multimers into monomers via a site specific recombination event, requiring a specific plasmid encoded enzyme (resolvase) and a site, res, on the plasmid (Swinfield, T.-J., Janniere, L., Ehrlich, S. D., Minton, N. P. (1991). Characterization of a region of the Enterococcus faecalis plasmid pAMβ1 which enhances the segregational stability of pAMβ1-derived cloning vectors in *Bacillus subtilis*. Plasmid 26, 209–221; Janniere, L., Gruss, A., Ehrlich, S. D. (1993) Plasmids, pp. 625–644 in Sonenshein, A. L., Hoch, J. A., Losick, R. (eds.) *Bacillus subtilis* and other gram-positive bacteria: Biochemistry, Physiology and molecular genetics. American society for microbiology, Washington D.C.).

It has been suggested to use a site-specific recombination system to remove a single selectable marker gene from the genome of a bacterial cell. For instance, Dale, et al. ((1991) Gene transfer with subsequent removal of the selection gene from the host genome, Proc. Natl. Acad. Sci. USA, 88, 10558–10562) describe the use of the cre/lox system for removal of markers from transgenic plants and mentions that the use of this system would obviate the need for different selectable markers in subsequent rounds of gene tranfer into the same host. Kristensen, C. S. et al. (1995), J. Bacteriol., 177, 52–58, describe the use of the multimer resolution system of the plasmid RP4 for the precise excision of chromosomal segments (such as marker genes introduced with heterologous DNA) from gram-negative bacteria. It is stated that the system is envisaged to be of interest in the generation of chromosomal insertions of heterologous DNA segments eventually devoid of any selection marker.

WO 95/02058 describes a new transposon (tn5401) from *B. thuringiensis* containing transposase, resolvase, and res site. The transposon is used in a plasmid which contains *B. thuringiensis* DNA (e.g. origin and toxin gene) and, flanked by res sites, non-*B. thuringiensis* DNA (e.g. *E. coli* origin, selectable marker genes). The plasmid is introduced into *B. thuringiensis*. Subsequently, a plasmid expressing the resolvase is introduced (e.g. a thermosensitive plasmid containing the entire tranposons—but only used as resolvase donor) whereby the non-*B. thuringiensis* DNA is excised from the first plasmid.

Conclusions With Respect to the State of the Art

On the basis of the above citations, the following conclusions may be made as to the state of the art:

The insertion of multiple genes of interest by transposition was known, e.g. as described in EP 332 488. However, all strains carrying multiple transposed sequences of interest contain selectable markers.

The removal of markers via site-specific recombination was know from either chromosome or plasmids (cf. Kristensen et al. (1995), Eberl et al. (1994), WO 95/02058). It was known to remove a marker introduced by transposon.

Multicopy strains without presence of heterologous, selectable marker genes were known (DE 4231 764). These strains were constructed by a cumbersome method depending on the use of the Thy marker.

It is an object of the present invention to construct bacterial cells which harbour a stable, fixed and well-defined copy number of one or more genes of interest, without the presence of selectable marker genes in the final strain.

BRIEF DESCRIPTION OF THE INVENTION

The present invention is based on the surprising finding that transposition of a DNA construct which, in addition to transposase target sequences and the transposase gene necessary to achieve transposition, contains target sequences for a site-specific recombination enzyme, may be used for construction of multicopy gram-positive bacterial strains.

In a first aspect the invention relates to a DNA construct useful for integration into the genome of a host cell, the construct comprising the structure IR(1)-P-R-M2-R-IR(2) or IR(1)-R-M2-R-P-IR(2), wherein IR(1) and IR(2) denote transposase target sequences, P a DNA fragment comprising a DNA sequence of interest, R a target sequence for a site-specific recombination enzyme, and M2 a selectable marker gene, the structure being associated with a gene (T) encoding a transposase protein capable of recognizing and interacting with the transposase target sequences IR(1) and IR(2) and located outside the structure defined by the IR(1) and IR(2) sequences.

In the present context the term "associated with" is intended to indicate that T is present on the DNA construct of the invention, but need not be in direct contact with the structure defined by IR(1) and IR(2), i.e. located within and comprising IR(1) and IR(2). Thus, linker or other sequences may be present in between the structure and T. The exact location of T is not critical as long as the gene is located outside the structure defined by IR(1) and IR(2). Thus, T may be located on either side of the structure defined by IR(1) and IR(2).

In the present context the term "selectable marker gene" is intended to indicate a DNA sequence which encodes a gene product which provides to the host cell expressing the product a selectable characteristic, such as resistance towards an antibiotic. The DNA sequence M2 may further comprise one or more regulatory elements required for or involved in the expression of the DNA sequence encoding the selectable marker, such as a promoter, a terminator and the like. The regulatory elements may be either heterologous or homologous to the DNA sequence.

The term "transposase gene" is intended to indicate a DNA sequence encoding a transposase protein, i.e. a protein which is essential for transposition to take place. The gene may further comprise one or more regulatory elements required for or involved in the expression of the DNA sequence encoding the transposase protein, such as a promoter, a terminator and the like. The regulatory element (s) may be either heterologous or homologous to the DNA sequence.

The term "transposase target sequence" is intended to indicate DNA sequences recognized by the transposase protein encoded by the transposase gene T. The transposase target sequences IR(1) and IR(2) shall contain sufficient DNA derived from transposon terminal sequences to retain the function of these sequences in allowing transposition of the structure comprising and located within these sequences upon expression of the transposase encoded by T. The minimal sequences that are sufficient for transposition vary in composition and length depending on which transposon the system is developed from. For instance, for Tn10 derived transposase target sequences, either 23 or 42 basepairs are enough to allow transposition (Kleckner, N. (1988) Transposon Tn10. pp 227–268 in Berg, D. E., and Howe, M. M. (eds). Mobile DNA. American society for microbiology, Washington, D.C.).

In the present context the "target sequence for a site-specific recombination enzyme" is intended to indicate a DNA sequence which is recognized by a site-specific recombinase enzyme (discussed in detail further below). The target sequences may be, but need not be identical. Thus, variations between the sequences may occur as long as the recombinase is capable of recognizing and interacting with the sequences.

The term "DNA sequence of interest" is used to indicate a sequence which codes for a desired RNA or protein product (heterologous or native to the host cell) or which in itself provides the host cell with a desired property, e.g. a mutant phenotype. When appropriate, the DNA sequence may also comprise one or more regulatory elements required for or involved in the expression of the DNA sequence encoding the desired RNA or protein product, such as a promoter, a terminator and the like. The regulatory element (s) may be either heterologous or homologous to the DNA sequence.

The novel DNA construct of the invention has been found of particular use in construction of strains which in their genome comprise more than one, and preferably multiple, randomly located copies of integrated DNA sequences, which cells in preferred aspects are free from genes encoding a selectable marker the presence of which is undesirable, e.g., from an environmental point of view. It will be noted that the DNA construct of the invention is different from those provided in EP 485 701 in that the selectable marker gene in the present invention is located outside the structure flanked by transposase target sequences. This location is essential for constructing marker-free cells in accordance with the present invention.

An alternative approach to using the above described recombinase system for deleting a marker gene used in the construction of modified cells by transposition is to effect the deletion of the marker gene by homologous recombination. Accordingly, in a second aspect of the present invention relates to a DNA construct is provided which comprises the structure IR(1)-P-R'-M2-R"-IR(2) or IR(1)-R'-M2-R"-P-IR(2), wherein IR(1) and IR(2) denote transposase target sequences, P a DNA fragment comprising a DNA sequence of interest, R' and R", respectively, a DNA sequence which is provided in a parallel repeat on either side of the selectable marker gene M2, and M2 a selectable marker gene, the structure being associated with a gene (T) encoding a transposase protein capable of recognizing and interacting with the transposase target sequences IR(1) and IR(2) and located outside the structure defined by the IR(1) and IR(2) sequences, i.e. outside the structure IR(1)-P-R'-M2-R"-IR(2) or IR(1)-R'-M2-R"-P-IR(2).

The term "provided in a parallel repeat" is intended to indicate that the DNA sequences R' and R" flanking M2 are sufficiently homologous to allow for homologous recombination to take place between the sequences. Preferably, each of the sequences R' and R" comprises a substantially identical segment of at least 20 nucleotides, more preferably of at least 50 nucleotides, such as 50–100 nucleotides, and even more preferably at least 500 (such as 500–1000 nucleotides) and most preferably at least 1000 nucleotides, such as 1000–3000 nucleotides.

The presence of the target sequences for a site-specific recombination enzyme (first aspect) or of the parallel repeats (second aspect) enables the specific deletion of the marker gene M2 from the genome of a host cell which in its genome have received the marker gene by transposition. More specifically, the DNA constructs according to the first and second aspect of the invention, respecitively, in which the marker gene M2 is located in between target sequences for a site-specific recombination enzyme or in between parallel repeat sequences, is particularly useful for the construction of marker-free, multicopy strains (i.e. bacterial cells which in their genome comprise multiple copies of an integrated DNA sequence of interest). In short each of the DNA constructs is intended to be used in a two-step integration process, wherein, in the first step, genomic integration of the fragment IR(1)-P-R-M2-R-IR(2) or IR(1)-R-M2-R-P-IR(2) (the first aspect), or IR(1)-P-R'-M2-R"-IR(2) or IR(1)-R'-M2-R"-P-IR(2) (the second aspect), is accomplished by transposition and selection for M2$^+$-cells, and, in the second step, the selectable marker gene M2 is eliminated by a site-specific recombinase enzyme provided in trans and interacting with the target sequences R flanking the marker gene M2 (the first aspect) or by recombination between the parallel repeat sequences R' and R" (the second aspect).

In the present context the term "marker-free" is intended to indicate that the cell having integrated multiple copies of a DNA sequence of interest does not express a selectable marker, such as an antibiotic resistance, the presence of which is undesired in the cell, which marker is necessary for or advantageously used in the construction of the cell.

DETAILED DESCRIPTION OF THE INVENTION

In the following the various aspects of the invention is discussed in further detail.

The DNA Construct of the Invention

In addition to the DNA constructs according to the first and second aspect of the invention, which are described above, in a third aspect, the present invention relates to a DNA construct comprising the structure IR(1)-R-M2-T-R-P-IR(2), IR(1)-P-R-M2-T-R-IR(2), IR(1)-R-T-M2-R-P-IR(2) or IR(1)-P-R-T-M2-R-IR(2), wherein IR(1) and IR(2) denote transposase target sequences, P a DNA sequence of interest, R a target sequence for a site-specific recombination enzyme, M2 a selectable marker gene, and T a transposase gene T.

As compared to the DNA construct according to the first aspect of the invention the DNA construct of the third aspect comprises the transposase gene T inside the structure defined by IR(1) and IR(2) rather than outside said structure.

Analogously, in a fourth aspect the invention relates to a DNA construct comprising the structure IR(1)-R'-M2-T-R"-P-IR(2), IR(1)-P-R'-M2-T-R"-IR(2), IR(1)-R'-T-M2-R"-P-IR(2) or IR(1)-P-R'-T-M2-R"-IR(2), wherein IR(1) and IR(2) denote transposase target sequences, P a DNA sequence of interest, R' and R" parallel repeat sequences, M2 a selectable marker gene, and T a transposase gene T.

The DNA construct of the invention is preferably one, which is capable of being transposed in cells of gram-positive bacteria, in particular strains of Bacillus.

Selectable Marker

In order to facilitate selection for cells in which the part of the DNA construct of the invention located within and comprising the inverted repeat sequences IR(1) and IR(2) (e.g. the structure IR(1)-P-R-M2-R-IR(2) or IR(1)-R-M2-R-P-IR(2) in connection with the first aspect of the invention) has been integrated in the genome, it is advantageous that the DNA construct comprises a further selectable marker gene M1 outside the structure defined by and comprising IR(1) and IR(2). In this case, the DNA construct comprises a first selectable marker gene M1 present outside the structure defined by and comprising IR(1) and IR(2) and a second marker M2 within said structure. Thereby, when M1 is different from M2, it is possible to make a two step selection when the DNA construct of the invention is transposed into the genome of a recipient cell, the first step selecting for cells in which the DNA construct has been introduced (M1$^+$, M2$^+$ cells) and a second step selecting for cells in which the structure defined by IR(1) and IR(2) comprising the marker gene M2 has been integrated into the genome and the remaining part of the DNA construct (carrying M1) has been lost (M1$^-$, M2$^+$). Subsequently, the marker gene M2 may be eliminated from the resulting cells by the action of a resolvase protein.

The selectable marker may be a gene coding for a product which confers antibiotic resistance to a cell expressing the gene or a non-antibiotic marker gene, such as a gene relieving other types of growth inhibition, i.e. a marker gene which allow cells containing the gene to grow under otherwise growth-inhibitory conditions. Examples of such genes include a gene which confers prototrophy to an auxotrophic strain, e.g. dal genes introduced in a dal$^-$ strain (cf. B. Diderichsen in *Bacillus: Molecular Genetics and Biotechnology Applications*, A. T. Ganesan and J. A. Hoch, Eds., Academic Press, 1986, pp. 35–46) or a thy gene introduced in a thy$^-$-cell (cf. Gryczan and Dubnau (1982), Gene, 20, 459–469) or a gene which enables a cell harbouring the gene to grow under specific conditions such as an amdS gene, the expression of which enables a cell harbouring the gene to grow on acetamide as the only nitrogen or carbon source (e.g. as described in EP 635 574), or a gene which confers resistance towards a heavy metal (e.g. arsenite, arsenate, antimony, cadmium or organo-mercurial compounds) to a cell expressing the gene. Cells surviving under these conditions will either be cells containing the introduced DNA construct in an extrachromosomal state or cells in which the above structure has been integrated. Alternatively, the selectable marker gene may be one conferring immunity to a cell expressing the gene.

The DNA Sequence of Interest

The DNA sequence of interest present in the DNA construct of the invention may be a DNA sequence having or encoding any function. For instance, the DNA sequence may comprise a sequence encoding a structural or regulatory protein, or may comprise a regulatory sequence such as a promoter. Alternatively, the inserted sequence may be one not known to possess any biological function, which can be used to interrupt a cellular function, e.g. by inserting itself within an essential gene thereby interrupting the function of the gene. The DNA sequence of interest may be a gene and thus associated with the necessary regulatory elements required for its expression including a promoter, a terminator or a ribosome binding site.

As will be understood from the above the present invention is of particular use in constructing bacterial cells comprising multiple copies of a DNA sequence of interest. Such multicopy strains are of particular interest for the industrial production of polypeptides of interest and, accordingly, in a highly preferred embodiment the DNA sequence of interest encodes a polypeptide of interest.

The polypeptide may be a translocated polypeptide, i.e. a polypeptide which, when expressed, carries a signal sequence which enables it to be translocated across the cell membrane. In particular, the translocated polypeptide may be a secreted polypeptide or a polypeptide involved in the secretory machinery of the bacterial cell in question.

The polypeptide, whether secreted or not, may be an enzyme, e.g., selected from an amylolytic enzyme, a lipolytic enzyme, a proteolytic enzyme, a cellulytic enzyme, an oxidoreductase or a plant cell-wall degrading enzyme. Examples of such enzymes include AMG, amylase, lipase, cutinase, esterase, cellulase, hemicellulase, protease, peroxidase, laccase, phenoloxidase, catalase, glucose oxidase, phytase, lyase, pectinase, glucosidase, mannosidase, isomerase, invertase, trasferase, ribonuclease, galactosidase and chitinase. Alternatively, the secreted polypeptide may be a hormone, a growth factor, a receptor or the like.

A preferred example of a translocated polypeptide of the secretory pathway is PrsA (WO 94/19471) which, when overexpressed in cells of Bacillus, has been found to result in an increased secretion of a secreted polypeptide of interest from such cells.

Transposase and Transposase Recognition Sequences

It will be understood that the transposase gene and the transposase target sequences must be chosen so as to be capable of functioning together. In the present invention any transposase recognition sequence may be used together with the corresponding transposase. Typically, the transposase gene and the transposase target sequences are derived from the same class of transposons (cf the Background of the Invention section above), and preferably from the same transposon. The transposase recognition sequences may be inverted repeat sequences, e.g. derived from Tn1, Tn2, Tn3, Tn5, Tn9, Tn10 and Tn903.

Alternatively, the transposase recognition sequences are free from inverted repeats. Examples of such sequences are those derived from the transposase recognition sequences of bacteriophage Mu and related transposons. When the transposase recognition sequences are derived from bacteriophage Mu it may be necessary to supply an accessory protein in addition to the transposase (cf the Background of the Invention section above).

The transposase gene and the transposase target sequences may be derived from naturally occurring transposons either by being isolated from the relevant source by use of standard techniques or by being synthesized on the basis of known sequences. It will be understood that functional analogues or derivatives of naturally occurring sequences may be used as long as they are capable of mediating the transposition. The functional analogues or derivatives may be prepared synthetically and may differ from the wild type sequence in one or more nucleotides.

Resolvase and Resolvase Target Sequences

It will be understood that the essential feature according to the second aspect of the invention is the use of a sitespecific recombination system to specifically delete the marker gene M2, once transposition into the host genome has taken place. Several site-specific recombination systems are known (cf the Background of the Invention section above) all of which are contemplated to be useful for use in the present invention. For the purpose of the present invention, the preferred use is of a system which consists of only two elements: a site specific recombinase enzyme and a target sequence for said enzyme.

Examples of such systems are the pAMβ1 resolvase having as target sequence the pAMβ1 res sequence (Janniere, L., Gruss, A., Ehrlich, S. D. (1993), Plasmids, pp. 625–644 in Sonenshein, A. L., Hoch, J. A., Losick, R. (eds.) *Bacillus subtilis* and other gram-positive bacteria: Biochemistry, Physiology and molecular genetics, American society for microbiology, Washington, D.C.) and the phage P1 Cre enzyme having as target sequence the P1 lox site (Hasan, N., Koob, M., Szybalski, W. (1994). *Escherichia coli* genome targeting, I. Cre-lox-mediated in vitro generation of ori⁻ plasmids and their in vivo chromosomal integration and retrieval, Gene, 150, 51–56).

It will be understood that the DNA sequence encoding the recombinase enzyme and the target sequence for this enzyme may be derived from naturally occurring systems (as described above) either by being isolated from the relevant source by use of standard techniques or by being synthesized on the basis of known sequences. It will be understood that functional analogues or derivatives of naturally occurring sequences may be used as long as they are capable of functioning in the intended manner. The functional analogues or derivatives may be prepared synthetically and may differ from the wild type sequence in one or more nucleotides.

For some purposes it may be advantageous to introduce the gene encoding the recombinase enzyme (when provided in trans) into the cell by use of a naturally occurring plasmid, such as pAMβ1, comprising the gene.

The DNA sequence encoding the recombinase enzyme is preferably provided in trans. However, it may be advantageous that the DNA sequence is present in the vector which carries the DNA construct of the invention. In this case the DNA sequence is preferably located in the part of the vector which is integrated into the genome of the host cell, and most preferably on the part of the DNA which after integration is excised from the genome due to the action of the recombinase enzyme. In addition, the DNA sequence should be located under the control of an inducible or regutable promoter such as a temperature inducible promoter or a xylose inducible promoter or the SPAC promoter, so that the expression from the DNA sequence could be controlled to take place only after transposition has taken place. If the DNA sequence encoding the recombinase enzyme is provided in cis and under the control of a regutable promoter the method of the invention may be accomplished using only one transformation step.

Furthermore, the gene encoding the site specific recombination enzyme may be engineered by methods well known in the art to allow its proper expression in the host strain. It may by transferred onto a temperature-sensitive or otherwise conditional replicon, to allow for easy loss of the gene from the host cell once the site-specific recombination event has occurred.

Homologous Recombination in Combination with a Counterselec-table Marker

Although the selectable marker gene may be deleted by homologous recombination between the DNA sequences R' and R" when using the DNA construct according to the second aspect of the invention such homologous recombination may occur with a very low frequency for which screening may be difficult to achieve in actual practice. In order to avoid this practical problem, it may be advantageous that the selectable marker gene M2 is a gene which in the host cell of choice can be counterselected. In other words, it may be desirable to use a marker, the presence as well as the absence of which can be selected. For instance, the marker gene may be one conferring prototrophy to an auxotrophic cell, e.g. a thy gene for use in a thy⁻-cell (Gryczan, T. J., and Dubnau, D. (1982), Direct selection of recombinant plasmids in *Bacillus subtilis*, Gene, 20, 459–469), or a gene which enables a cell expressing the gene to grow on a specific substrate, e.g. amdS, the expression of which allows cells to grow on acetamide as the only nitrogen or carbon source (EP 635 574). When the thy gene is used a selectable marker M2 the DNA construct according to the second aspect is introduced into a thy⁻-cell allowing for selection of cells having received the construct (first step) and in a second step the resulting cells are subjected to growth on a medium which cannot tolerate the presence of the thy gene, thereby allowing for selection of cells having lost the thy gene by homologous recombination (the principle of using a thy gene as a counterselectable marker is described in detail by Gryczan and Dubnau op. cit.).

Analogously, the amdS gene may be used in a two step procedure, wherein in a first step selection is made for amdS-containing cells by growth on acetamide as the only carbon or nitrogen source, and in a second step counterselection is made by growing the cells on a medium containing flouracetamide and urea as nitrogen sources (cf EP 635 574) whereby cells are selected which do not contain the amdS gene.

Construction of the DNA Construct of the Invention

A DNA construct of the invention may conveniently be constructed on the basis of naturally occurring or otherwise existing transposon delivery vectors. The transposon delivery vectors described in the literature contains a transposase gene, if needed modified so as to be expressed in the intended host organism, and a transposable cassette, essentially containing a resistance gene flanked by sufficient DNA derived from the ends (e.g. inverted repeat sequences) of the original transposon to enable the transposition of the resistance gene into the host genome.

In one embodiment the DNA construct of the invention may be prepared by modification of such transposon delivery vectors so as to contain, within the structure that by transposition integrates into the host genome, a DNA sequence of interest, either replacing or in addition to the antibiotic resistance gene. It is further possible to replace the antibiotic resistance gene with any other selectable marker gene. The modification of the transposon delivery vectors may be accomplished by methods known in the art. In an alternative embodiment the DNA construct of the invention is prepared by joining each of the isolated elements to be comprised by the DNA construct using methods known in the art.

When the selectable marker gene is to be eliminated from the cells in which the DNA construct has been integrated the marker should be flanked by resolvase target sequences or by parallelly repeated homologous DNA sequences. These sequences may be inserted into the DNA construct prepared as described above by methods known in the art. It is important that the gene of interest is located outside the structure flanked by these target sequences.

The Vector of the Invention

Origin of Replication

For use in the present invention it is generally preferred that the DNA construct of the invention is linked to an origin of replication, i.e. present on a vector. In the present context the term "vector" is intended to denote a DNA molecule capable of functioning as an autonomously replicating extra-chromosomal element. The vector may, e.g., be a plasmid or a bacteriophage.

The origin of replication should not be located between the transposase recognition sequences IR(1) and IR(2) since such location would result in the origin of replication being integrated into the genome of the host cell. Genomic integration of an origin of replication is undesirable from a stability point of view.

Except for the above the location of the origin of replication is not critical. Thus, in a DNA construct of the invention the origin of replication may be located on either side of "T" and "M1" (when present).

If it is desired to improve the efficiency with which cells harbouring an integrated DNA construct can be isolated, the DNA construct may be present on a vector comprising a conditional origin of replication. In other words a vector may be used which is able to replicate under certain (permissive) conditions and unable to replicate under other (non-permissive) conditions. The vector may, for instance, be one which is temperature-sensitive for replication. Thus, in an embodiment of the method of the invention, the vector comprising the DNA construct to be integrated is one which is unable to replicate at increased temperatures, which yet permit growth of the host cell. The bacterial cells are initially cultured at a temperature permitting vector replication and subsequently, after integration of the DNA construct of the invention, into the bacterial genome may have taken place, cultured at a temperature which does not permit vector replication so that the vector introduced into the cell is lost from the cells. The cultivation at the non-permissive temperature is conducted under selective conditions to ensure that only cells containing the integrated DNA construct will survive.

Another way of increasing the efficiency of integration and subsequent loss of the vector from the cells may be to treat the cells transformed with the vector with a plasmid-curing agent, e.g. novobiocin (Gadó, I. et al., 1987. Zbl. Bakt. Hyg. A. 265, 136–145), after culturing the host cells under selective conditions as described above.

A still further type of a conditional replication origin may be one of a limited host-range plasmid, i.e. a plasmid which can only replicate in a limited number of microbial species. For the present purpose an origin of replication should be chosen which is derived from a limited host-range plasmid which is unable to replicate in the recipient cell into which the DNA construct is to be transposed.

When the DNA construct of the invention is constructed by modification of transposon delivery vectors the origin of replication normally present on these vectors may be used. Otherwise, the origin of replication may be provided, conveniently by inserting the DNA construct into a vector suitable for the introduction into the intended host cell. The integration of the transposable cassette into the genome of the host cell may be accomplished following the procedures described in the literature (Petit et al., 1990 op. cit.) for use of transposon delivery vectors for mutagenesis.

Cis-acting Conjugational Elements

It may be desirable to introduce the vector of the invention carrying a DNA construct of the invention into the recipient cell in question by means of conjugation (further described in the section below entitled "Construction of single or multicopy, optionally marker-free strains"). For this purpose the DNA construct or vector comprises a so-called cis-acting DNA sequence which is required for conjugation to take place.

Accordingly, when a vector carrying a DNA construct of the invention is to be introduced into a recipient cell by conjugation the DNA construct or vector further comprises a cis-acting DNA sequence required for transfer of a plasmid comprising the DNA construct.

The cis-acting DNA sequence may conveniently be any DNA sequence or DNA site capable of mediating mobilization, a preferred example being oriT of the tetracycline resistance plasmid pBC16 or of the *Staphylococcus aureus* kanamycin resistance plasmid pUB110 (as described by Sellinger et al., Journal of Bacteriology, June 1990, pp. 3290–3297) or a functional analogue or part of oriT.

For all types of vectors carrying a DNA construct of the invention (harbouring any of the structures as defined in connection with the first, second, third and fourth aspect of the invention) the cis-acting sequence may be located on the vector, but outside the structure defined by and comprising IR(1) and IR(2),whereby the sequence will be excised together with the transposon delivery vector. Thus, the cis-acting DNA sequence may be located on either side of said structure and of the DNA sequence T and the DNA sequence M1, when present.

In an preferred embodiment of the first, second, third and fourth aspect of the invention, the cis-acting sequence is located in the part of the structure located within and comprising the resolvase target sequences R and the parallel repeat sequences R' and R", respectively. Thereby, the cis-acting sequence may be excised—together with the selectable marker gene M2 and optionally T (second and fourth aspect of the invention)—from the genome of the cell in which the DNA structure has been integrated.

Construction of Single or Multicopy, Optionally Marker-free Strains

As it will be understood the construction of multicopy, marker-free production strains may be achieved by use of the above described DNA constructs allowing the stepwise integration of one or more copies of a DNA sequence of interest into the genome of a bacterial cell, which method comprises repeated steps of transposition followed by site-specific marker deletion.

Accordingly, in further aspects the invention relates to methods of constructing a bacterial cell of the invention by use of the DNA construct according to the first, second, third and fourth aspect, respectively, as further defined above.

Accordingly, in a further aspect the invention relates to a method of constructing a bacterial cell, which in its genomic DNA has integrated more than one copy of a DNA sequence of interest, and which is free from a DNA sequence encoding an undesired selectable marker, which method comprises a) introducing a first vector comprising a DNA construct according to the first aspect of the invention comprising the structure IR(1)-P-R-M2-R-IR(2) or IR(1)-R-M2-R-P-IR(2) in association with a tranposase gene T and optionally a selectable marker gene M1 into the host cell, in which R denotes a target sequence for a site-specific recombination enzyme, b) selecting for cells being M2$^+$ and optionally M1-, which in their genome comprises the structure IR(1)-P-R-M2-R-IR(2) or IR(1)-R-M2-R-P-IR(2), c) introducing a second vector comprising a DNA sequence encoding a site specific recombinase into the cells selected in step b) so as to excise the structure R-M2 or M2-R from the genome of the cell whereby cells are obtained having integrated the structure IR(1)-R-P-IR(2) or IR(1)-P-R-IR(2), d) curing the cells resulting from step c) for the second plasmid, and optionally e) repeating steps a–d) one or more times to produce bacterial cells comprising one or more additional copies of the structure IR(1)-R-P-IR(2) or IR(1)-P-R-IR (2).

In a still further aspect the invention relates to a method of constructing a bacterial cell, which in its genomic DNA has integrated more than one copy of a DNA sequence of interest, and which is free from a DNA sequence encoding an undesired selectable marker, which method comprises a) introducing a first vector comprising a DNA construct according to the third aspect of the invention comprising the structure IR(1)-R-M2-T-R-P-IR(2), IR(1)-P-R-M2-T-R-IR(2), IR(1)-R-T-M2-R-P-IR(2) or IR(1)-P-R-T-M2-R-IR(2) optionally in association with a selectable marker gene M1 into the host cell, b) selecting for cells being M1$^-$ (if M1 was present on the vector) and M2$^+$, which cells in their genome comprises one of the structures identified in a), c) selecting for cells having an increased number of copies of the marker gene M2, d) introducing a second vector comprising a DNA sequence encoding a site specific recombinase into the cells selected in step b) so as to excise the structure R-M2-T, R-T-M2, M2-T-R or T-R-M2 from the genome of the cell whereby cells are obtained having integrated the structure IR(1)-R-P-IR(2) or IR(1)-P-R-IR(2), e) curing the cells resulting from step d) f or the second plasmid, and optionally f) repeating steps a–e one or more times to produce bacterial cells comprising one or more additional copies of the structure IR(1)-R-P-IR(2) or IR(1)-P-R-IR (2).

In a still further aspect the invention relates to a method for constructing a bacterial cell, which in its genomic DNA has integrated more than one copy of a DNA sequence of interest, and which is free from a DNA sequence encoding an undesired selectable marker, which method comprises a) introducing a first vector comprising a DNA construct according to the second aspect of the invention comprising the structure IR(1)-P-R'-M2-R"-IR(2) or IR(1)-R'-M2-R"-P-IR(2) in association with a tranposase gene T and optionally a selectable marker gene M1 into the host cell, in which R' and R" denote parallel repeat sequences, b) selecting for cells being M1$^-$ (if M1 was present on the vector) and M2$^+$, which cells in their genome comprises the structure IR(1)-P-R'-M2-R"-IR(2) or IR(1)-R'-M2-R"-P-IR(2), c) allowing homologous recombination between the DNA sequences R' and R" to take place so as to excise the selectable marker gene M2, whereby cells are obtained having integrated the structure IR (1)-R'/R"-P-IR (2) or IR(1)-P-R'/R"-IR (2) (wherein R'/R" denotes the common recombination sequence), and optionally d) repeating steps a–c one or more times to produce bacterial cells comprising one or more additional copies of the DNA structure IR(1)-R'/R"-P-IR(2) or IR(1)-P-R'/R"-IR(2).

In a still further aspect the invention relates to a method for constructing a bacterial cell, which in its genomic DNA has integrated more than one copy of a DNA sequence of interest, and which is free from a DNA sequence encoding an undesired selectable marker, which method comprises a) introducing a first vector comprising a DNA construct according to the fourth aspect of the invention comprising the structure IR(1)-R'-M2-T-R"-P-IR(2), IR(1)-P-R'-M2-T-R"-IR(2), IR(1)-R'-T-M2-R"-P-IR(2) or IR(1)-P-R'-T-M2-R"-IR(2) optionally in association with a selectable marker gene M1 into the host cell, in which R' and R" denote parallel repeat sequences, b) selecting for cells being M1$^-$ (if M1 was pre sent on the vector) and M2$^+$, which in their genome comprises the relevant structure identified in a), c) selecting for cells having an increased number of copies of the selectable marker gene M2, d) allowing homologous recombination between the DNA sequences R' and R" to take place so as to excise the selectable marker gene M2 and the transposase gene T, whereby cells are obtained having integrated the structure IR(1)-R'/R"-P-IR(2) or IR(1)-P-R'/R"-IR(2) (wherein R'/R" denotes the common recombination sequence), and optionally e) repeating steps a-d one or more times to produce bacterial cells comprising one or more additional copies of the DNA structure IR(1)-R'/R"-P-IR(2) or IR(1)-P-R'/R"-IR(2).

It will be noted that integration of the DNA construct according to the first and third aspect, respectively, results in the same host cell harbouring the structure IR(1)-R-P-IR(2) or IR(1)-P-R-IR(2) and that integration of the DNA construct according to the second and fourth aspect, respectively, results in the same host cell harbouring the structure IR(1)-R'/R"-P-IR(2) or IR(1)-P-R'/R"-IR(2).

In step a) of any of the above methods, the vector may be introduced into the bacterial cell by any method suitable for the bacterial cell in question. A variety of methods for introduction of DNA into bacterial cells are well known in the art. These include the use of competent cells (by chemical treatment, or "natural" competence), protoplast transformation, conjugation, electroporation, transduction, or ballistic transformation. While conjugation may be accomplished by use of well-known self-transmissible plasmids as cloning vectors (e.g. the plasmid pLS20), the following specific conjugation method has been found to be generally applicable for introduction of DNA into cells, e.g. of Bacillus sp., which cannot or only with difficulty receive DNA by conventional methods such as protoplast fusion and the like.

More specifically, conjugation is conveniently achieved by a method, in which a population of bacterial donor cells harbouring i) a plasmid comprising a DNA construct of the invention and at least one cis-acting DNA sequence required for the transfer of said plasmid by conjugation in the presence of a trans-acting mobilizing element, and ii) at least one DNA sequence encoding said trans-acting mobilizing element, and a population of recipient cells are mixed under conditions allowing the plasmid to be transferred from the population of the donor cells to the population of recipient cells by conjugation. The population of donor cells may, e.g., be a population of cells of E. coli or a Bacillus sp., examples of which are mentioned further below. The recipient cells are preferably cells of a Bacillus sp. such as the ones mentioned further below. Of particular interest is recipient cells of B. licheniformis, B. amyloliquefaciens and B. lentus and non-competent cells of B. subtilis. The cis-acting DNA sequence and preferred locations thereof in the DNA construct or vector of the invention are described in the section above entitled "Cis-acting conjugational elements".

The term "trans-acting mobilizing element" in intended to indicate a protein mediating conjugative transfer of DNA sequences containing the cis-acting DNA sequence defined above. The trans-acting mobilizing element may be a protein encoded by a conjugational plasmid, such as the Bacillus sp. plasmid pLS20 (Koehler and Thorne, Journal of Bacteriology, Nov. 1987, pp. 5771–5278), or a part or derivative thereof, or may be a protein encoded by a DNA sequence such as orf-β of the plasmids pBC16 or pUB110 (Sellinger et al., Journal of Bacteriology, June 1990, pp. 3290–3297) or a functional analogue or part thereof. It will be understood that since the mobilizing element is acting in trans it may be encoded by DNA present in the genome of the donor cell or on a second plasmid present in said donor cell.

The mixing of the cells is conveniently performed by mixing the donor and recipient cells and allow them to stand for at least 4 hours at 30°–37° C. and selecting for recipient cells having received the DNA construct. See Selinger et al., 1990, for further reference.

The cultivation conditions to be used in step b) depend, inter alia, on the kind of selectable marker. For instance, when the selectable marker encoded by M2 is an antibiotic resistance the cultivation of b) is performed in the presence of a suitable dosage of the antibiotic in question so as to select cells having received and expressing M2.

Selection and screening are considerably facilitated by the presence of the antibiotic resistance markers M1 and M2 on the DNA construct which is introduced into the recepient host cell. The marker M1 being present on the "vector part" of the DNA construct, i.e. the part of the construct outside the structure defined by IR(1) and IR(2), whereas the marker gene M2 is present within said structure. However, it may be noted that succesfull transposition can be obtained also when the DNA construct comprises only one selectable marker, i.e. either M1 or M2.

Following a suitable growth regime, e.g. as given in the literature for pHV1248 (Petit, M.-A., Bruand, C., Janniere, L., Ehrlich, S. D. (1990), Tn10-derived transposons active in Bacillus subtilis, J. Bacteriol., 172, 6736–6740), strains containing M2 are selected on plates containing the proper antibitic, and screened by replica plating for the absence of M1. Such strains no longer harbour the transposon delivery vector, and has the transposable structure integrated into their genome. Integration of the DNA construct by transposition may occur a t random positions throughout the genome of the host cell. Thus, when multicopy cells are produced the integrated copies will be located at random, separate positions of the cell which contributes to increasing the genetic stability of the cell.

The presence of P may be evaluated by methods known in the art, e.g., as appropriate, by southern analysis, PCR amplification, or phenotypic expression of P. When the DNA construct to be introduced into the cell harbours a selectable marker gene M1 the loss of the M1 phenotype is used to indicate loss of the vector part of the introduced DNA once transposition has taken place.

When the DNA construct according to the first or third aspect of the invention is used (i.e. a DNA construction comprising target sequences for a site-specific recombinase enzyme) a subsequent step is to introduce a second vector expressing the site-specific recombination enzyme cognate to the target sequences flanking M2 into the strain having recieved the first vector. The activity of the recombination enzyme recombines the two target sequences, which in the genome flanks M2 and optionally T, thus deleting this marker gene and optionally T, an event which is easily detected by screening, e.g. by replica plating.

Once M2-free strains are obtained, these are cured for the plasmid expressing the recombination enzyme, e.g. by propagation at non-permissive temperature if the vector is a temperature-sensitive replicon. Alternatively, the vector is allowed a certain time of residence in the host, which is then cured for the vector, and the plasmid free cells screened for loss of M2.

The result of this process is a strain that contains one transposed copy of the gene of interest, but no marker gene. This strain is now used as a host strain in a new round of transposition and marker deletion, in which it is possible to employ exactly the same modified transposon delivery vector and recombination enzyme encoding vector as in the first round, i.e.

i) the modified transposon delivery vector is introduced into the host strain, ii) strains containing a transposed copy of the DNA sequence of interest plus the marker gene M2, and free of transposon delivery vector, are obtained as described above, iii) the vector expressing the cognate site specific recombination enzyme is introduced into these strains (in case of the DNA construct according to the third aspect), and iv) strains from which the marker gene M2 and optionally T is deleted due to the activity of the recombination enzyme (when constructed from a DNA construct according to the first or third aspect) or homologous recombination (when constructed from a DNA construct according to the second or fourth aspect) are isolated as above, and plasmid free versions of such strains obtained.

The result of this is now a strain containing two transposed copies of the gene of interest, but no marker gene.

This can again serve as host strain in a new round of transposition and marker deletion, and the process can be repeated essentially an infinite number of times.

If the DNA sequence encoding the recombinase enzyme is provided in cis under a regulatable promoter (as discussed above), only one transformation step need to be done in each round. In practice when transposition has been accomplished the regulatable promoter is switched on and the recombinase enzyme expressed.

Marker deletion by the site-specific recombination enzyme leaves one copy of the cognate target sequence in the chromosome. Subsequent transposition events brings in new copies of this target sequence. As transposition can occur to a substantial number of sites within the genome, approaching random integration, the new target sequences will with high probability be situated at a considerable distance from the first one. It is likely that the site-specific recombination enzyme may function less efficiently on very separated sequences. It is furthermore likely that the deletion of a substantial amount of genomic DNA, which would result from such a recombination event, would be lethal, so strains where this has taken place would not be isolated by the described procedure.

An analogous process is carried out in connection with strains produced by use of a DNA construct according to the second or fourth aspect of the invention. In this case the excision of the marker gene M2 and, when relevant T, is obtained by homologous recombination between the sequences R' and R".

The Cell of the Invention

In a further aspect the invention relates to a bacterial cell, which in its genome has integrated more than one copy of a DNA construct comprising the following structure IR(1)-P-IR(2), in which IR(1) and IR(2) denote transposase target sequences, and P a DNA sequence of interest, wherein the structure IR(1)-P-IR(2) does not encode an undesired selectable marker. The structure further comprises a recombination target sequence R or the common homologous recombination sequence R'/R" in between IR(1) and IR(2).

In the present context the term "genome" is intended to indicate the constituent DNA of the cell comprising the chromosome and stably inherited extrachromosomal elements.

In the present context the cell into which the DNA construct is to be integrated is denoted host cell, host strain, recipient strain or cell, modified cell or the like. It will be understood that these terms are used interchangeably.

The presence of IR(1) and IR(2) in the genome of the cell is not essential for the function of the cell, but is evidence to the fact that the cell has been constructed by transposition, i.e. by use of transposons. Thus, only cells having been modified by transposition comprise the above structure. If necessary, the IR(1) and/or IR(2) may be deleted or inactivated from the cell by conventional means.

In a further aspect the invention relates to a bacterial cell, which in its genome has integrated at least two copies of a DNA construct comprising the following structure IR(1)-P-IR(2), in which IR(1) and IR(2) denote transposase target sequences, and P a DNA sequence of interest, the structure further comprising a recombination target sequence R or the common homologous recombination sequence R'/R" in between IR(1) and IR(2).

It is presently believed that the present disclosure is the first description of the use of transposition for construction of multicopy grampositive cells, in particular Bacillus cells. The presence of multiple, normally randomly located copies of the structure IR(1)-P-IR(2) further comprising R or R'/R" in the genome of a cell shows that the cell has been constructed by transposition.

From the above disclosure it will be apparent that the present invention is a very convenient and efficient method of constructing multicopy gram-positive bacterial strains, i.e. bacterial cells which integrated in their genome comprises multiple copies of a DNA sequence of interest. The cells produced according to the present invention are either a) cells which in their genome has integrated at least two copies of a DNA construct comprising the structure IR(1)-P-IR(2), the structure further comprising a recombination target sequence R or the common homologous recombination sequence R'/R" in between IR(1) and IR(2), which structure is free from any gene encoding an undesirable, e.g. antibiotic resistance marker.

Of particular interest is a cell which in its genome (also outside the structure IR(1)-P-IR(2) further comprising a DNA sequence R or R'/R") is free from a gene encoding an antibiotic resistance marker or another undesired marker type. The presence of such genes normally follows when multicopy strains are constructed by conventional methods, including transposition when based on transposition delivery vectors known in the art.

Although the cell of the invention is preferably free from any introduced selectable marker it may contain a gene encoding a harmless (i.e. not undesirable) selectable marker such as a a growth-inhibiting marker or an antibiotic-resistance marker. These types of markers are discussed in detail above in the section entitled "Selection marker".

The cell of the invention may be of any gram-positive bacterial species, in particular a cell of a *Bacillus sp.* or a *Lac-tobacillus sp.* Examples of suitable cells of Bacillus may be selected from the group consisting of *Bacillus subtilis, Bacillus licheniformis, Bacillus lentus, Bacillus brevis, Bacillus stearothermophilus, Bacillus alkalophilus, Bacillus amyloliquefaciens, Bacillus coaculans, Bacillus circulans, Bacillus lautus, Bacillus megaterium, Bacillus thuringiensis.* In connection with the use of *B. lentus* it may be noted that there has been no prior disclosure or indication to the fact that transposition can work in cells of of said species.

As to the DNA sequence of interest present in the cell of the invention reference is made to the section "DNA sequence of interest" discussed above.

Finally, it will be understood that under circumstances where there is no desire of constructing a marker-free, single or multicopy strain M2 need not be eliminated after having served the purpose of identifying cells which in their genome comprise one or more copies of the DNA sequence of interest. In such cases transposition serves as a convenient method of introducing at least one and preferably multiple copies of a DNA sequence of interest into the genome of a cell.

Production of a Polypeptide of Interest

The cell of the invention comprising more than one copy of the structure IR(1)-P-IR(2) further comprising a DNA sequence R or R'/R" in between IR(1) and IR(2) integrated into its genome or a cell prepared by a method of the invention as described above may suitably be used in a method for producing a polypeptide of interest which is encoded by a DNA sequence P of interest.

The method comprises cultivating the cells in question in a suitable nutrient medium under conditions permitting the expression of the polypeptide, after which the resulting polypeptide is recovered from the culture.

The medium used to culture the cells may be any conventional medium suitable for growing the cells, such as minimal or complex media containing appropriate supplements. Suitable media are available from commercial suppliers or may be prepared according to published recipes (e.g. in catalogues of the American Type Culture Collection). The polypeptide produced by the cells may then be recovered from the culture medium by conventional procedures including separating the cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

The polypeptide is preferably a translocated polypeptide, in particular a secreted polypeptide such as a secreted enzyme. Alternatively, the translocated polypeptide is PrsA. Specific examples of polypeptides which may be produced in accordance with this aspect of the invention are given above in the section entitled "The DNA sequence of interest".

Conclusion

From the above description of the invention it will be apparent that the present invention is novel and inventive over the prior art for one or more of the following reasons:

1) transposons are used for insertion of more than one copy and a fixed, predetermined number of copies of a gene encoding a product of interest,
2) the transposed DNA contains elements that allow site-specific deletion of parts of the transposed DNA,
3) the resulting strains contain transposed DNA, but have no selection marker genes within the transposed DNA, and/or
4) transposons are used in an iterative process, made possible by the combination with a method to specifically delete marker genes.

From an industrial point of view, bacterial strains constructed in accordance with the invention may have the triple advantage of being i) high-yielding due to the presence of multiple gene copies,
ii) Genetically extremely stable, as the multiple copies are not tandem repeats but can be scattered over the chromosome, and
iii) Marker free, making them more "environmentally friendly" than traditional recombinant production strains containing antibiotic resistance genes.

BRIEF DESCRIPTION OF THE DRAWINGS

The invention is further described in the following examples with reference to the appended drawings, in which the following abbreviations are used:

"bla" indicates the beta-lactamase gene, encoding ampicillin resistance, from pUC19.

"erm" indicates the erythromycin resistance gene of pE194.

"cat" indicates the chloramphenicol resistance gene derived from pC194.

"IR" indicates the transposon inverted repeat sequence derived from Tn10.

"Tn ase" indicates the transposase from Tn10, modified to be expressed in Bacillus.

"PamyQ-sav" indicates the Savinase gene, expressed from the promoter for the B. amyloliquefaciens alpha-amylase gene.

"oriT(pUB110)" indicates the cis-acting sequence of pUB110 necessary for mobilization.

"ermR" indicates the erythromycin resistance gene derived from pAMβ1.

"repE" indicates the replication protein gene of pAMβ1.

"resB" indicates the resolvase gene of pAMβ1.

"TopB" indicates the topoisomerase gene of pAMβ1.

"amy'" indicates the 5' end of the B. subtilis amylase gene.

"lacZ" indicates the beta-galactosidase gene from E. coli.

"res" indicates the target site for the resolvase from pAMβ1.

"spc" indicates the spectinomycin resistance gene from Tn554.

"'amy" indicates the 3' end of the B. subtilis amylase gene.

"+ori pUB110" indicates the replication origin of pUB110 (the nick site).

"rep" indicates the replication protein gene of pUB110.

"kan" indicates the kanamycin resistance gene of pUB110.

"PamyL" indicates the promoter of the B. licheniformis alpha-amylase gene.

"kan'" indicates the 5' end of the kanamycin resistance gene of pUB110.

"'amyL" indicates the 3' end of the B. licheniformis alpha-amylase gene.

"repF" indicates the replication protein gene of pE194.

"Plac" indicates the beta-galactosidase promoter on pUC19.

"amyL" indicates the alpha-amylase gene from B. licheniformis.

Figure 1:
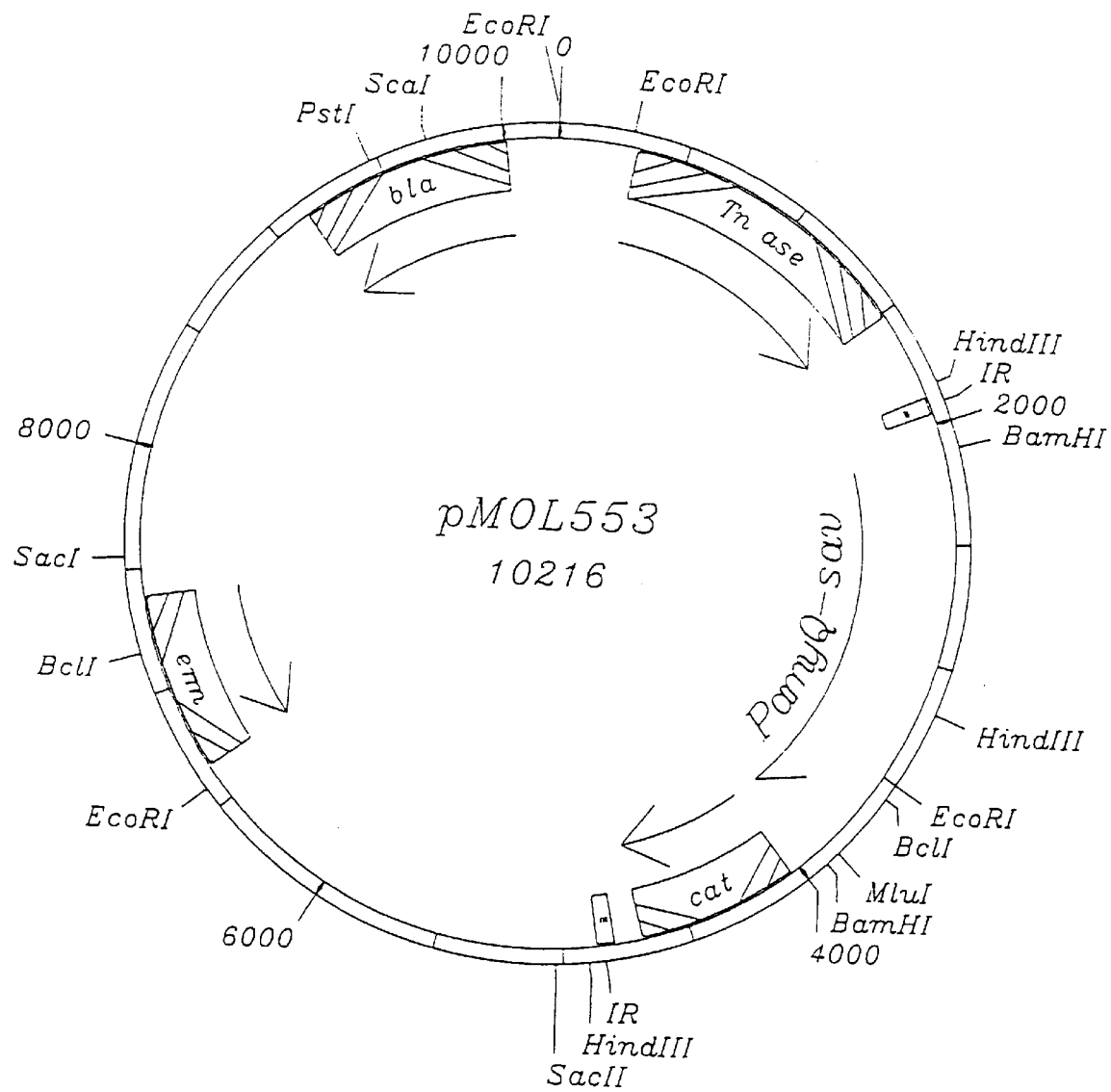
Figure 2:
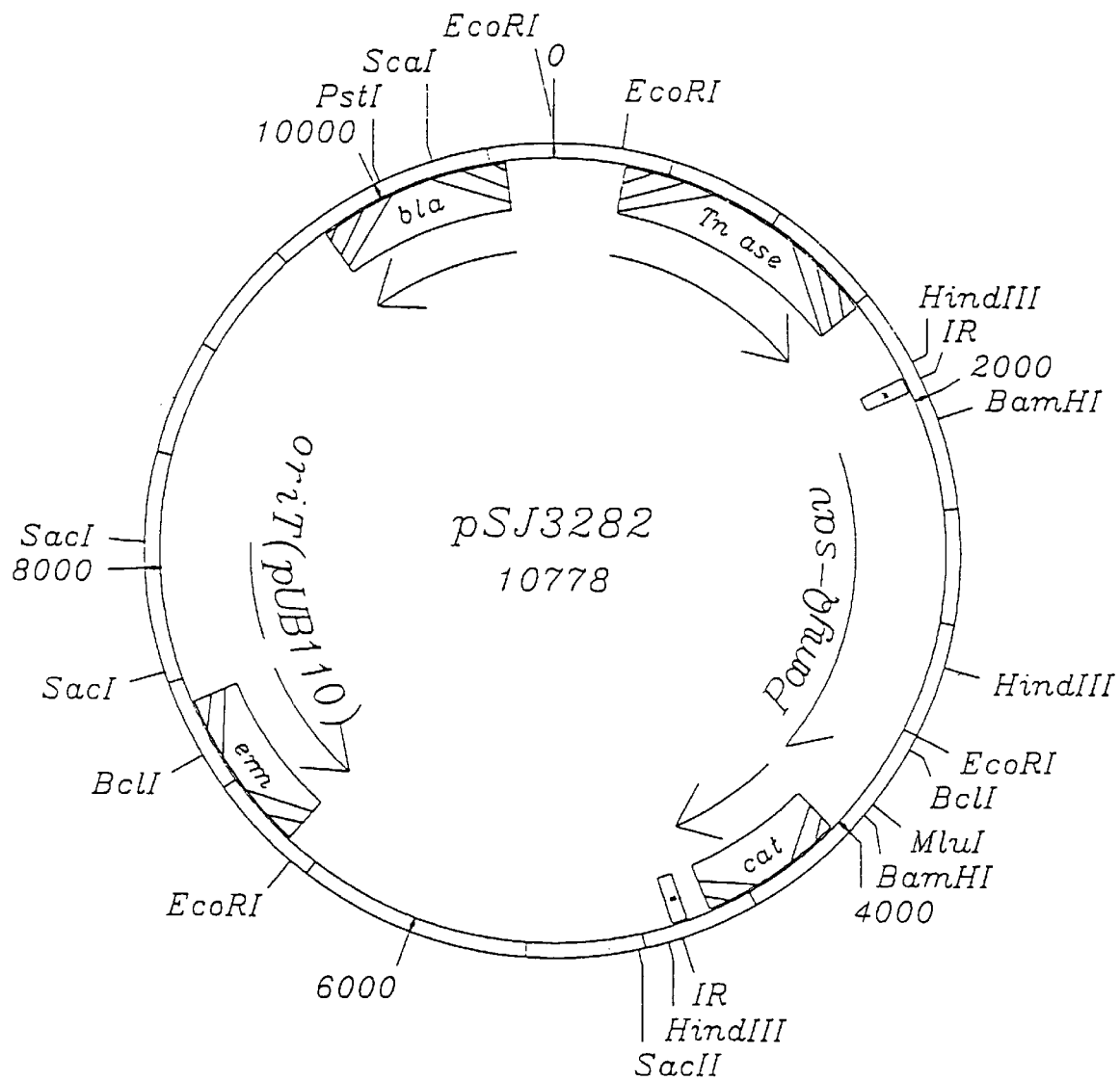
Figure 3:
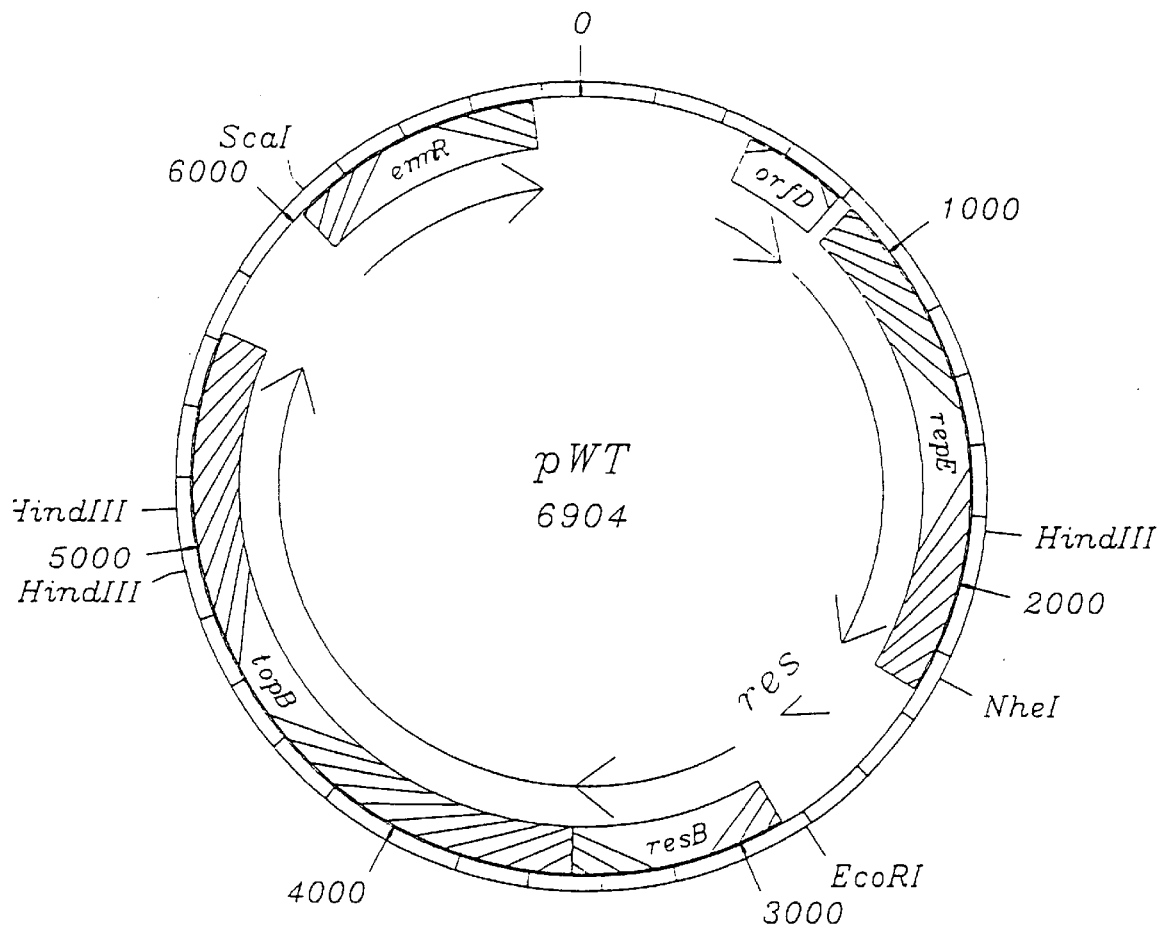
Figure 4:
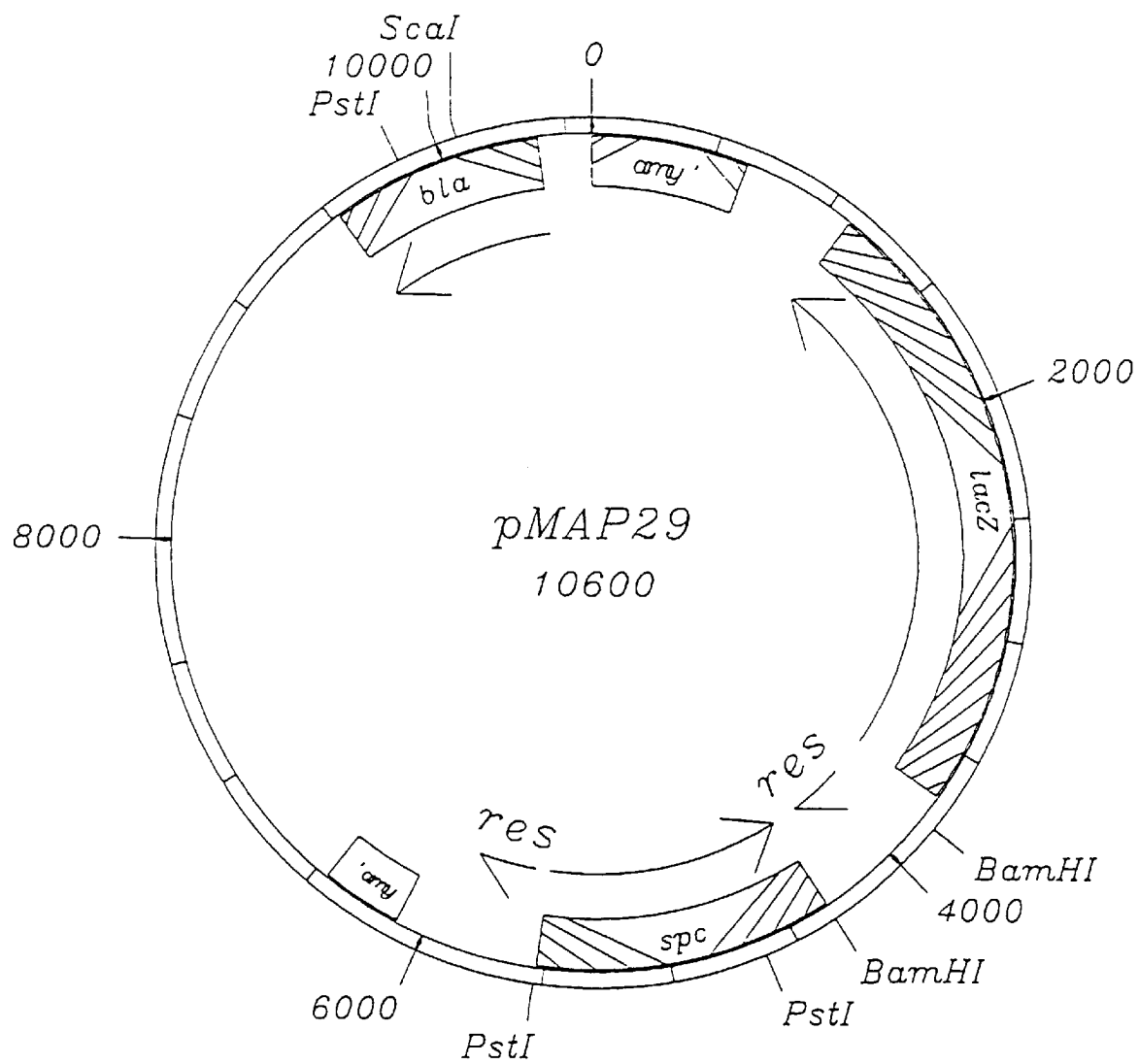
Figure 5:
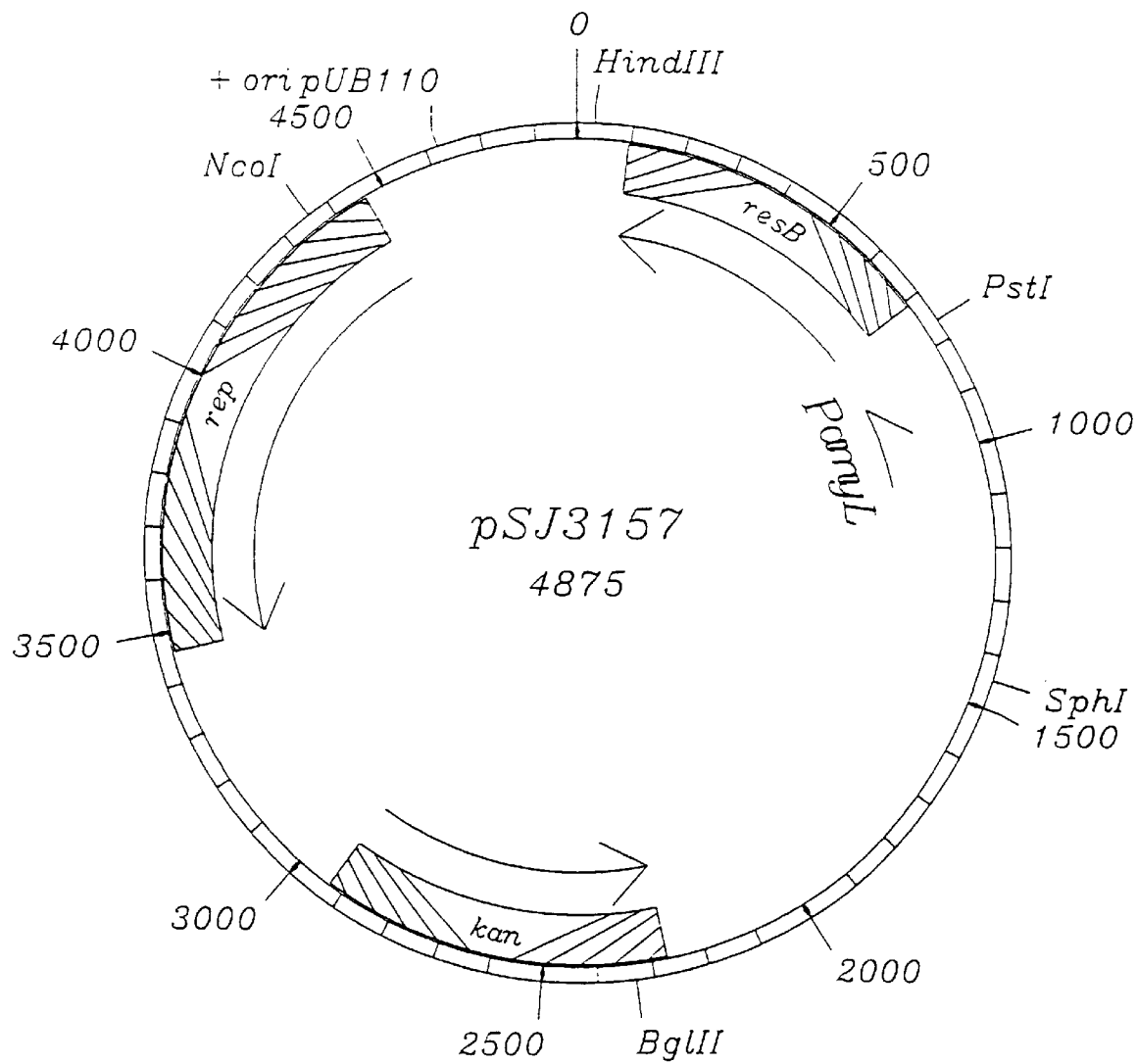
Figure 6:
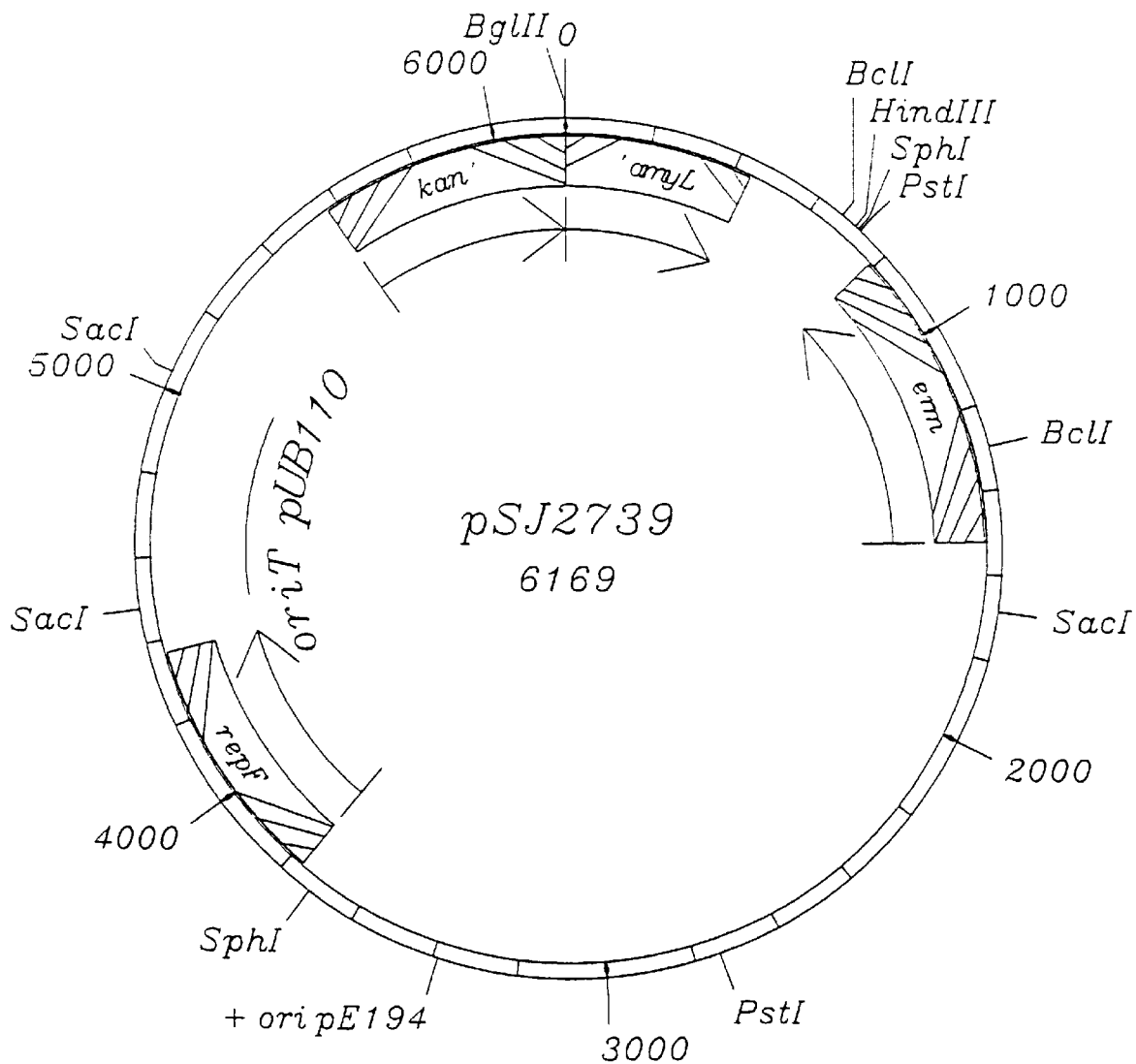
Figure 7:
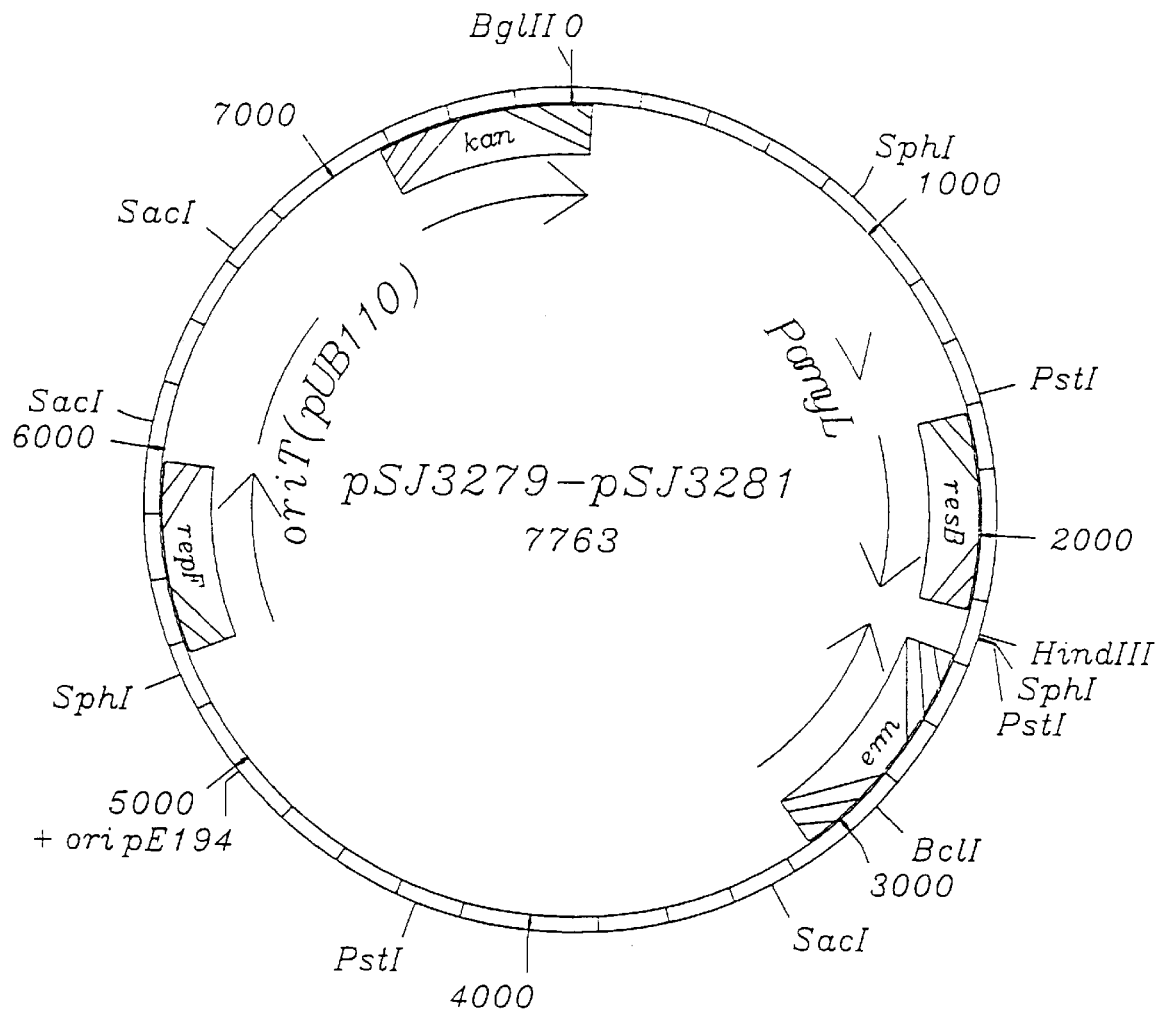
Figure 8:
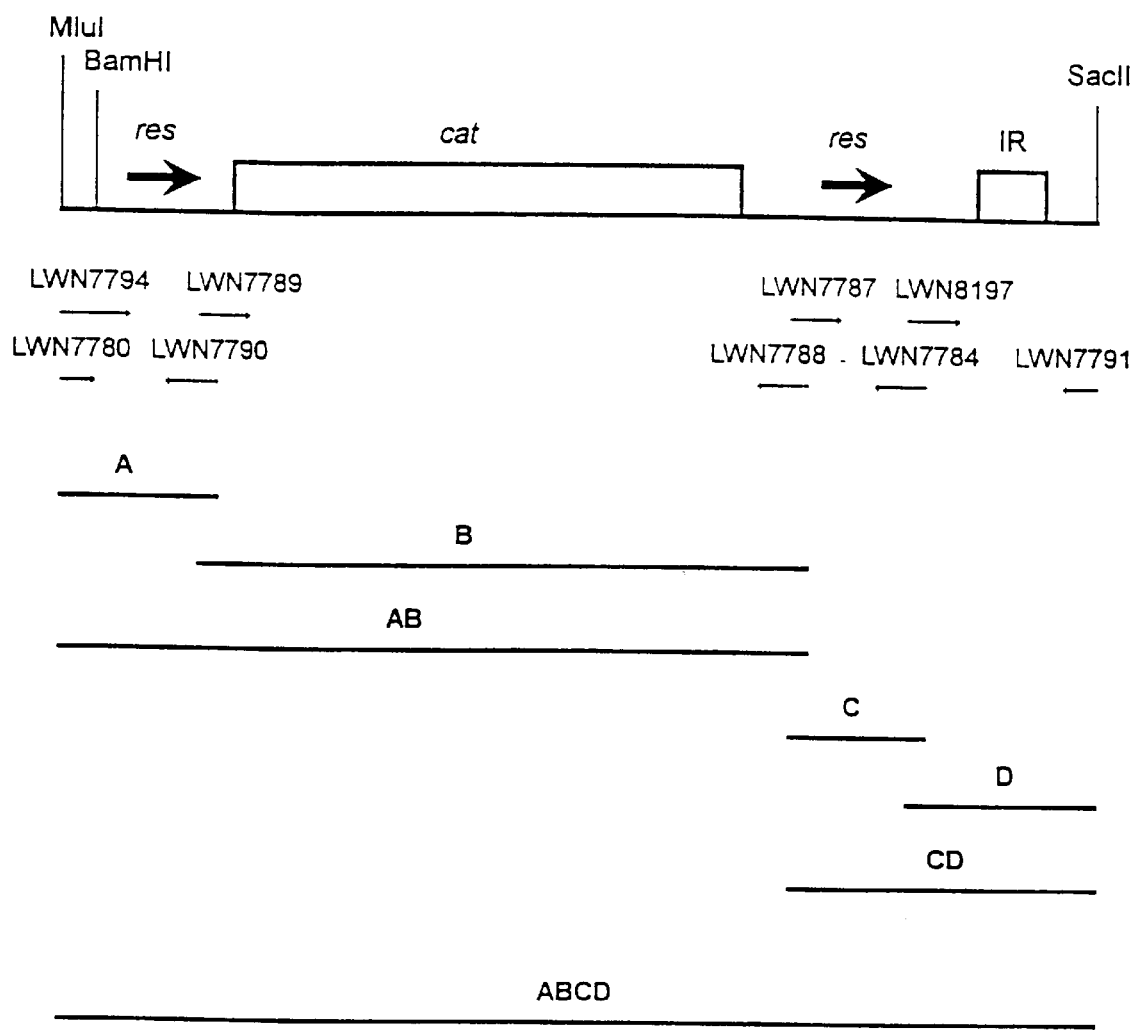
Figure 9:
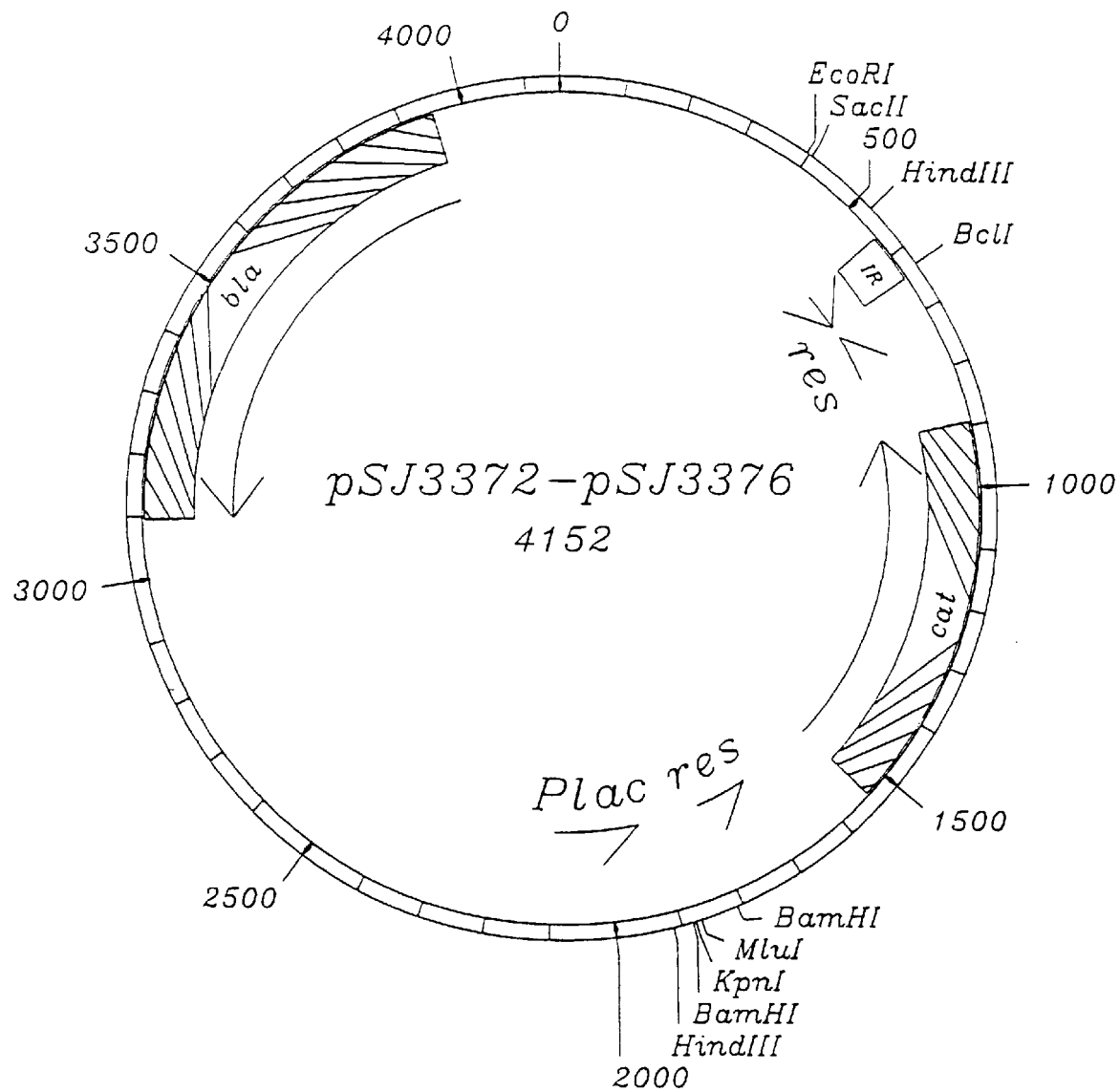
Figure 10:
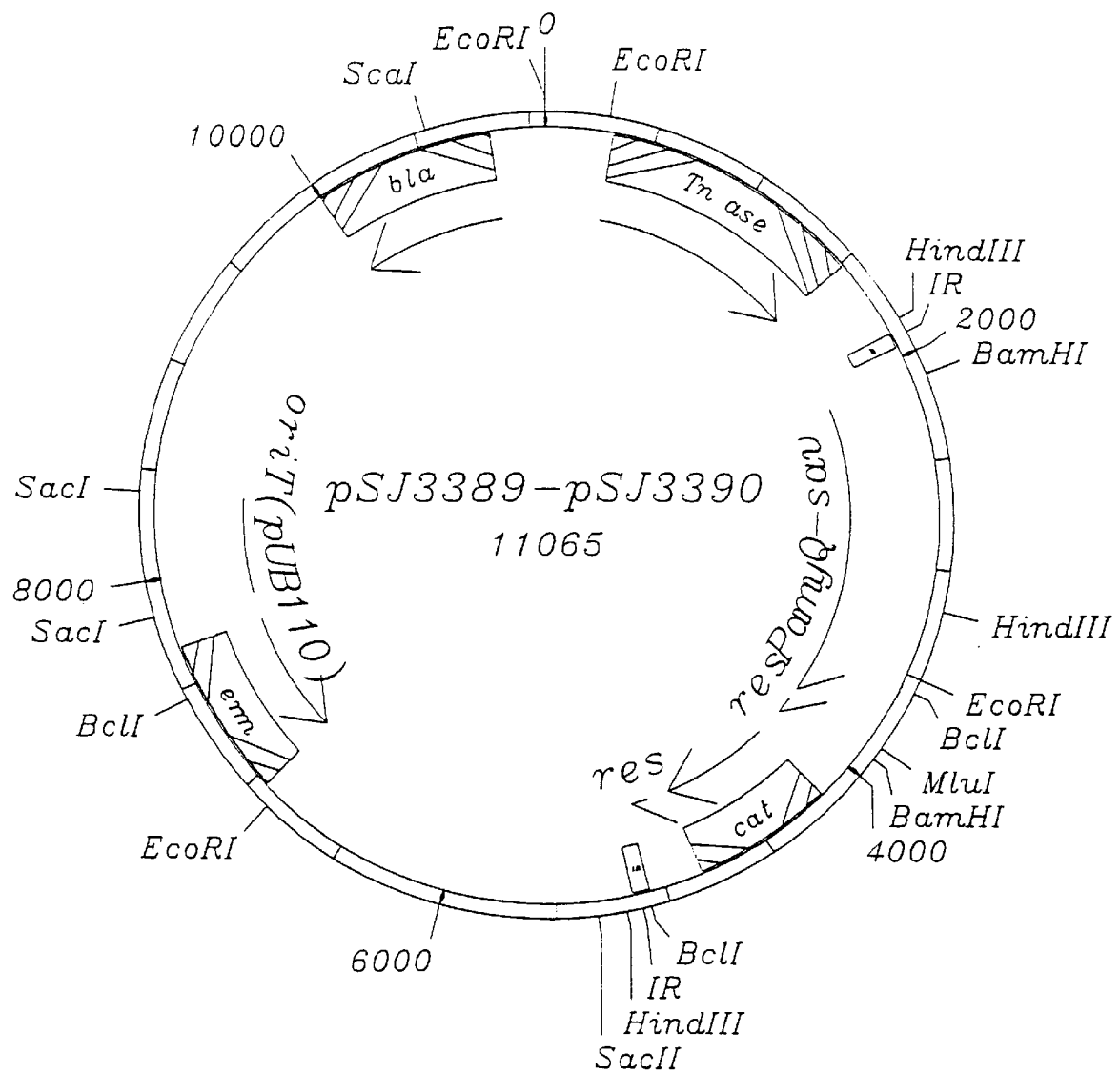
Figure 11A:
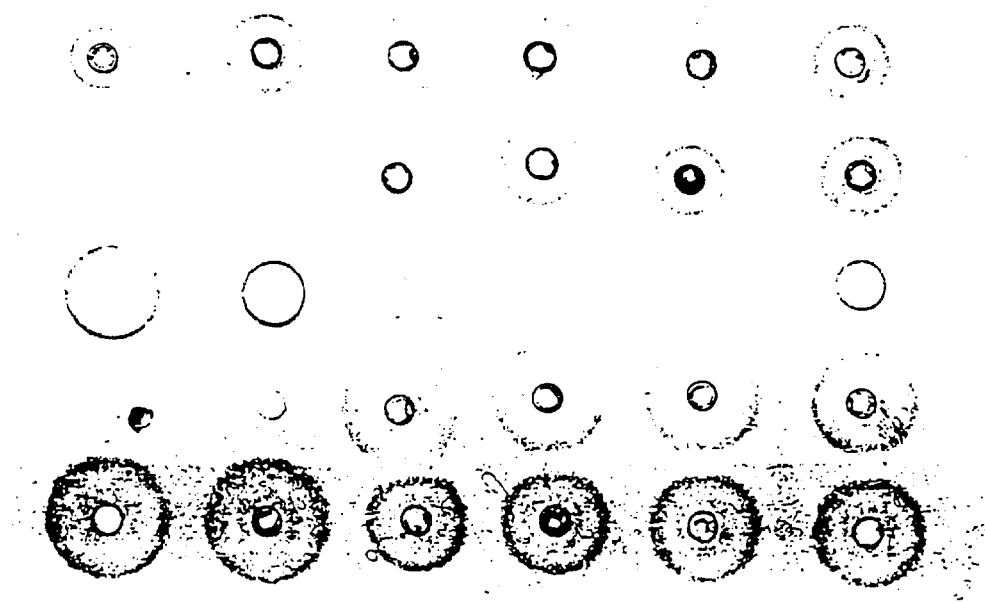
Figure 11B:
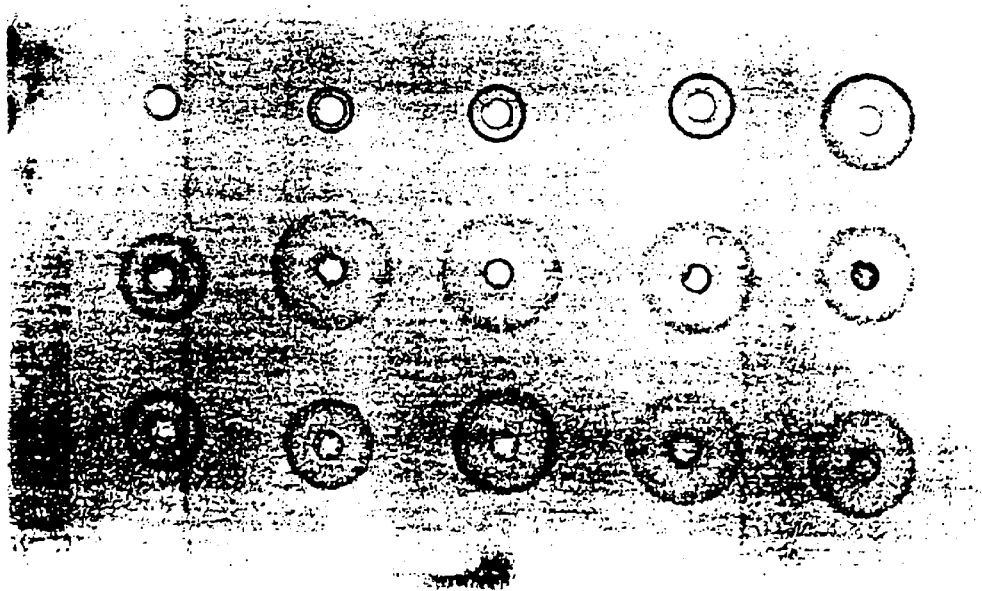
Figure 12A:
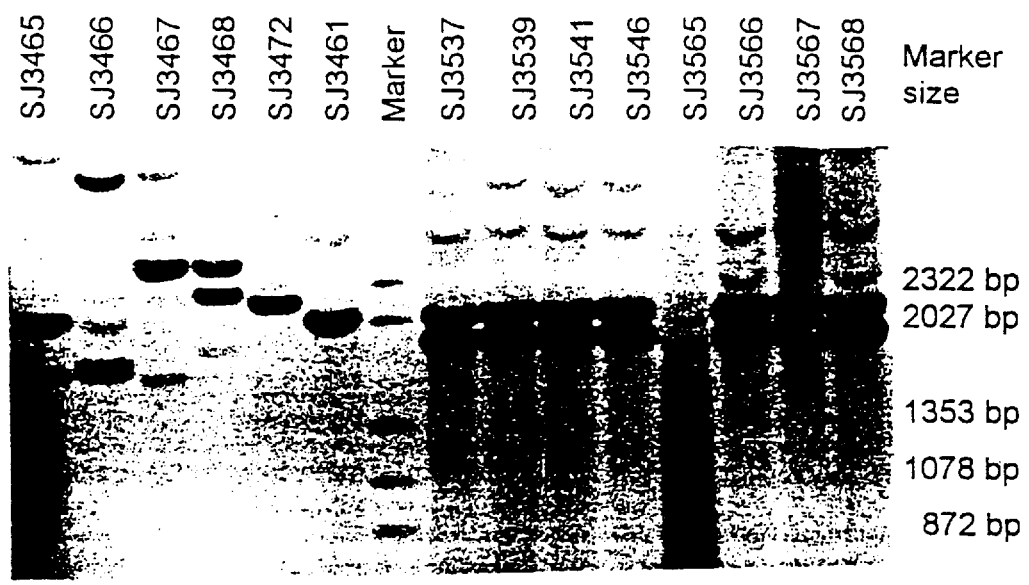
Figure 12B:
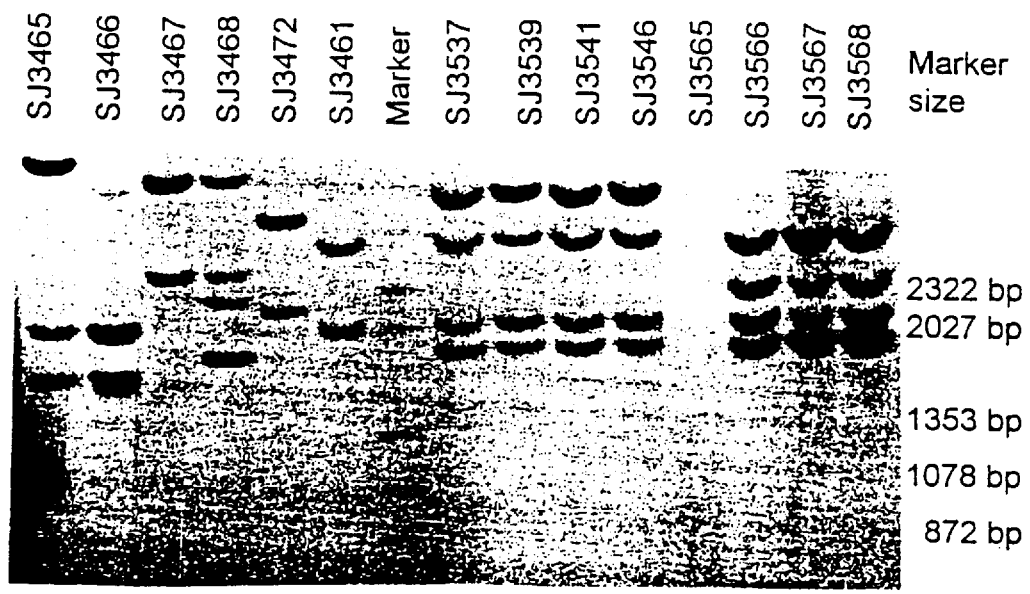
Figure 13:
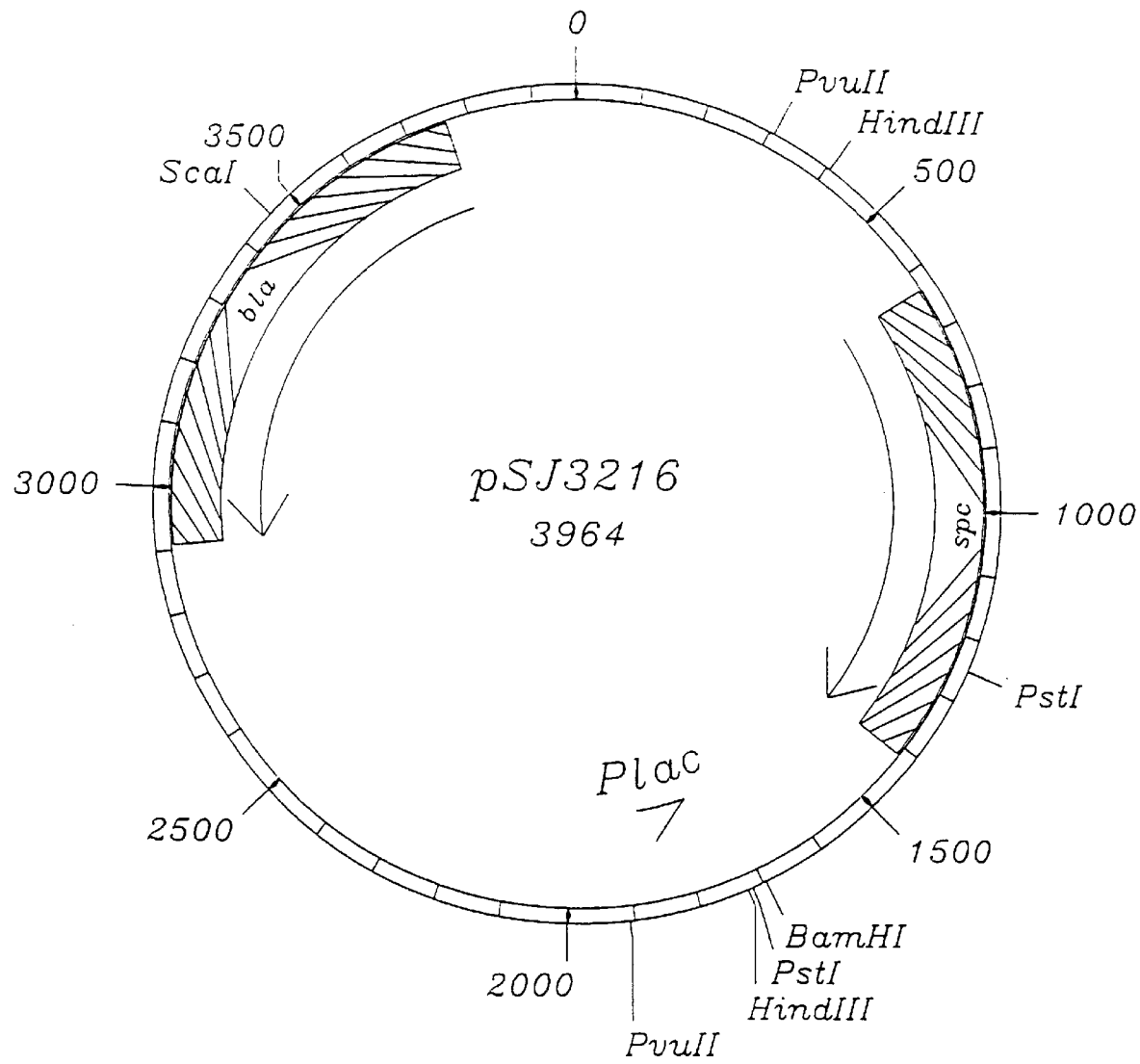
Figure 14:
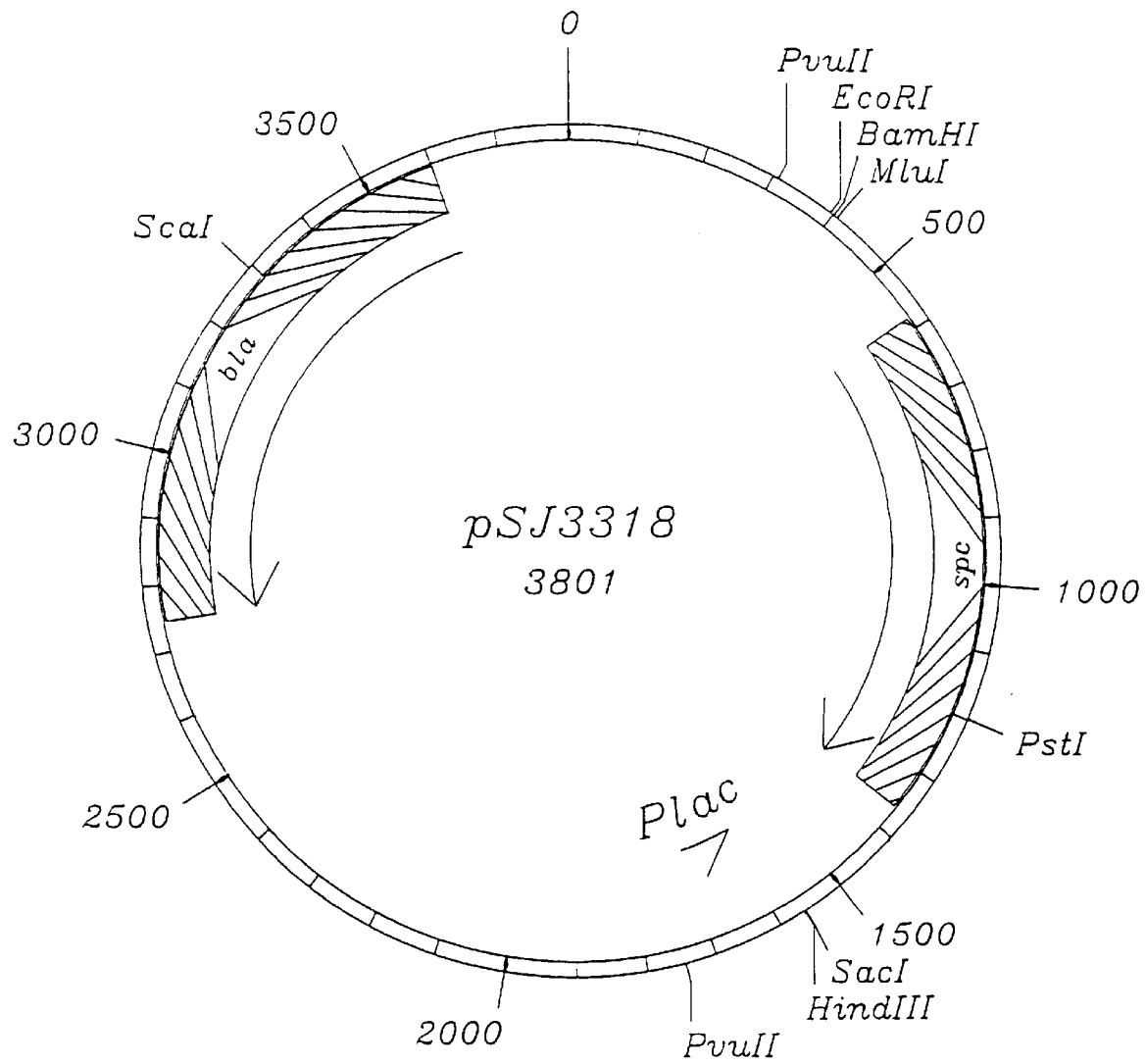
Figure 15:
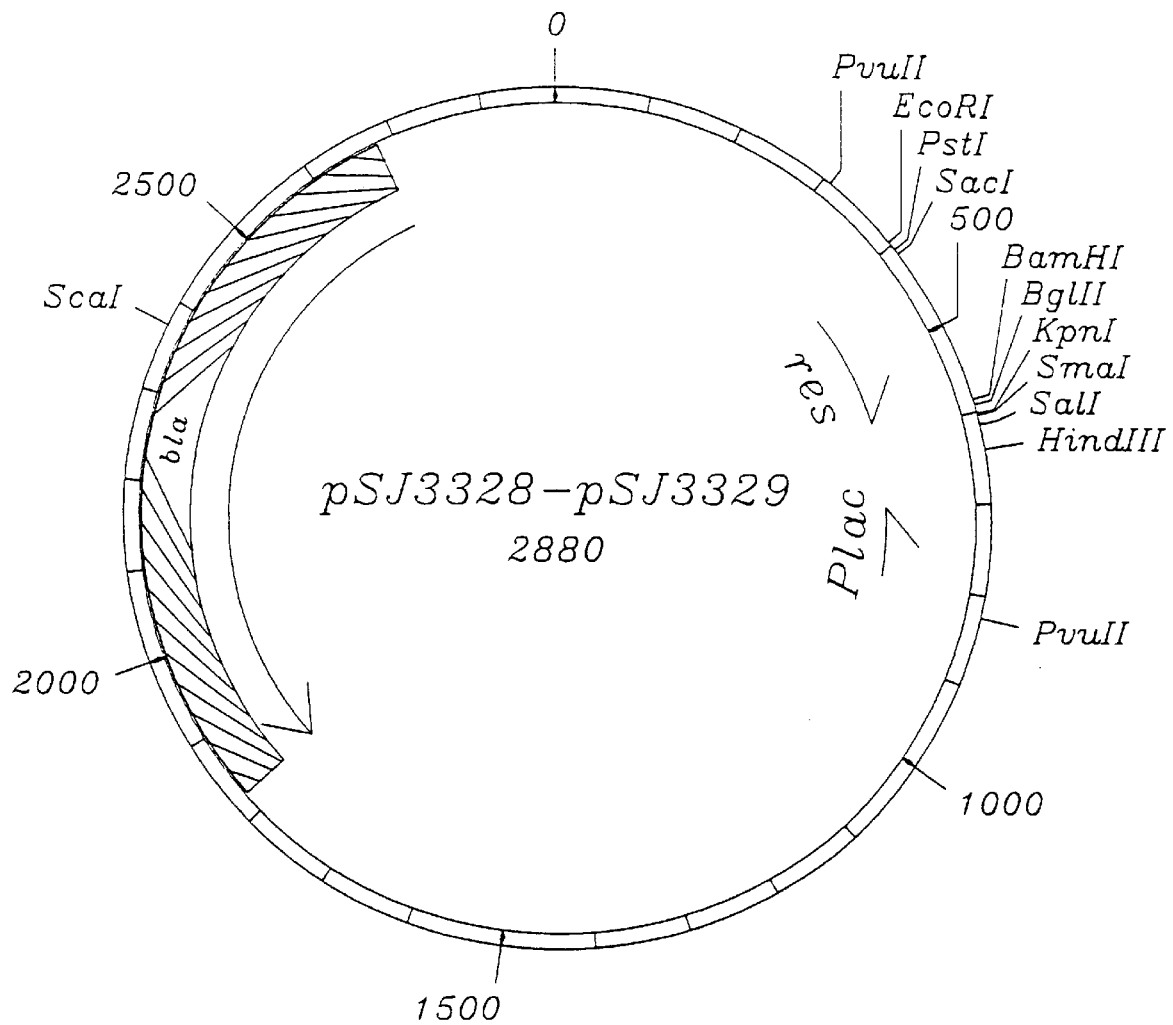
Figure 16:
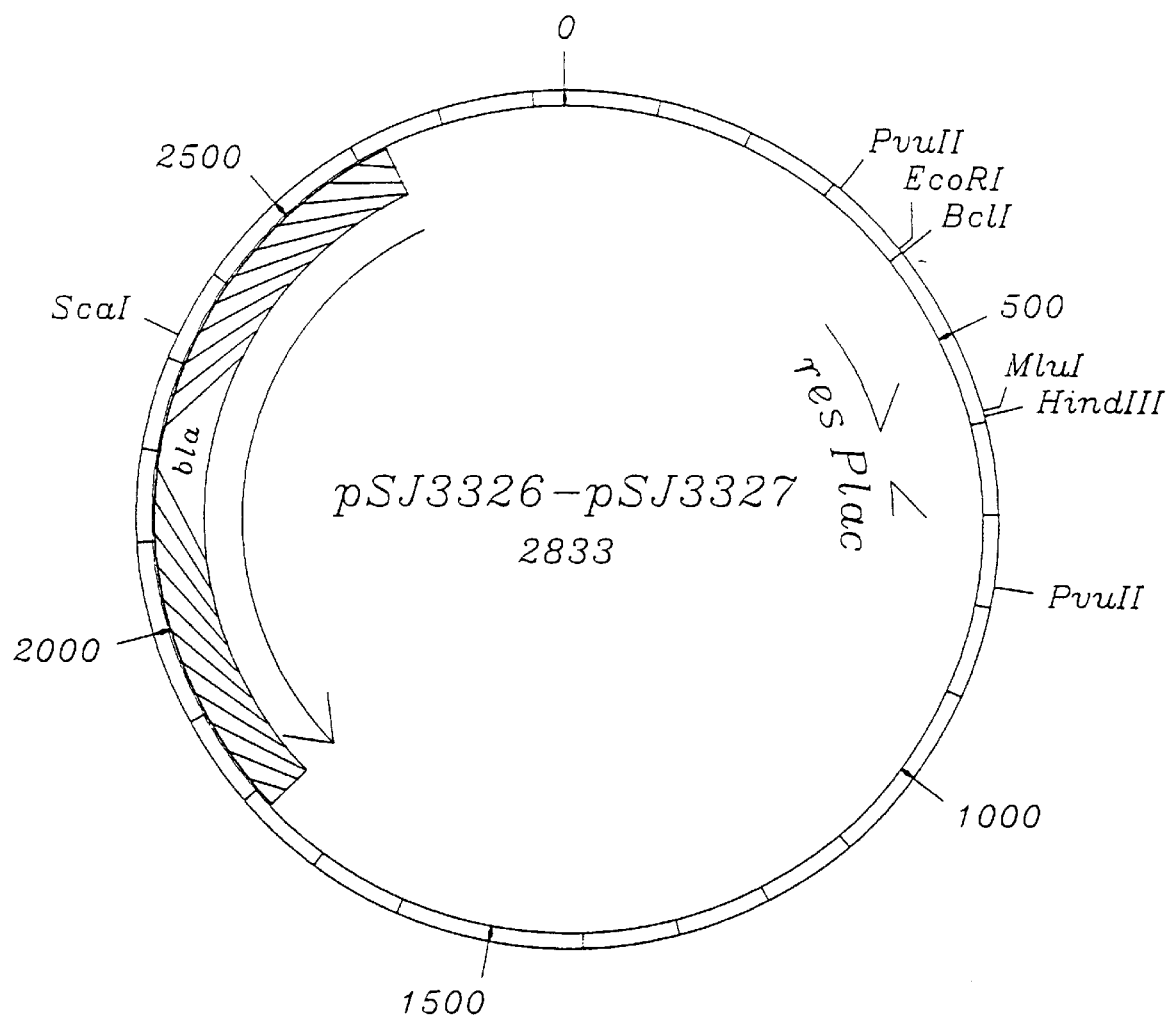
Figure 17:
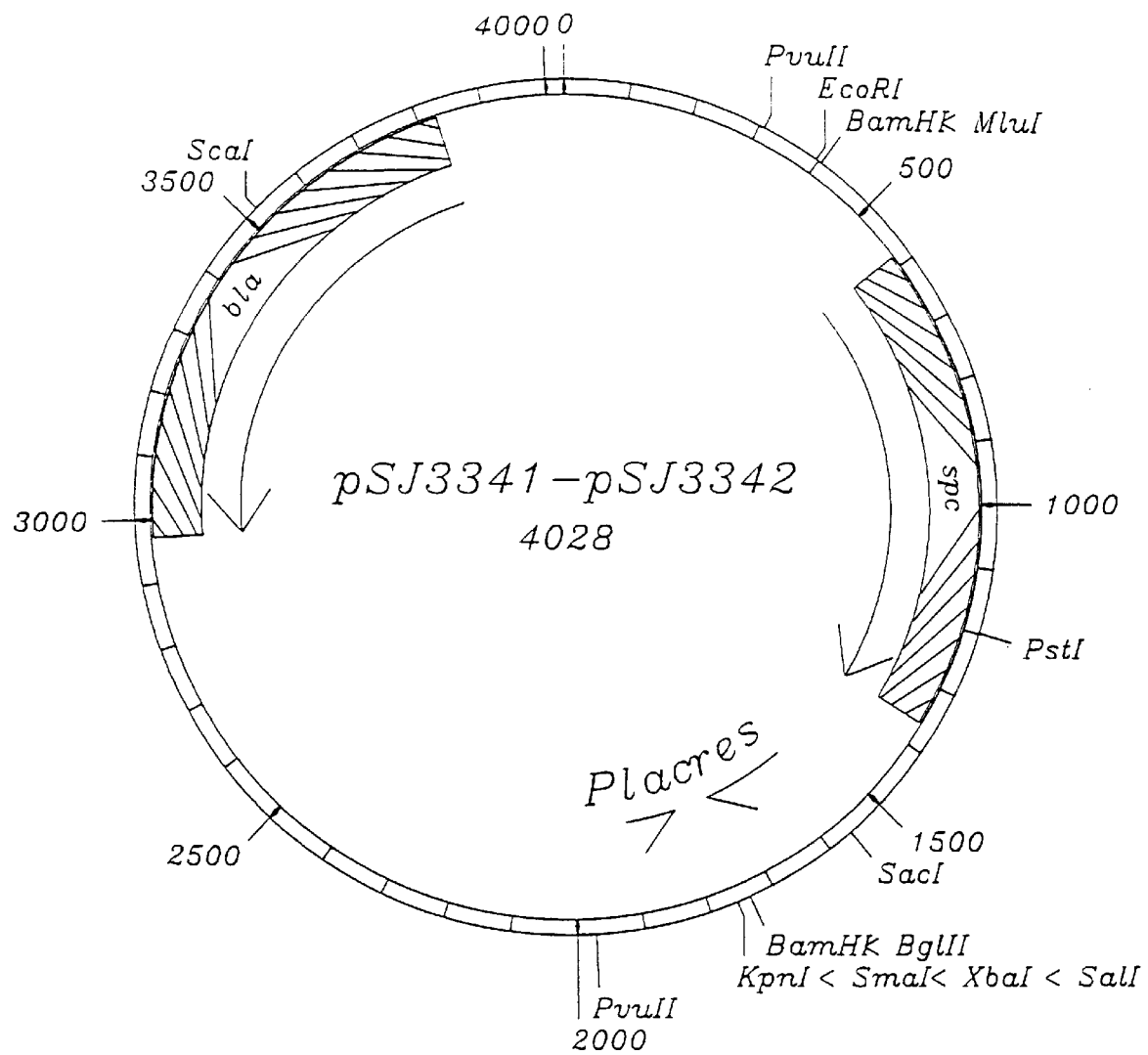
Figure 18:
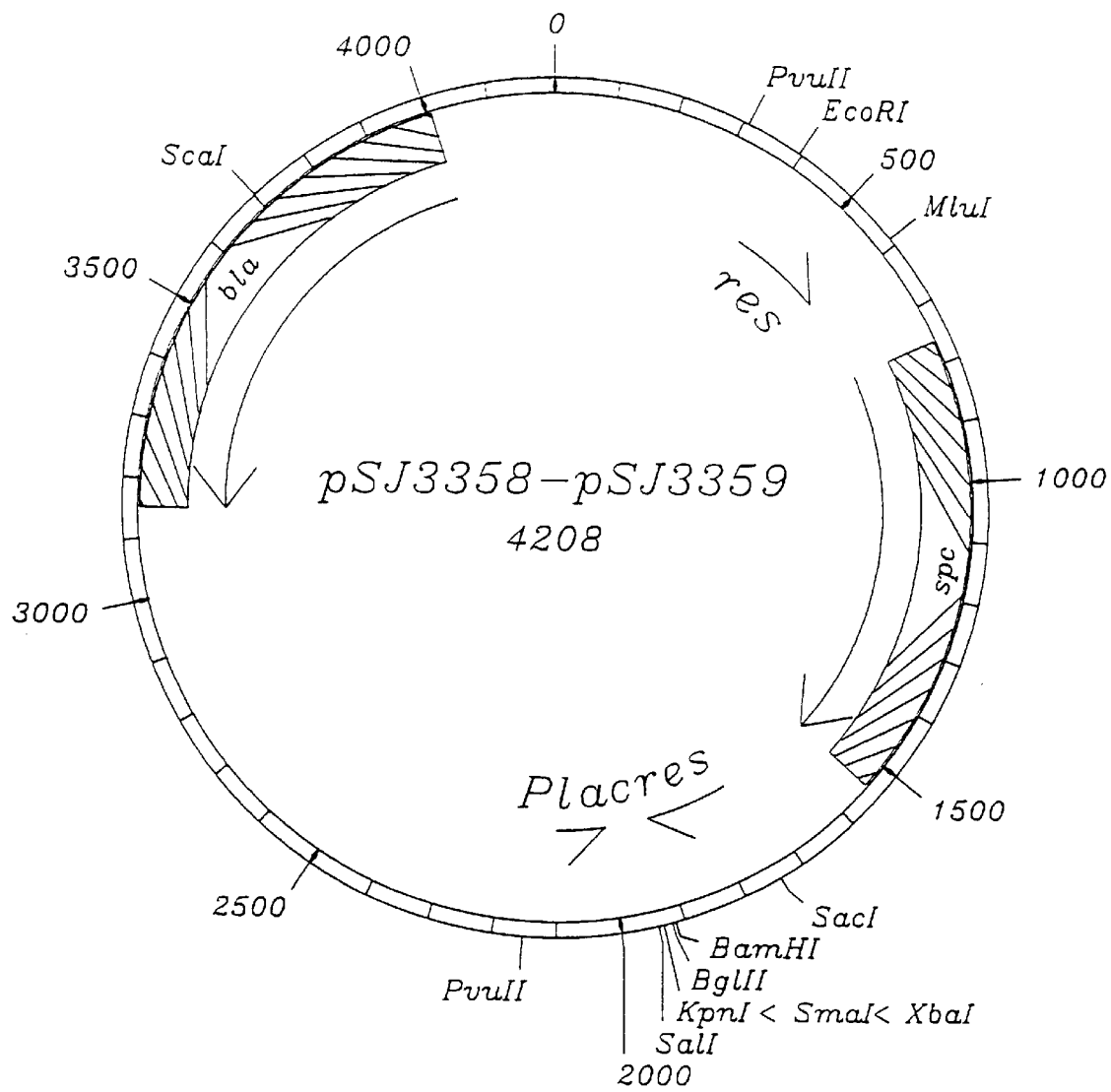
Figure 19:
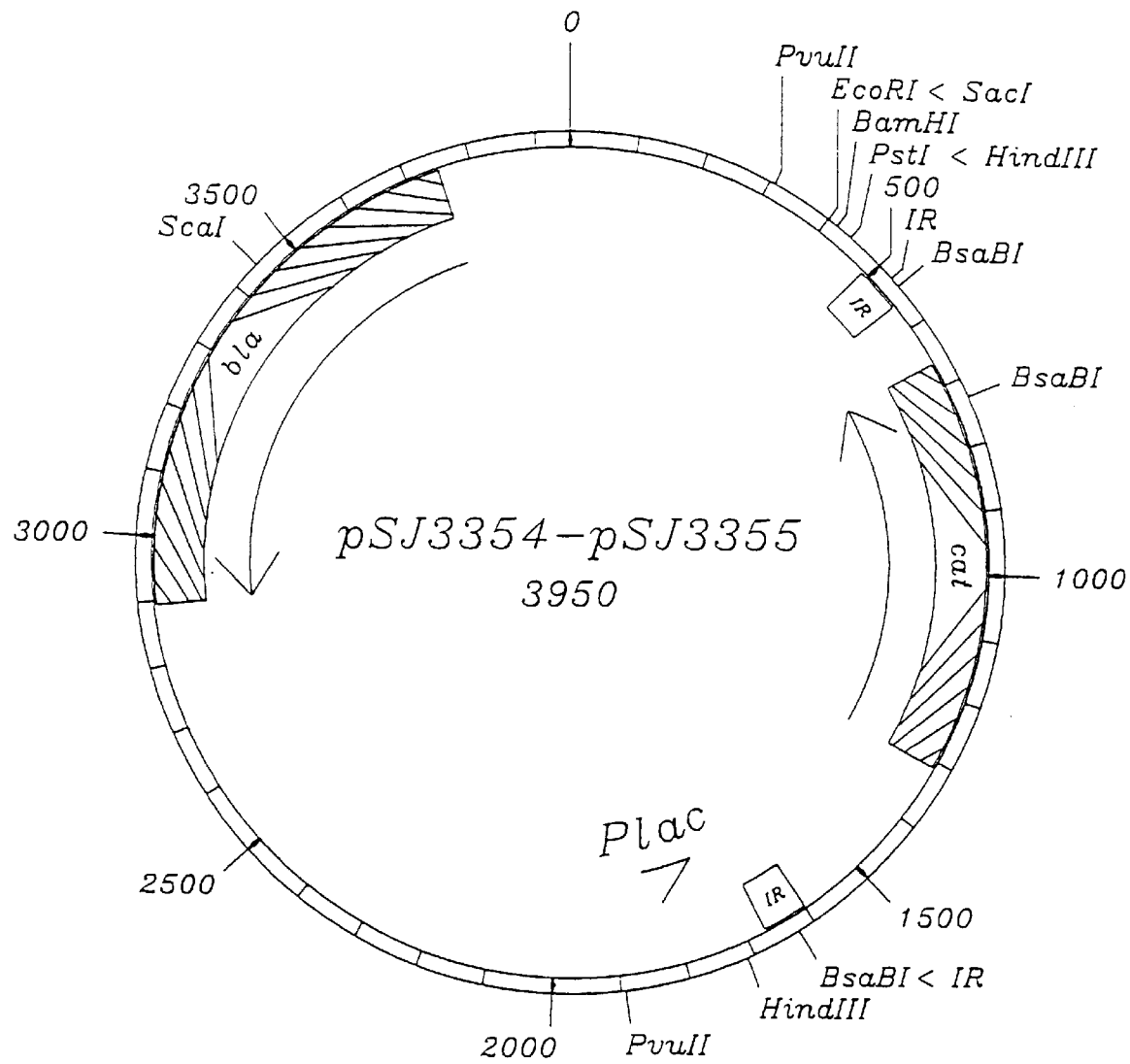
Figure 20:
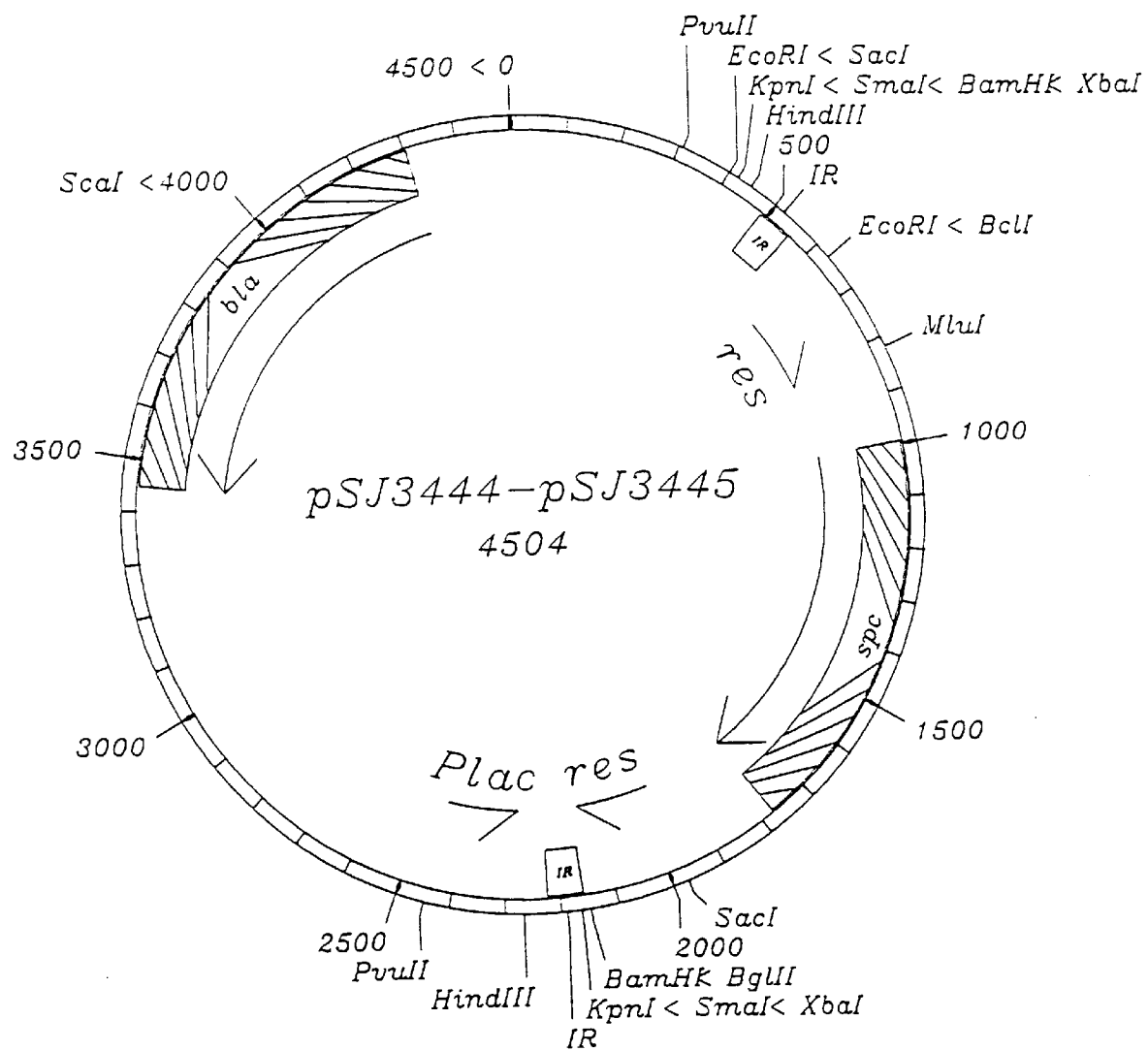
Figure 21:
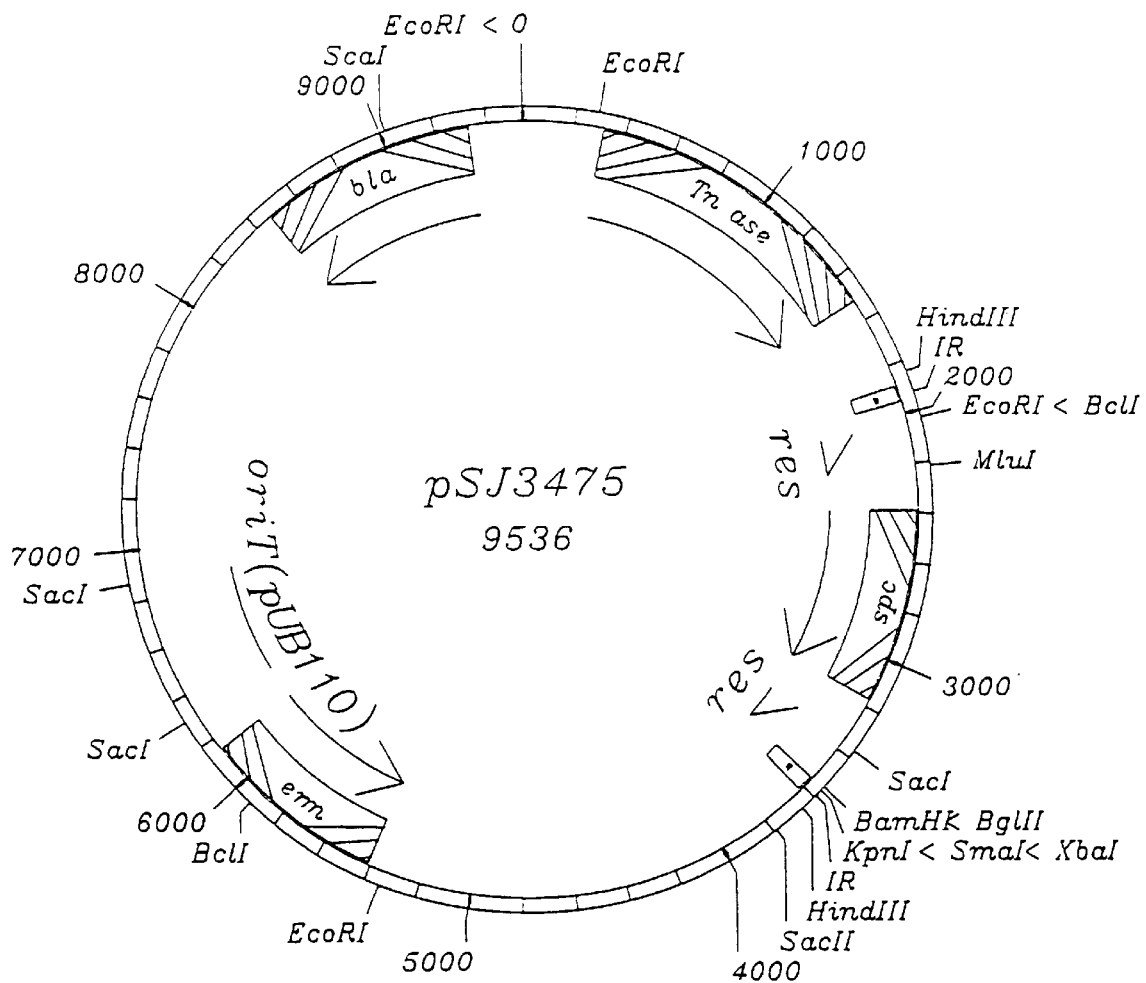
Figure 22:
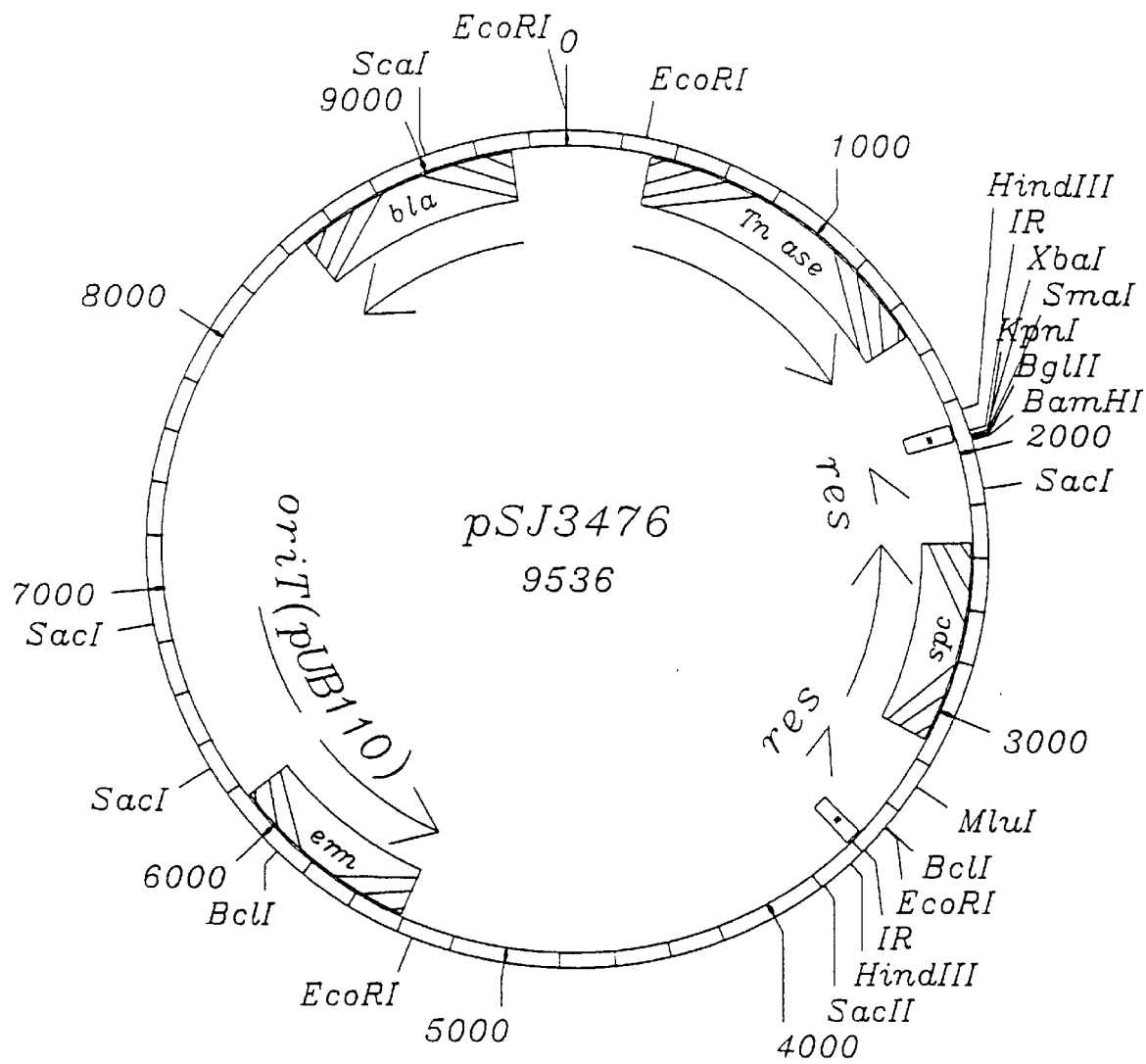
Figure 23:
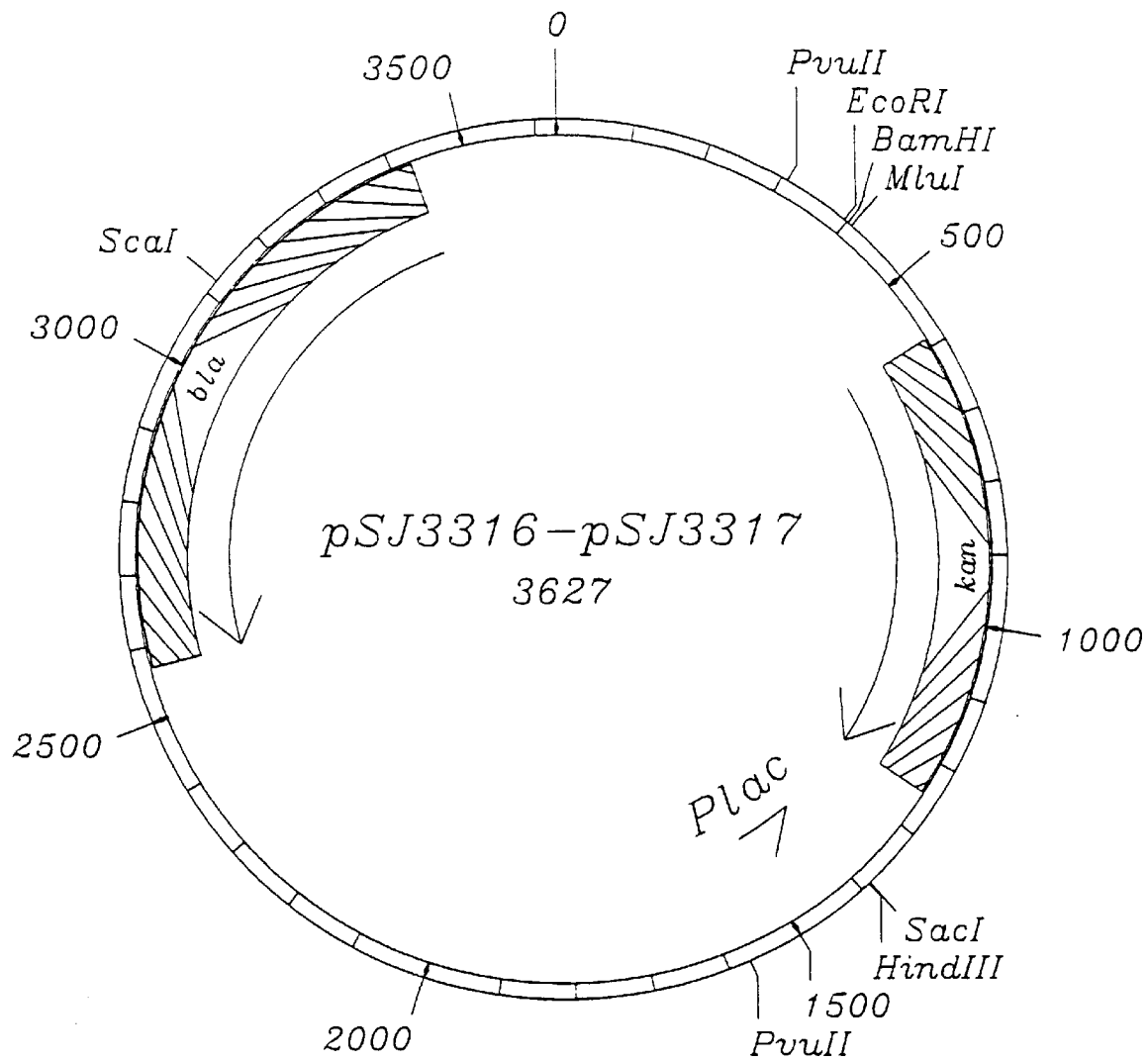
Figure 24:
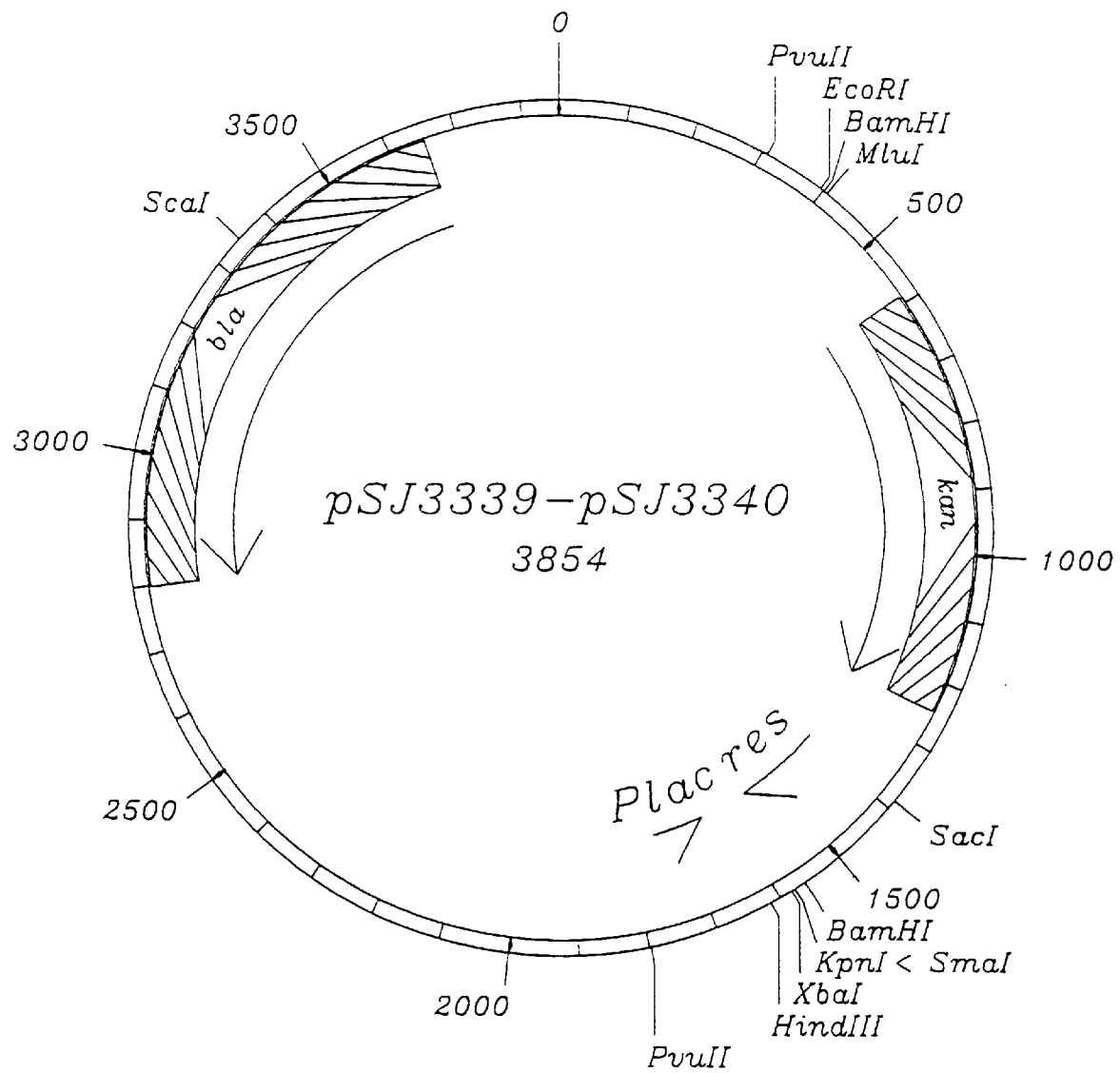
Figure 25:
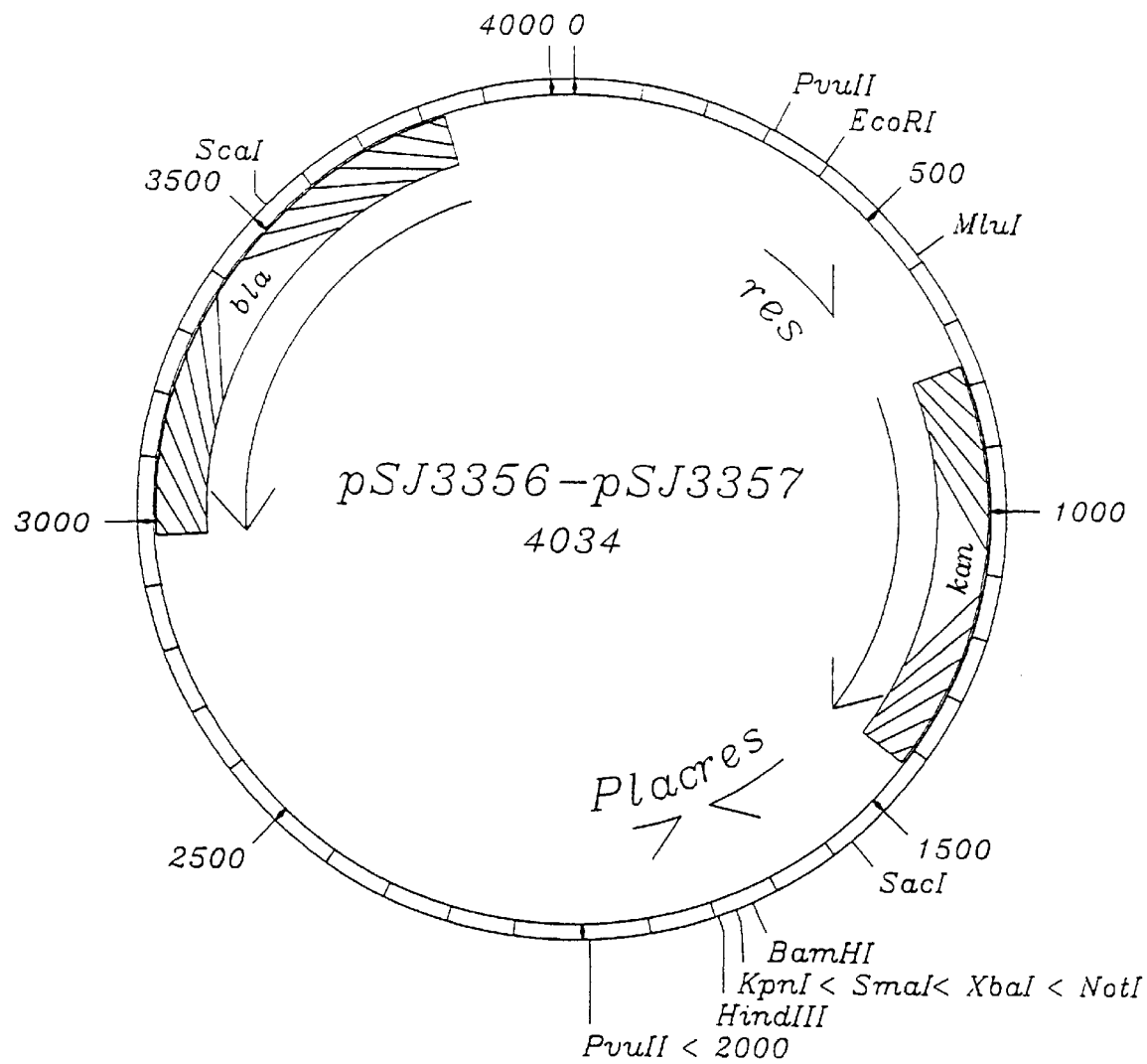
Figure 26:
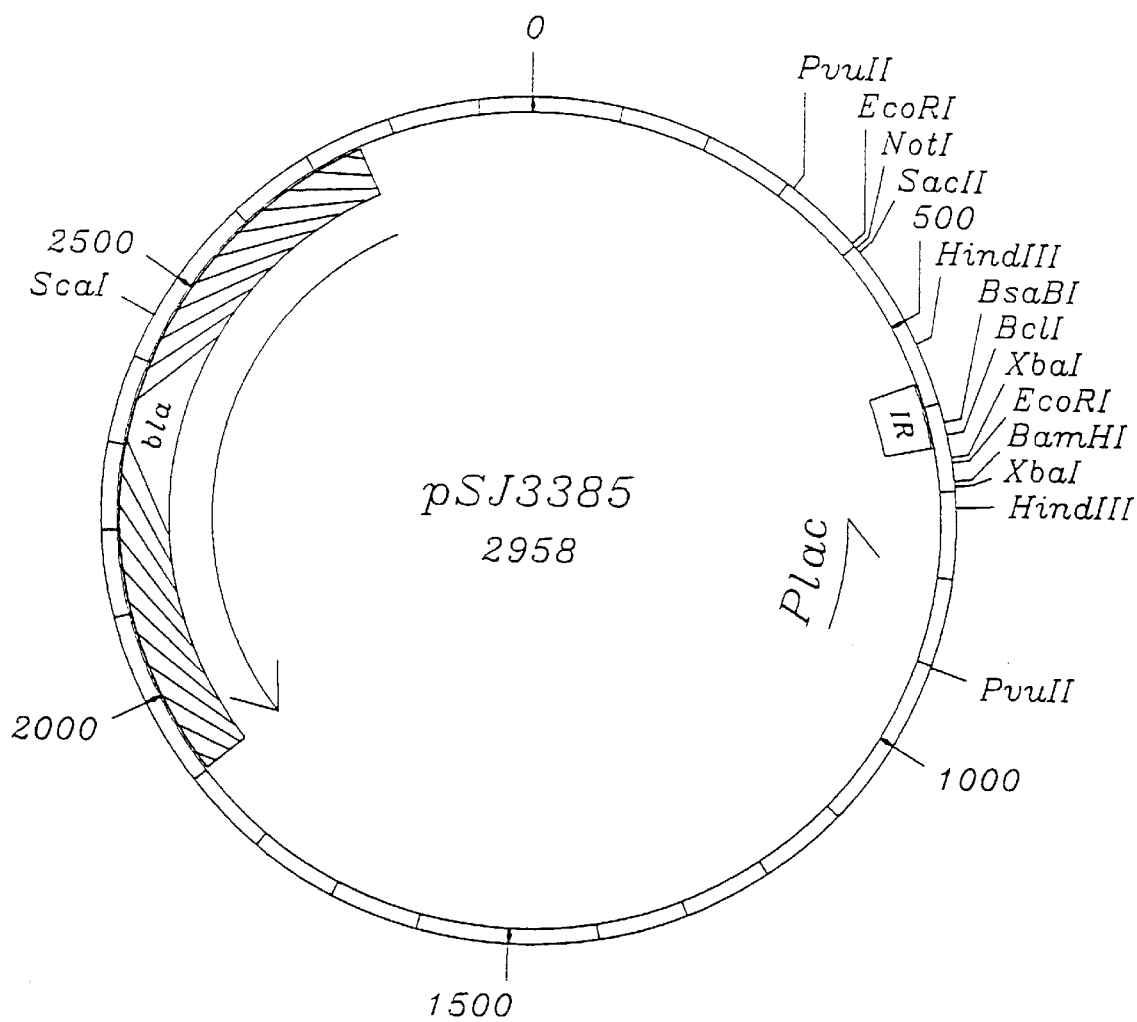
Figure 27:
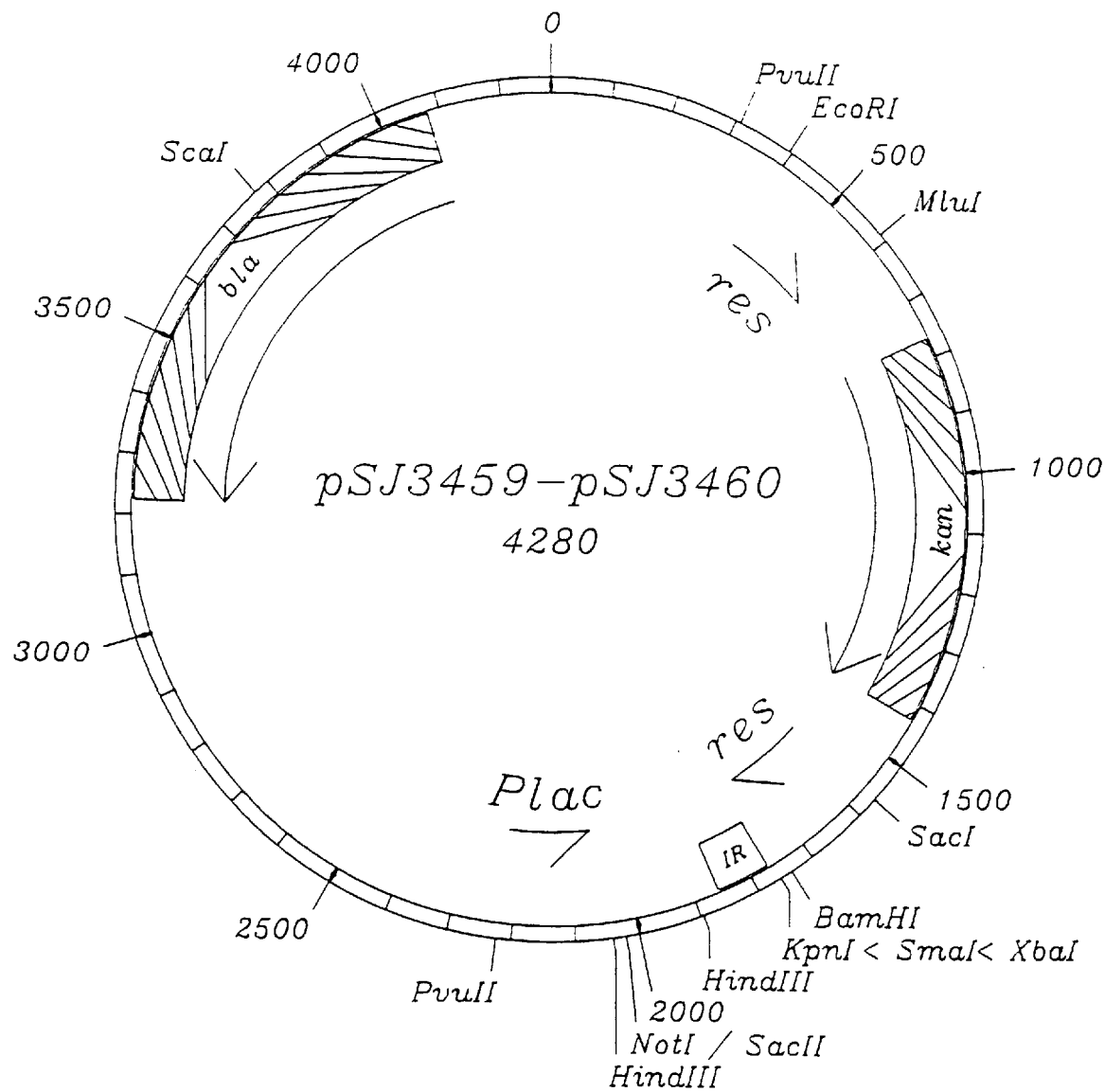
Figure 28:
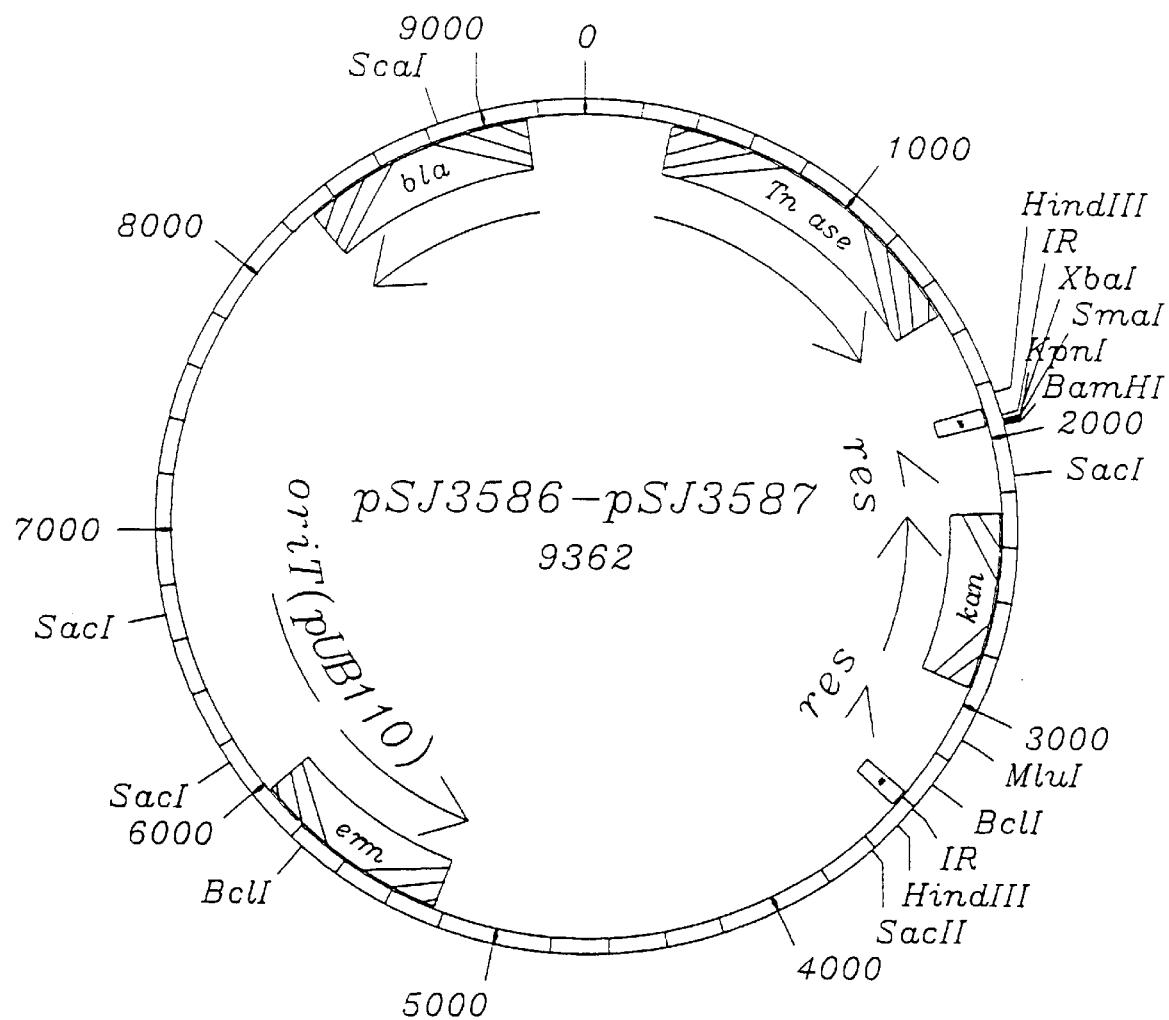
Figure 29:
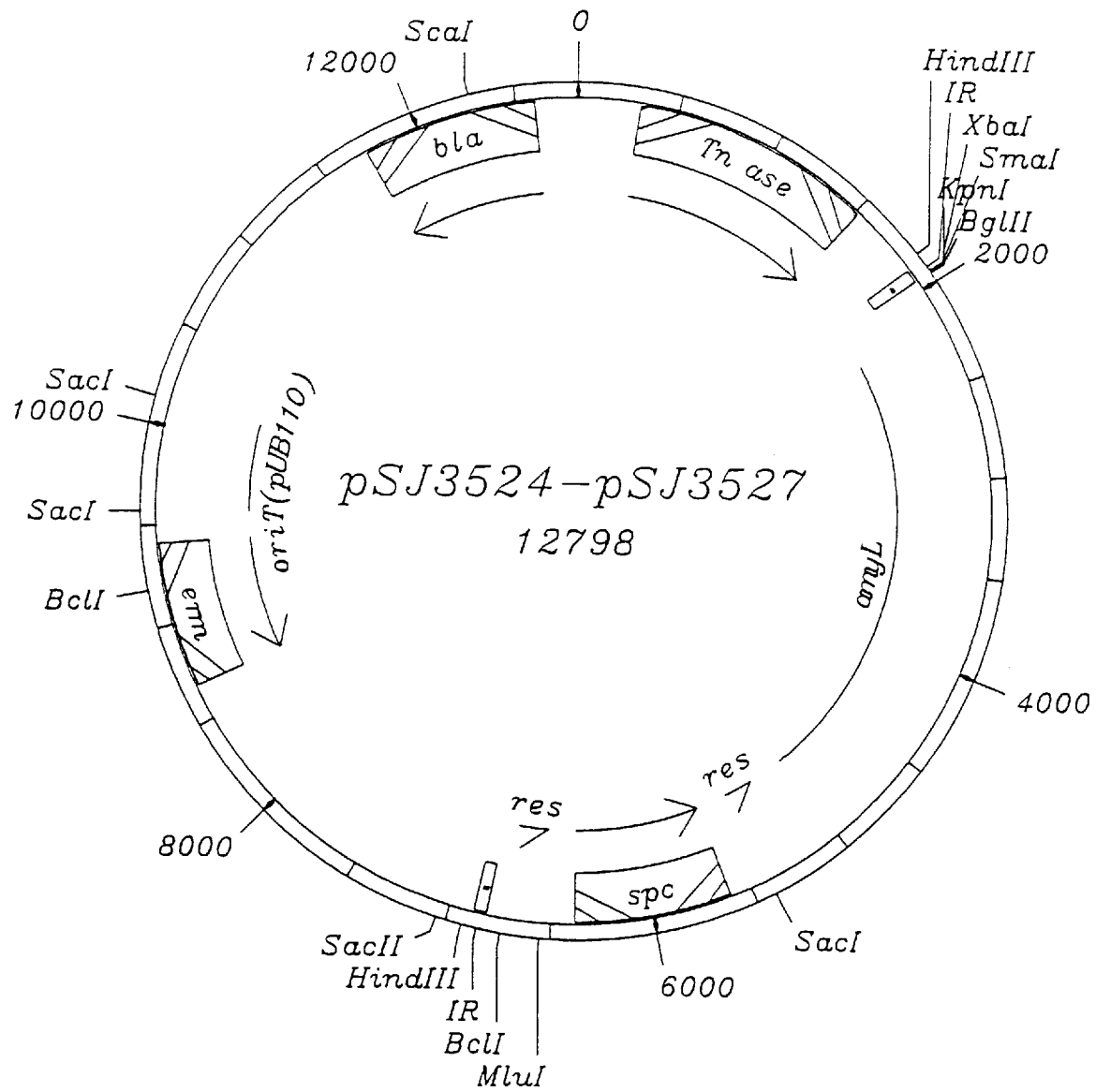

FIG. 1 is a restriction map of plasmid pMOL553;

FIG. 2 is a restriction map of plasmid pSJ3282;

FIG. 3 is a restriction map of plasmid pWT;

FIG. 4 is a restriction map of plasmid pMAP29;

FIG. 5 is a restriction map of plasmid pSJ3157;

FIG. 6 is a restriction map of plasmid pSJ2739;

FIG. 7 is a restriction map of plasmids pSJ3279–pSJ3281;

FIG. 8 is a schematic representation of the oligonucleotide primers and amplified DNA fragments used for the construction of the res-cat-res-IR segment eventually incorporated into plasmids pSJ3389–pSJ3390;

FIG. 9 is a restriction map of plasmids pSJ3372–pSJ3376;

FIG. 10 is a restriction map of plasmids pSJ3389–pSJ3390;

FIG. 11A shows the result of a Mancini immunodiffusion assay for Savinase;

FIG. 11B shows the result of a Mancini immunodiffusion assay for Savinase;

FIG. 12A is a Southern blot, using DNA from the strains indicated;

FIG. 12B is a Southern blot, using DNA from the strains as in FIG. 12A;

FIG. 13 is a restriction map of plasmid pSJ3216;

FIG. 14 is a restriction map of plasmid pSJ3318;

FIG. 15 is a restriction map of plasmids pSJ3328–pSJ3329;

FIG. 16 is a restriction map of plasmids pSJ3326–pSJ3327;

FIG. 17 is a restriction map of plasmids pSJ3341–pSJ3342;

FIG. 18 is a restriction map of plasmids pSJ3358–pSJ3359;

FIG. 19 is a restriction map of plasmids pSJ3354–pSJ3355;

FIG. 20 is a restriction map of plasmids pSJ3444–pSJ3445;

FIG. 21 is a restriction map of plasmid pSJ3475;

FIG. 22 is a restriction map of plasmid pSJ3476;

FIG. 23 is a restriction map of plasmids pSJ3316–pSJ3317;

FIG. 24 is a restriction map of plasmids pSJ3339–pSJ3340;

FIG. 25 is a restriction map of plasmids pSJ3356–pSJ3357;

FIG. 26 is a restriction map of plasmid pSJ3385;

FIG. 27 is a restriction map of plasmids pSJ3459–pSJ3460;

FIG. 28 is a restriction map of plasmids pSJ3586–pSJ3587;

FIG. 29 is a restriction map of plasmids pSJ3524–psJ3527.

The invention is further illustrated in the following examples which are not in any way intended to limit the scope of the invention as claimed.

MATERIALS AND METHODS

In vitro DNA work, transformation of bacterial strains etc. were performed using standard methods of molecular biology (Maniatis, T., Fritsch, E. F., Sambrook, J. "Molecular Cloning.

A laboratory manual". Cold Spring Harbor Laboratories, 1982; Ausubel, F. M., et al. (eds.) "Current Protocols in Molecular Biology". John Wiley and Sons, 1995; Harwood, C. R., and Cutting, S. M. (eds.) "Molecular Biological Methods for Bacillus". John Wiley and Sons, 1990). Enzymes for DNA manipulations were used according to the specifications of the suppliers.

Media used (TY, BPX and LB agar) have been described in EP 0 506 780. LBPSG agar is LB agar supplemented with phosphate (0.01M $K_3PO_4$), glucose (0.4%), and starch (0.5%)

EXAMPLE 1

Construction of a Transposon Delivery Vector for Transposition of a SAVINASE® Gene Transposon donor plasmid pHV1248 (Petit, M.-A., Bruand, C., Janniere, L., Ehrlich, S. D. (1990) Tn10-derived transposons active in *Bacillus subtilis*. J. Bacteriol., 172, 6736–6740) was used as starting material. This plasmid contain the pE194 replicon which is thermosensitive for replication, and carry a transposase gene from Tn10 modified to be expressed in *Bacillus subtilis*, and sufficient sequences from the IS10 elements of Tn10 flanking a chloramphenicol resistance gene (mini-Tn10) to allow transposition of mini-Tn10 into the *Bacillus subtilis* chromosome. pHV1248 was introduced into *E. coli* SJ6 (Diderichsen et al., 1990, J. Bacteriol. 172, 4315–4321), selecting ampicillin resistance (100 µg/ml), to give SJ1609. Strain SJ1609 was deposited with DSM as DSM10445, as a patent deposit in accordance with the Budapest treaty, on Dec. 22, 1995.

SAVINASE ® is the extracellular, alkaline protease from *Bacillus lentus*. A vector for the delivery of this gene by transposition is pMOL553. This plasmid was constructed in two steps.

Step 1.

SOE PCR (Horton, R. M., Hunt, H. D., Ho, S. N., Pullen, J. K., Pease, L. R. (1989) Engineering hybrid genes without the use of restriction enzymes: gene splicing by overlap extension. Gene, 77, 61–68) was used to insert a BamHI site upstream of the cat gene in pHV1248. Two seperate PCR reactions were performed using pHV1248 as template. In the first PCR reaction was used primer 1 (LWN5037): CCCACTGGATCCAATTTTCGTTTGTTG (SEQ ID NO: 3) and primer 2 (LWN5038: GCAAATTGATCCAA-GAGAACCAAC (SEQ ID NO: 4). The underlined bases in primer 1 show the position of the BamHI site. The second PCR reaction was based on primer 3 (LWN5036): CAA-CAAACGAAAATTGGATCCAGTGGG (SEQ ID NO: 5) and primer 4 (LWN5039): GCACATCATCATCATAAGC (SEQ ID NO: 6). Both PCR reactions were performed by standard procedures using temperatures of 96° C. at denaturation, 55° C. at annealing and 72° C. at the extension step. A total of 20 cycles were performed. Both fragments were purified from an agarose gel and 500 ng of each were used for a second 5 cycle PCR reaction: 96° C. for 2 min., 50° C. for 5 min and 72° C. for 1 min. Primer 2 and primer 4 (100 pmol) were added at 96° C. and a third 25 cycle PCR reaction was initiated: 96° C. for 30 sec., 55° C. for 30 sec. and 72° C. for 90 sec. The final PCR fragment of 1330 bp was digested with HindIII, ligated to HindIII digested pHV1248, and the ligation mixture transformed into *E. coli* SJ2 (Diderichsen et al., 1990, J. Bacteriol. 172, 4315–4321). One transformant kept, MOL612, contained plasmid pMOL610. The position of the BamHI site in pMOL610 was verified by restriction digest.

Step 2

In this step the entire SAVINASE® gene was cloned into the BamHI site of pMOL610. The SAVINASE® e gene and a promoter region was amplified from plasmid pSX222 (WO 92/11357) by PCR using primers with BamHI restriction sites (underlined), primer 5 (LWN5136): CCGGCGGATC-CAGAGGGTGATCG (SEQ ID NO: 7) and primer 6 (LWN2043): GGGGTACTAGTAACCCGGGCCCGGCG-TAGAGGATCC ATACACAAA (SEQ ID NO: 8). This SAVINASE® gene encodes the wild type SAVINASE® enzyme, but the DNA sequence is modified to contain a number of restriction enzyme sites within the SAVINASE® coding sequence. The PCR reaction was performed as follows: 96° C. for 30 sec., 55° C. for 30 sec., and 72° C. for 120 sec. After 20 cycles the PCR fragment was BamHI digested, purified and cloned into the BamHI site of pMOL610. The ligation mixture was transformed into *E. coli* SJ2, and one transformant kept as MOL553 (SJ2/pMOL553). The cloning was verified by restriction digests and a distinct protease phenotype in *B. subtilis* (e.g. in strain DN1885 (Diderichsen et al., 1990, J. Bacteriol. 172, 4315–4321), or protease-deficient derivatives of this strain).

The transposon delivery vector encoding SAVINASE® thus constructed is pMOL553. The full sequence of this plasmid is given as SEQUENCE ID no. 1, and a restriction map in FIG. 1.

EXAMPLE 2

Transposition of a SAVINASE® gene into the *B. lentus* chromosome, using selection for chloramphenicol resistance The transposon delivery plasmid pMOL553 was used to insert extra protease genes randomly in the chromosome of *B. lentus*.

A mutant of the alkalophile *Bacillus lentus* strain C360 (CA 954807) was transformed with the plasmid pMOL553 by protoplast transformation according to a method almost identical to the HCP-1,5 overlayer procedure described by Akamatsu (Akamatsu, T. et al. (1984), Agric. Biol. Chem. 48(3), 651–655). The only major difference was that pH of the HCP-1,5 media and agar was changed to pH 9 to allow the alkalophilic bacilli to regenerate under more suitable conditions. The regeneration plates containing either 10 $\mu$g/ml chloramphenicol or 5 $\mu$g/ml erythromycin were incubated from 5 to 10 days at 30° C.

After reisolating the transformants on LB9 plates (LB medium containing 0.05M NaHCO$_3$ buffer pH 9.0) with 2 $\mu$g/ml erythromycin, the mini Tn10 transposon carrying the protease gene as well as the cat gene was allowed to transpose according to the method described by Petit et al., 1990. After overnight incubation in liquid medium at 46° C., cultures were plated on LB9+6 $\mu$g/ml chloramphenicol at 46° C. and colonies screened for erythromycin sensitivity. Eleven erythromycin sensitive, chloramphenicol resistant colonies were selected. A Southern analysis of the chromosomal DNA isolated from these 11 colonies revealed that each contained a mini transposon inserted in the chromosome in one copy. 10 strains contained identical insertions, whereas one contained an insertion in a different position. The 10 identical strains most likely represent siblings from an early transposition event. None of the transposons had inserted into the gene coding for the native protease situated in the *B. lentus* chromosome.

EXAMPLE 3
Transposition of a SAVINASE® Gene into the *Bacillus lentus* Chromosome, Without Selection for Chloramphenicol Resistance In an experiment almost identical to that of example 2, a *B. lentus* strain with a chromosomal deletion in the alkaline protease gene was transformed with pMOL553 by the above mentioned protoplast procedure. Throughout this experiment the selection pressure was only for erythromycin resistance, conferred by the vector part of pMOL553. The idea was to isolate cells that had gained an active protease gene by transposition of the protease-carrying mini transposon into the chromosome, by screening for the ability to degrade skimmed milk on an LB(9) agar plate. The protoplast transformation and reisolation steps were performed with erythromycin selection only. The integration period at 30° C. allowing the transposon to integrate was one day in LB(9) medium with 2 $\mu$g/ml erythromycin. After one day in LB(9) medium without selection pressure at 46° C. the cells were spread on LB(9) plates with 1% skimmed milk, but no antibiotics. Among 600 colonies 59 were protease positive. These 59 colonies were subsequently analyzed with respect to their antibiotic resistance phenotypes. 19 colonies were resistant to both erythromycin and chloramphenicol indicating that they still contained pMOL553, while 40 colonies were resistant to chloramphenicol only, indicating that they had arisen through transposition of the cat and SAVINASE® genes onto the chromosome.

Two of the chloramphenicol resistant and erythromycin sensitive colonies were analyzed by Southern hybridization. Both cells contained two copies of the protease carrying mini transposon situated in the chromosome at locations different from the location of the (in this case partly deleted) native protease gene. All four mini transposon integrations were at different positions in the *B. lentus* chromosome.

This example thus illustrates the construction of a strain containing multiple, transposed copies of a sequence of interest, encoding a translocated polypeptide, and illustrates the isolation of strains containing transposon insertions, without the use of a selectable marker in the strain isolation.

EXAMPLE 4
Construction of a Donor Strain for Conjugative Transfer of Plasmids Containing oriT from pUB110

Plasmids pLS20 and pBC16 can be transferred by conjugation from *B. subtilis* strain PSL1 UM13 into various Bacillus recipient strains (Koehler, T. M. and Thorne, C. B. (1987). *Bacillus subtilis* (natto) plasmid pLS20 mediates interspecies plasmid transfer. J. Bacteriol., 169, 5271–5278).

DN1280 is a derivative of *B. subtilis* 168, containing a deletion in the dal gene (Diderichsen, B. (1986). A genetic system for stabilization of cloned genes in *Bacillus subtilis*, p35–46. In A. T. Ganesan and J. A. Hoch (eds.),Bacillus molecular genetics and biotechnology applications. Academic Press, Inc., New York). DN1280 was rendered competent and transformed with plasmid pHV1248, selecting for erythromycin resistance (5 $\mu$g/ml) at 30° C. The resulting strain was used as recipient in conjugation with PSL1 UM13. Both strains, taken from plates incubated overnight, were mixed on an LBPSG plate (an LB plate supplemented with phosphate (0.01M K$_3$PO$_4$), glucose (0.4%), and starch (0.5%)) with D-alanine (100 $\mu$g/ml), and incubated for 5 hours at 30° C. The plate was then replicated onto an LBPSG plate as above, but in addition containing erythromycin (5 $\mu$g/ml) and tetracycline (5 $\mu$g/ml). Single colonies appearing on the replica plate was assayed for their ability to transfer pBC16 into *B. subtilis* DN1885. Conjugation was performed by mixing of the strains on LBPSG plates as above and incubation for 5 hours at 30° C. Replication was to LBPSG plates with tetracycline (5 $\mu$g/ml), but without D-alanine.

The omission of D-alanine effectively counterselects the dal$^-$ donor strain. A few of the colonies assayed were able to transfer the Tet$^R$ marker into DN1885. This indicates that these colonies all harbour pLS20 in addition to pBC16. One such colony was propagated at 50° C. in liquid TY medium containing tetracycline (5 $\mu$g/ml) and D-alanine (100 $\mu$g/ml), subsequently plated on LB containing tetracycline (5 $\mu$g/ml) and D-alanine (100 $\mu$g/ml), and replica plated onto LB containing D-alanine (100 $\mu$g/ml) and erythromycin (5 $\mu$g/ml) or chloramphenicol (6 $\mu$g/ml), respectively. An tetracycline resistant, erythromycin and chloramphenicol sensitive isolate was kept as PP289-5. This strain, which is dal$^-$ and contains pLS20 and pBC16, can serve as a conjugation donor strain that allows the transfer of plasmids containing the pUB110 oriT into various recipient strains.

EXAMPLE 5
Construction of a Mobilizable Transposon Delivery Vector for Transposition of a SAVINASE® Gene Mobilization of plasmid pUB110 by pLS20 or its derivatives has been described and analyzed in some details (Koehler, T. M. and Thorne, C. B. (1987). *Bacillus subtilis* (natto) plasmid pLS20 mediates interspecies plasmid transfer. J. Bacteriol., 169, 5271–5278; Selinger, L. B., McGregor, N. F., Khachatourians, G. G. and Hynes, M. F. (1990). Mobilization of closely related plasmids pUB110 and pBC16 by Bacillus plasmid pXO503 requires trans-acting open reading frame β. J. Bacteriol., 172, 3290–3297). In this invention elements from these plasmids were used to mobilize transposon delivery vectors.

Mobilization of pUB110 is dependent on a cis acting region (oriT) located 5' to orfβ (Selinger et al.,1990). A 555 bp segment from pUB110, extending from pos. 1020 to pos. 1575 in the pUB110 sequence (McKenzie, T., Hoshino, T., Tanaka, T., Sueoka, N. (1986) The nucleotide sequence of pUB110: some salient features in relation to replication and its regulation. Plasmid 15, 93–103), was PCR amplified using primers LWN5232 and LWN5233.

LWN5232:
5'-GTCGGAGCTCATTATTAATCTGTTCAGCAATCGGGC-3'(SEQ ID NO:9)

LWN5233:
5'-GTCGGAGCTCTGCCTTTTAGTCCAGCTGATTTCAC-3'(SEQ ID NO:10)

The amplified fragment was digested with SacI and initially cloned into the SacI site of an E. coli plasmid (a pUC19 derivative). The fragment was subsequently excised again using SacI, and cloned into the unique SacI site in the previously described plasmid pMOL553. The ligation mixture was transformed into E. coli SJ2 selecting for ampicillin resistance (100 μg/ml).

Plasmids were prepared from the pooled transformants, and the plasmid mixture transformed into PP289-5, selecting resistance to tetracycline (5 μg/ml), chloramphenicol (6 μg/ml) and erythromycin (5 μg/ml) on LBPSG plates containing D-alanine (100 μg/ml). The transformants were again pooled, and the pool used to transfer the oriT-derivative of pMOL553 into DN1885 by conjugation, using the method described above in EXAMPLE 4. Finally, the identity of the plasmids in the transconjugants was verified by restriction mapping, and a strain containing a correct plasmid was kept, as SJ3282 (DN1885/pSJ3282 (=pMOL553-oriT; FIG. 2)).

EXAMPLE 6
Construction of a Mobilizable Plasmid Expression the pAMβ1 Resolvase

Plasmids pWT and pMAP29 were used as starting material for the following experiments. pWT is a high copy number PAMβ1 derivative with the restriction map given in FIG. 3. It was transformed into B. subtilis DN1885, and a transformant kept as strain SJ3008. This strain was deposited with the DSM as a patent deposit in accordance with the Budapest treaty, as DSM10444 on Dec. 22, 1995. pMAP29 contains two directly repeated resolution sites (res) flanking a spectinomycin resistance determinant, and allows insertion of the res/spc/res structure in the amy locus of B. subtilis. It has the map shown in FIG. 4. It is kept in an E. coli strain as SJ3007. This strain was deposited with the DSM as a patent deposit in accordance with the Budapest treaty, as DSM10446 on Dec. 22, 1995.

pMAP29 was digested with ScaI, and transformed into competent DN1885 selecting spectinomycin resistance (60 μg/ml). One such transformant was kept as SJ3109. SJ3109 was rendered competent, and maintained its spectinomycin resistance as competent cells. pWT, prepared from SJ3008, was transformed into SJ3109 selecting erythromycin resistance (5 μg/ml) at 30° C. Of 24 transformant colonies tested, two were spectinomycin sensitive. 5 spectinomycin resistant transformants were propagated in TY medium with erythromycin (2 μg/ml) for 2 days at 30° C. Replica plating from these cultures revealed only spectinomycin sensitive cells in three, but still spectinomycin resistant cells in the other two. Plasmid pWT was easily cured from the cells by restreaking two times at 50° C.

Thus, resolvase as expressed from pWT easily excises the spectinomycin resistance gene from the chromosome of SJ3109.

The sequence of the pAMβ1 resolvase gene is known, as the resolvase is encoded by ORF H as published by Swinfield et al. (Swinfield, T.-J., Janniere, L., Ehrlich, S. D., Minton, N. P. (1991). Characterization of a region of the Enterococcus faecalis plasmid pAMβ1 which enhances the segregational stability of pAMβ1-derived cloning vectors in Bacillus subtilis. Plasmid 26, 209–221).

The gene was amplified by a PCR reaction, using as template pWT and the following primers:

```
                      BamHI    PstI    <  pos.   5102-5129           >
LWN7839: 5'-GACGGGATCCCTGCAGTATCCAATTTATTTTTTCTTAACAAGG-3'(SEQ ID NO:11)

EcoRI    HindIII <  pos.   5820-5797           >
LWN7840: 5'-GACGGAATTCAAAGCTTAAAGCACTTGCATAGGCTAATGCC-3' (SEQ ID NO:12)
``` where the sequence numbering is taken from the above reference.

The amplified DNA fragment was digested with restriction enzymes PstI and HindIII, and subsequently ligated to the 4.1 kb PstI-HindIII fragment isolated from pDN1981 (Jorgensen, P. L., Hansen, C. K., Poulsen, G. B., Diderichsen, B. (1990). In vivo genetic engineering: homologous recombination as a tool for plasmid construction. Gene 96, 37–41) and transformed into B. subtilis DN1885 selecting kanamycin resistance (10 μg/ml). Two transformants were kept, SJ3157 containing pSJ3157 (FIG. 5), and SJ3158 containing pSJ3158 (the PstI site in pSJ3158 was destroyed in the cloning, otherwise the plasmids are identical). pSJ3157 and pSJ3158 are examples of the plasmid pAmyLres, containing the resolvase gene expressed from the B. licheniformis amyL promoter, on a pUB110 derived vector conferring kanamycin resistance.

These two plasmids and pDN1981 as a control were transformed into SJ3109. Kanamycin and spectinomycin resistant colonies (5 with each plasmid) were incubated in TY with kanamycin for 3 days at 30° C., then spread for replica plating: All resulting colonies containing pSJ3157 or pSJ3158 were spectinomycin sensitive, whereas colonies containing pDN1981 were spectinomycin resistant.

Resolvase expressed from the Termamyl (amyL) promoter thus works efficiently in promoting recombination between res sites in the Bacillus chromosome.

In a subsequent step, the amyL promoter and resolvase gene was transferred onto a mobilizable, temperature sensitive cloning vector, pSJ2739 (FIG. 6). This vector contains the replication functions and erythromycin resistance gene of pE194 (Horinouchi, S., and Weisblum, B. (1982). Nucleotide sequence and functional map of pE194, a plasmid that specifies inducible resistance to macrolide, lincosamide, and streptogramin type B antibiotics. J. Bacteriol., 150, 804–814), oriT of pUB110, part of the kanamycin resistance gene of pUB110, and a segment of the alpha-amylase gene (amyL) from *Bacillus licheniformis*. Its full sequence is given as SEQUENCE ID no. 2.

Genes expressed from the amyL promoter on e.g. pDN1981 can conveniently be transferred onto pSJ2739 using BglII and e.g. HindIII. This cloning restores the kanamycin resistance gene.

pSJ3157 and pSJ3158, respectively, were digested with HindIII and BglII, the 2.3 kb fragments ligated to the 5.4 kb BglII-HindIII fragment of pSJ2739, and the mixture transformed into competent DN1885 selecting kanamycin (10 µg/ml) and erythromycin (5 µg/ml) resistance at 30° C. Three transformants kept were SJ3279 (pSJ3279; from pSJ3157)
SJ3280 (pSJ3280; from pSJ3157) and
SJ3281 (pSJ3281; from pSJ3158).

Their restriction map is shown in FIG. 7.

These plasmids are examples of the plasmid pAmyLres (ts).

Functionality of these plasmids were assayed by transformation of strain SJ3109; Propagation of SJ3109 containing each plasmid resulted in the appearance of spectinomycin-sensitive cells, and the plasmids were subsequently easily cured from the cells by growth without antibiotics at 46° C.

EXAMPLE 7
Construction of a Donor Strain for Conjugative Transfer of the Resolvase Expressing Plasmid The plasmids constructed in EXAMPLE 6 were transformed into competent cells of the conjugation donor strain PP289–5 (dal⁻-, pLS20, pBC16) to allow their easy transfer into other Bacillus strains by conjugation. The following strains were kept:

SJ3308=PP289-5/pSJ3279
SJ3309=PP289-5/pSJ3280
SJ3310=PP289-5/pSJ3281

These strains were able to mobilize the resolvase-expressing plasmid into strain SJ3109, using the procedure for conjugation previously described, where it functioned to excise the spectinomycin resistance gene from the chromosome.

EXAMPLE 8
Insertion of Resolvase Target Sites, res, Around the cat Marker on the Mobilizable Transposon Delivery Vector for Transposition of a SAVINASE® Gene The MluI and SacII sites in pMOL553 (see FIG. 1) are unique. A modified version of the MluI-SacII fragment can therefore be constructed so as to contain res sites on each end of the cat gene, and can subsequently be ligated to MluI+SacII digested pMOL553. The construction can be performed by PCR amplification, using a number of oligonucleotide primers, by the SOE method as outlined in FIG. 8. The res site has been located in the pAMβ1 sequence (Swinfield, T. J., Oultram, J. D., Thompson, D. E., Brehm, J. K., Minton, N. P. (1990) Physical characterization of the replication region of the *Streptococcus faecalis* plasmid pAMβ1, Gene 87, pp. 79–90) to pos. 4841–4951 (Janniere, L., Gruss, A., Ehrlich, S. D. (1993), Plasmids, pp. 625–644 in Sonenshein, A. L., Hoch, J. A., Losick, R. (Eds.) *Bacillus subtilis* and other gram-positive bacteria: Biochemistry, Physiology, and Molecular Genetics. American Society for Microbiology, Washington, D.C.). Accordingly, the PCR primers used for the construction as outlined in FIG. 8 have the sequences given below:

```
LWN7794:
       KpnI      MluI
5'-GACGGGTACCACGCGTTAATCAATAAAAAAACGCTGTGCGGTTAAA-
                          BamHI<-   X17092   pos.4840-4863      -->
   GGGCACGCGTTTTTTTGTGTATGGATCCTTCTATCTTTTATAGGTCATTAG-3' (SEQ ID NO:13)

LWN7790:
   pMOL553  pos.3942-3920      ><   X17092   pos.   4975-4956
5'-TATATATTTTAAAAATATCCCACGGTTCTTCAAATATTTCTCC-3' (SEQ ID NO:14)

LWN7789:
   x17092  POS.4956-4975       ><   pMOL553  pos.3920-3943
5'-GGAGAAATATTTGAAGAACCGTGGGATATTTTTAAAATATATAT-3' (SEQ ID NO:15)

LWN7788:
   x17092  pos.4829-4808       ><   pMOL553  pos.4795-4773
5'-CAAGTGTTCGCTTCGCTCTCACGGAGCTGTAATATAAAAACCTTC-3' (SEQ ID NO:16)

LWN7787:
   pMOL553  pos.4773-4795      ><   X17092   pos.4808-4829
5'-GAAGGTTTTTATATTACAGCTCCGTGAGAGCGAAGCGAACACTTG-3' (SEQ ID NO:17)

LWN7784:
   pMOL553  pos.4819-4796      ><   X17092   pos.4953-4933
5'-CATATGATCAAATGGTTCGGATCTGATTTTCCTCCTCTAATATGC-3' (SEQ ID NO:18)

LWN8197:
   X17092  pos.4933-4953       ><   pMOL553  pos.4796-4819
5'-GCATATTAGAGGAGGAAAATCAGATCCGAACCATTTGATCATATGACAAGATGTG-3' (SEQ ID NO:19)
```

LWN7791:
```
      EcoRI    SacII
5'-GACGGAATTCCCGCGGTAAATAGCAATAAATTGGC-3' (SEQ ID NO:20)
```

LWN7780:
```
      KpnI     MluI
5'-GACGGGTACCACGCGTTAATC-3' (SEQ ID NO:21)
```

PCR fragments A, B, C, and D (FIG. 8) were prepared as follows, using 10 pmole of each primer in a standard PCR reaction (25 cycles) with Taq polymerase.

A: Primers LWN7794 and LWN7790, template pWT (from SJ3008), annealing temperature 49° C. The resulting fragment of 230 bp was purified from an agarose gel.

B: Primers LWN7789 and LWN7788, template pMOL553, annealing temperature 51° C. The resulting fragment of 900 bp was purified from an agarose gel.

C: Primers LWN7787 and LWN7784, template pWT (from SJ3008), annealing temperature 53° C. The resulting fragment of 180 bp was purified from an agarose gel.

D: Primers LWN8197 and LWN7791, template pMOL553, annealing temperature 55° C. The resulting fragment of 275 bp was purified from an agarose gel.

These fragments were assembled in two steps. In a first step, aliquots of purified A and B fragments were mixed and used as template in a PCR reaction with primers LWN7780 and LWN7788, with an annealing temperature of 55° C. The resulting combined fragment (AB) of 1100 bp was purified from an agarose gel. In parallel, aliquots of purified fragments C and D were mixed and used as template in a PCR reaction with primers LWN7787 and LWN7791, with an annealing temperature of 55° C. The resulting combined fragment (CD) of 440 bp was purified from an agarose gel.

In a second step, the two purified combined fragments, AB and CD, were mixed and used as template in a PCR reaction with primers LWN7780 and LWN7791, with an annealing temperature of 55° C. The resulting combined fragment (ABCD) of 1500 bp was purified from an agarose gel.

The purified fragment (ABCD) was digested with EcoRI and KpnI, ligated to EcoRI+KpnI digested pUC19, and the ligation mixture transformed into *E. coli* SJ2, selecting resistance to ampicillin (100 μg/ml) and chloramphenicol (6 μg/ml). 5 transformants were kept, as SJ3372=SJ2/pSJ3372

SJ3373=SJ2/pSJ3373

SJ3374=SJ2/pSJ3374

SJ3375=SJ2/pSJ3375

SJ3376=SJ2/pSJ3376.

The structure of these plasmids was verified by restriction analysis, and by sequencing of the res and IR parts of the insert using primers LWN8906: 5'-GGTTTTTCGCATGTATTGCG-3' (SEQ ID NO: 37) and LWN8907: 5'-GTTCATTTGATATGCCTCC-3' (SEQ ID NO: 38), on an Applied Biosystems automatic sequencer.

A restriction map of pSJ3372–76 is given in FIG. 9. DNA sequencing revealed, that the res and IR regions on plasmids pSJ3372 and pSJ3376 contained no mutations due to errors in the PCR amplification.

The final transposon donor plasmid was constructed by ligating the 1.5 kb SacII-MluI fragment from either plasmid pSJ3372 or plasmid pSJ3376 to the 9.6 kb SacII-MluI fragment from pSJ3282. The ligation mixtures were transformed into *E. coli* SJ2 by electroporation, and cells plated on either ampicillin (100 μg/ml) plus chloramphenicol (6 μg/ml), or erythromycin (5 μg/ml) plus chloramphenicol (6 μg/ml), at 30° C., and transformants restreaked on all three antibiotics. Two transformants were kept:

SJ3389=SJ2/pSJ3389 (from pSJ3376) and

SJ3390=SJ2/pSJ3390 (from pSJ3372).

The plasmid structures were verified by PCR amplifications and restriction analysis. The restriction map of pSJ3389-90 is given in FIG. 10.

EXAMPLE 9
Construction of a Donor Strain for Conjugative Transfer of the Transposon Delivery Vector of Example 8

Competent cells of *B. subtilis* strain PP289-5 were transformed with pSJ3389, selecting resistance to tetracycline (5 μg/ml), erythromycin (5 μg/ml), and chloramphenicol (6 μg/ml) on LBPSG plates with D-alanine (100 μg/ml).

Transformants kept are

SJ3503=PP289-5/pSJ3389 and

SJ3504=PP289-5/pSJ3389

EXAMPLE 10
Introduction of the Transposon Delivery Vector of Example 8 into *B. subtilis*, and Isolation of Strains in which Transposition has Occured

*B. subtilis* DN1885 competent cells were transformed with plasmids pSJ3389 or pSJ3390, selecting erythromycin (5 μg/ml) and chloramphenicol (6 μg/ml) resistance at 30° C. Four transformants containing each plasmid were kept, all exhibiting a distinct protease-positive phenotype on plates with skimmed milk:

SJ3431=DN1885/pSJ3389

SJ3432=DN1885/pSJ3389

SJ3433=DN1885/pSJ3389

SJ3434=DN1885/pSJ3389

SJ3435=DN1885/pSJ3390

SJ3436=DN1885/pSJ3390

SJ3437=DN1885/pSJ3390

SJ3438=DN1885/pSJ3390

These strains were inoculated in 10 ml TY medium with 3 μg/ml chloramphenicol, and shaken at 30° C. overnight. 100 μl was transferred to new 10 ml TY medium tubes with 3 μg/ml chloramphenicol, and shaken at 50° C. for 4 hours. A dilution series from each tube was then plated on LBPSG with 6 μg/ml chloramphenicol and incubated at 50° C. for two days. These plates were then replica plated onto i) plates with erythromycin (5 μg/ml) and chloramphenicol (6 μg/ml), and ii) plates with chloramphenicol (6 μg/ml) only, and the plates incubated at 37° C. overnight.

Among the chloramphenicol resistant colonies, only 10–20% had retained the erythromycin resistance, indicating the continued presence of the transposon donor plasmid in these cells. One chloramphenicol resistant, erythromycin sensitive isolate from each of the 8 strains was kept:

SJ3465 from SJ3431, SJ3466 from SJ3432, SJ3467 from SJ3433, SJ3468 from SJ3434, SJ3469 from SJ3435, SJ3470 from SJ3436, SJ3471 from SJ3437, and SJ3472 from SJ3438.

SJ3470 was distinctly red in liquid TY medium.

A control PCR reaction, using primers LWN5136: 5'-CCGGCGGATCCAAGGGGTGATCG-3' (SEQ ID NO: 7) and LWN5067: 5'-CCAGAACCTGTCAATCCACG-3' (SEQ ID NO: 22), with annealing temperature 55° C., was performed on these strains. A fragment of 900 basepairs, as expected for amplification from the SAVINASE® construct on the transposable DNA, was obtained, confirming the presence of the SAVINASE® gene in the genome of these strains.

EXAMPLE 11
Resolvase Mediated Marker Deletion from the Strains of Example 10

Strain SJ3309, described in EXAMPLE 7, is able to donate a resolvase-expressing plasmid to Bacillus recipient strains by conjugation.

SJ3309 was streaked on LBPSG plates with D-alanine (100 μg/ml), tetracycline (5 μg/ml) and erythromycin (5 μg/ml), and incubated at 30° C. overnight.

Each of the strains SJ3465 to SJ3472 were streaked on LBPSG plates with chloramphenicol (6 μg/ml) and incubated at 37° C. overnight.

On separate LBPSG plates containing D-alanine (100 μg/ml), each of the strains SJ3465 to SJ3472 were mixed with strain SJ3309, and the plates incubated at 30° C. for 5 hours. Cells were then resuspended in TY medium and plated on LBPSG plates with erythromycin (5 μg/ml) and chloramphenicol (6 μg/ml), or erythromycin only. These plates were incubated at 30° C. for three days.

Transconjugants where the recipient strains were SJ3465 to SJ3468, showed good growth on erythromycin only, but poor growth on both chloramphenicol and erythromycin.

Transconjugants where the recipient strains were SJ3469 to SJ3472, showed good growth on both types of plates. Upon reisolation, transconjugants derived from SJ3465 to SJ3468 could only grow on erythromycin, indicating loss of the chloramphenicol resistance gene. Transconjugants derived from SJ3469 to SJ3472 could grow on both types of plates.

To remove the resolvase expressing plasmid from the cells, transconjugants from SJ3465 to SJ3468 were inoculated in TY medium and incubated at 50° C. with shaking for 5 hours. Aliquots from these cultures were streaked on LBPSG plates, which were incubated at 50° C. overnight, and subsequently replicated to LBPSG, LBPSG with chloramphenicol (10 μg/ml), and LBPSG with erythromycin (5 μg/ml). These plates were incubated at 37° C. overnight. One erythromycin sensitive, chloramphenicol sensitive isolate from each culture was kept:

SJ3461 derived from SJ3465
SJ3462 derived from SJ3466
SJ3463 derived from SJ3467
SJ3464 derived from SJ3468.

Transconjugants from SJ3469 to SJ3472, having retained their chloramphenicol resistance, were inoculated in TY medium with 2 μg/ml erythromycin, and shaken at 30° C. for 3 days. Aliquots were plated on LBPSG at 30° C., and plates replicated to LBPSG, LBPSG with chloramphenicol (10 μg/ml), and LBPSG with erythromycin (5 μg/ml). All colonies were erythromycin resistant, but 90% of colonies from SJ3470, and all from the three others, were chloramphenicol sensitive, again indicating loss of the chloramphenicol resistance gene.

The resolvase expressing plasmid was removed from the strains as above. The following strains were kept:

SJ3489 derived from SJ3469
SJ3490 derived from SJ3470
SJ3491 derived from SJ3472.

The presence of the SAVINASE® gene was verified by PCR using primers LWN5136 and LWN5067 as described in example 10.

EXAMPLE 12
Reintroduction of the Transposon Delivery Vector of Example 8 into the Marker Free Strains of Example 11, and Isolation of Strains in which Transposition has Occured pSJ3389 was transferred from SJ3503 and SJ3504 into strain SJ3461 by conjugation on plates, as previously described. After incubation of the mixed strains on D-alanine plates, cells were resuspended and plated on LBPSG containing chloramphenicol (6 μg/ml) and erythromycin (5 μg/ml) at 30° C. Colonies were checked for tetracycline resistance, indicating presence of pBC16. 3 among 30 checked were tetracycline sensitive. These were kept as SJ3486=SJ3461/pSJ3389, SJ3487=SJ3461/pSJ3389, and SJ3488=SJ3461/pSJ3389.

Strains, in which a new copy of the SAVINASE® gene had been inserted into the genome by transposition, were isolated essentially as previously described, except that BPX was used as the liquid medium.

Strains SJ3486, 3487 and 3488 (*B. subtilis* DN1885 containing one chromosomal SAVINASE® gene copy, plus the transposon donor plasmid), and as a control strain SJ3431 (*B. subtilis* DN1885 containing only the transposon donor plasmid) were inoculated in 10 ml BPX with chloramphenicol (6 μg/ml), and incubated with shaking for 4 days at 30° C. Aliquots (appr. 100 μl) were transferred to new 10 ml BPX tubes with chloramphenicol (6 μg/ml), and incubated with shaking for 4 hours at 50° C. Aliquots from these cultures were then spread on LBPSG containing chloramphenicol (6 μg/ml) at 37° C., and the resulting colonies checked for erythromycin resistance by replica plating.

All colonies derived from strain SJ3431 were erythromycin sensitive.

All colonies derived from strains SJ3486 and SJ3488 were erythromycin resistant.

About half the colonies from strain SJ3487 were erythromycin sensitive. 10 of these were kept as SJ3537 to SJ3546.

EXAMPLE 13
Resolvase Mediated Marker Deletion from the Strains of Example 12

Strains SJ3537, 3539, 3541 and 3546 were chosen for further work. The resolvase expressing plasmid was introduced into these strains by conjugation from strain SJ3309, as described in example 11 for the one-copy strains.

All transconjugant colonies, selected on erythromycin plates, were by replica plating found to be chloramphenicol sensitive, except for a few colonies from the SJ3541 recipient. The excision of the chloramphenicol resistance gene, mediated by resolvase, was thus found to be very efficient. About 50% of the colonies were tetracycline sensitive, indicating absence of pBC16 (which is present as a helper in the donor strain). One tetracycline sensitive, chloramphenicol sensitive trans-conjugant colony from each recipient was propagated in TY at 50° C. for 4 hours, then plated on LBPSG at 50° C., and the resulting colonies checked for absence of the resolvase-expressing plasmid by replica 5plating to LBPSG plates with erythromycin (5 μg/ml). All were erythromycin sensitive. One coloni, derived from each recipient strain, was kept:

SJ3565 from SJ3537, SJ3566 from SJ3539, SJ3567 from SJ3541, and SJ3568 from SJ3546.

EXAMPLE 14

Visualisation of SAVINASE® Yields from the Strains of Examples 10–13
Halo formation on plates:

Strains DN1885 (the B. subtilis SAVINASE® negative recipient strain), SJ3465–SJ3472 (1. transposition, $Cam^R$, $Sav^+$), SJ3461 (1. transposition $Cam^S$, $Sav^+$ (from SJ3465)), SJ3537–SJ3546 (2. transposition (in SJ3461), $Cam^R$, $Sav^+$), and SJ3565–SJ3568 (2. transposition, $Cam^S$, $Sav^+$) were streaked on LBPSG plates containing 1% skimmed milk. After overnight incubation at 37° C., differenses in halo formation were observed. DN1885 had hardly any halo, 1. transposition strains had a distinct halo, and 2. transposition strains seemed to have a slightly larger halo than 1. transposition strains. No difference in halo size was observed due to the removal of the cat gene.

Mancini immunodiffusion assay:

Strains were inoculated in 100 ml BPX shake flasks (with addition of 0.5 ml 1M NaOH), and shaken for 4 days at 30° C., 300 rpm.

Supernatants were subjected to a Mancini immunodiffusion assay in an agarose gel containing anti-SAVINASE® antibody.

No precipitation zone was seen with DN1885, in accordance with the absence of the SAVINASE® gene from this strain. Zones of somewhat varying size were seen for the 1. transposition strains (SJ3465–3472). Removal of the cat gene did not significantly affect this zone (SJ3461). Zones of conspicuously larger size were seen from the 2. transposition strains (SJ3537–3546), and removal of the cat gene did not significantly affect these zones (SJ3565–3568). The immunodiffusion plates are reproduced in FIG. 11, A and B.

Conclusion:

These phenotypical tests thus revealed the results of the strain constructions: One copy (at least) of the SAVINASE® gene could be inserted by transposition, giving rise to SAVINASE® production. The chloramphenicol resistance gene on the transposed DNA could be removed using resolvase, and the resulting strain could still produce SAVINASE® at the original level. One (or more) further copies of the SAVINASE® gene could be inserted into the one copy strain, reusing the same transposon donor plasmid as used for insertion of the first copy. This resulted in an increased SAVINASE® yield. The chloramphenicol resistance gene on the transposed DNA could subsequently be removed using resolvase again, and the resulting strains retained their ability to produce increased SAVINASE® yields.

EXAMPLE 15

Southern Analysis of Strains of Examples 10–13

The strains of examples 10–13 were grown overnight in TY medium, and chromosomal DNA extracted by standard procedures (phenol/chloroform extractions). The DNA was digested with EcoRI, which cuts within the SAVINASE® gene part of the transposable DNA, and in addition with enzymes BglI, PstI and SacII, which does not cut within the transposable DNA. Several enzymes were used together in order to obtain DNA fragments of moderate size, that could be well resolved on the gel. Fragments were transferred to IMMOBILON-N (Millipore) membranes after electrophoresis by vacuum blotting, and the membrane probed with biotinylated labeled probes, using the NEBLOT PHOTOTOPE Kit and PHOTOTOPE Detection Kit from New England Biolabs. The same membrane was used with several sets of probes. First, a probe recognizing the upstream half of the transposable DNA was used, i.e. the region between the IR at around pos. 2000 and the EcoRI site at around pos. 3600 in pSJ3389. The probe was made by PCR amplification from pMOL553, using as primers LWN5136 and LWN5067. This probe is expected to recognize one fragment derived from each transposon insertion, and this fragment should not be affected by the subsequent action of the resolvase. This is exactly what is observed from FIG. 12A. Strains SJ3465 to SJ3472 were isolated following the first transposition round, and contain both the cat and the savinase gene. As they resulted from different transposition events, different fragment sizes are observed. Strain SJ3461 was isolated from SJ3465, and contain only the savinase gene. The same hybridizing fragment is observed in this strain (2.0 kb). Strains SJ3537–3546 were isolated following the second transposition round. They contain the same fragment as SJ3461 (2.0 kb), but has acquired an additional hybridizing fragment of 1.8 kb. The same two hybridizing fragments are observed in strains SJ3565–3568, in which the resolvase gene was used to delete the cat gene (DNA from SJ3565 was degraded by nucleases).

The membrane was subsequently stripped for the probe, and rehybridized with two probes. One was the same as before. The other was the PCR fragment containing res-cat-res-IR, called ABCD in example 8. The first probe should recognize the same fragments as before. The new probe should recognize a new fragment, and the size of this fragment should become reduced by the resolvase mediated deletion of the cat gene. This is exactly what is observed from FIG. 12B. The new fragment, of about 3.7 kb in strain SJ3465, is reduced to about 2.7 kb in strain SJ3461. Strains SJ3537–46 contain an additional fragment of 3.3 kb, which is reduced to 2.3 kb in strains SJ3566–68.

Fragments were visible at higher positions on the southern blot—these were due to incomplete digestion of the chromosomal DNA with one or more of the enzymes.

Also, the fragments containing the res-cat-res-IR part of the transposon are actually visible on FIG. 12A. This is caused by the presence of some plasmid pMOL553 in the material used for labelling (The PCR fragment was not gel purified).

EXAMPLE 16

Construction of a Mobilizable Transposon Delivery Vector Containing a res-spc-res Cassette
A) Amplification of the spc resistance gene.

The spectinomycin resistance gene was obtained from plasmid pMAP29 (FIG. 4) on a 1.2 kb SalI-BamHI fragment. This fragment was purified from an agarose gel, and ligated to XhoI+BamHI digested pDN3000 (Diderichsen et al., 1990, J. Bacteriol. 172, 4315–4321), to give plasmid pSJ3216 (FIG. 13). Ligation mixtures were introduced into E. coli SJ2 by electroporation, and selection was for ampicillin (100 μg/ml) and spectinomycin (60 μg/ml) resistance.

The spc gene was PCR amplified from pSJ3216 using primers LWN8524: 5'-GACTGAATTCGGATCCACGCGTATAATAAAGAATAATTATTAATCTGTAG-3' (SEQ ID NO: 23), and LWN8528: 5'-GACTAAGCTTGAGCTCCACTAATATTAATAAACTATCGAAGG-3' (SEQ ID NO: 24); Annealing temperature was 50° C. The fragment was purified on an agarose gel, digested with EcoRI and HindIII, and ligated to EcoRI+HindIII digested pUC19. E. coli SJ2 was transformed by electroporation, selecting ampicillin resistance (100 μg/ml) on plates with IPTG and X-gal. White colonies were reisolated on plates with ampicillin (100 μg/ml) and spectinomycin (60 μg/ml). Strains kept are SJ3318 (SJ2/pSJ3318) and SJ3319 (SJ2/pSJ3319). The map of pSJ3318 is given in FIG. 14.

B) Amplification of the res site with multilinker.

Plasmid pWT (FIG. 3) was used as template in a PCR reaction with primers LWN8529: 5'-GACTGA ATTCCTG-CAGGAGCTCAGTGAGAGCGAAGCGAA CAC-3' (SEQ ID NO: 25) and LWN8531: 5'-GACTAAGCTTTGAT CAAATGGTTGCCGCCGCGTC mGACTCTAGA CCCGGGTACCAGATCTGGATCCTCGGGT-TCTTCAAA TATTTCTCC-3' (SEQ ID NO: 26); annealing temperature was 59° C. The fragment was purified from an agarose gel, digested with EcoRI and HindIII, and ligated to EcoRI+HindIII digested pUC19. E. coli SJ2 was transformed by electroporation, selecting ampicillin resistance (100 μg/ml) on plates with IPTG and X-gal. White colonies were reisolated on similar plates. Plasmids prepared from selected transformants were DNA sequenced using primer LWN7191: 5'-GTTTTCCCAGTCACGAC (SEQ ID NO: 29). Two plasmids with correct sequences of the insert were kept: SJ3328 (SJ2/pSJ3328) and SJ3329 (SJ2/pSJ3329) (FIG. 15).

C) Amplification of the res site.

Plasmid pWT was used as template in a PCR reaction with primers LWN8518: 5'-GACTAAGCTTACGCG TTCGGG TTCTTCAAATATTTCTCC-3' (SEQ ID NO: 27) and LWN8527: 5'-GACTGAATTCTGATCAAATGGTTC AGTGAGAGCGAAGCGAACAC-3' (SEQ ID NO: 28); annealing temperature was 59° C. The fragment was purified from an agarose gel, digested with EcoRI and HindIII, and ligated to EcoRI+HindIII digested pUC19. E. coli SJ2 was transformed by electroporation, selecting ampicillin resistance (100 μg/ml) on plates with IPTG and X-gal. White colonies were reisolated on similar plates. Plasmids prepared from selected transformants were DNA sequenced using primer LWN7191: 5'-GTTTTCCCAGTCACGAC (SEQ ID NO: 29). Two plasmids with correct sequences of the insert were kept: SJ3326 (SJ2/pSJ3326) and SJ3327 (SJ2/pSJ3327) (FIG. 16).

D) Construction of a spc-res fragment.

The 1.1 kb SacI-EcoRI fragment from pSJ3318 was isolated from an agarose gel, and ligated to SacI+EcoRI digested pSJ3328. The ligation mixture was introduced into E. coli SJ6 by electroporation, and transformants selected on plates with ampicillin (100 μg/ml) and spectinomycin (60 μg/ml). Two transformants were kept, SJ3341 (SJ6/pSJ3341) and SJ3342 (SJ6/pSJ3342) (FIG. 17).

E) Construction of a res-spc-res fragment.

The 0.2 kb EcoRI-MluI fragment from pSJ3326 was purified from an agarose gel, and ligated to EcoRI+MluI digested pSJ3341. The ligation mixture was introduced into E. coli SJ6 by electroporation, and transformants selected on plates with ampicillin (100 μg/ml) and spectinomycin (60 μg/ml). Two transformants were kept, SJ3358 (SJ6/pSJ3358) and SJ3359 (SJ6/pSJ3359) (FIG. 18).

F) Cloning of minitransposon (IR-cat-IR) in pUC.

The minitransposon segment (without the transposase gene) was excised from pHV1248 on a 1.2 kb HindIII fragment, which was ligated to HindIII digested pUC19 and used to transform E. coli SJ6 by electroporation to ampicillin (100 μg/ml) and chloramphenicol (10 μg/ml) resistance. Two transformants were kept, SJ3354 (SJ6/pSJ3354) and SJ3355 (SJ6/pSJ3355) (FIG. 19).

G) Insertion of the res-spc-res segment into minitransposon.

The minitransposon contained BsaBI sites in the IR sequences outside the terminal regions essential for transposition. These sites were used for insertion of the res-spc-res segment.

The res-spc-res segment was excised from pSJ3358 on a 1.6 kb HincII-PvuII fragment, purified from an agarose gel, and ligated to the 2.8 kb BsaBI fragment of pSJ3354. The ligation mixture was used to transform, by electroporation, E. coli strain SJ6 to ampicillin (100 μg/ml) and spectinomycin (60 μg/ml) resistance. Two transformants were kept, SJ3444 (SJ6/pSJ3444) and SJ3445 (SJ6/pSJ3445) (FIG. 20).

H) Construction of a re-spc-res containing transposon donor plasmid.

The transposable cassette was excised on a 1.85 kb HindIII fragment from plasmid pSJ3444, which was ligated to the 7.85 kb HindIII fragment from pSJ3282. The ligation mixture was introduced into E. coli SJ6 by electroporation, selecting ampicillin (100 μg/ml) and spectinomycin (60 μg/ml) resistance. Two transformants were kept, with the transposable cassette in different orientations relative to the vector part: SJ3475 (SJ6/pSJ3475; FIG. 21) and SJ3476 (SJ6/pSJ3476; FIG. 22).

The functionality of this transposon donor plasmid was tested. Plasmids pSJ3475 and pSJ3476 were transformed into competent B. subtilis DN1885 selecting for erythromycin (5 μg/ml) and spectinomycin (60 μg/ml) resistance. Four transformants with each plasmid were taken through a transposition round: They were grown overnight in 10 ml TY with spectinomycin (60 μg/ml). 50 μl was transferred to a new culture of 10 ml TY with spectinomycin (60 μg/ml), incubated at 50° C. for 4 hours (resulting in good growth of pSJ3475 transformants, poor growth of pSJ3476 transformants), and plated on LBPSG with spectinomycin (60 μg/ml) at 50° C. 10 single colonies from each plate was streaked on duplicate plates with erythromycin (5 μg/ml) and spectinomycin (60 μg/ml), respectively. Most colonies were erythromycin sensitive, indicating proper transposition of the IR-res-spc-res-IR segment and loss of the donor plasmid. 2 $Spc^R$, $Erm^S$ colonies derived from each of pSJ3475 and pSJ3476 transformants were used as recipients for conjugation with SJ3309 as donor, and transconjugants selected at 30° C. on plates with kanamycin (10 μg/ml) and with or without spectinomycin (60 μg/ml). Good growth was observed on kanamycin plates, but transconjugants from three of the four strains grew poorly on plates with both antibiotics. Spectinomycin sensitive, kanamycin resistant colonies were in all instances obtained by reisolation from the kanamycin plates.

Thus, the modified transposon functions in B. subtilis, and the spectinomycin resistance gene can be subsequently deleted using resolvase.

EXAMPLE 17

Construction of a Mobilizable Transposon Delivery Vector Containing a res-kan-res Cassette A) Amplification of the kan resistance gene.

The kan gene was PCR amplified from pUB110 using primers LWN8516: 5'-GACTGAATTCGGATCCACGCG TGAGTAGTTCAACAAACGGGCC-3' (SEQ ID NO: 30) and LWN8517: 5'-GACTAAGCTTGAGCTCCAACATGA TTAACAATTATTAGAGG-3' (SEQ ID NO: 31); annealing temperature was 59° C. The fragment was purified from an agarose gel, digested with EcoRI and HindIII, and ligated to EcoRI+HindIII digested pUC19. E. coli SJ2 was transformed by electroporation, selecting ampicillin resistance (100 μg/ml) on plates with IPTG and X-gal. White colonies were reisolated on plates with ampicillin (100 μg/ml) and kanamycin (20 μg/ml). Strains kept are SJ3316 (SJ2/pSJ3316) and SJ3317 (SJ2/pSJ3317) (FIG. 23).

B) Construction of a kan-res fragment.

The 1.0 kb SacI-EcoRI fragment from pSJ3316 was isolated from an agarose gel, and ligated to SacI+EcoRI digested pSJ3328. The ligation mixture was introduced into E. coli SJ6 by electroporation, and transformants selected on plates with ampicillin (100 μg/ml) and kanamycin (10 μg/ml). Two transformants were kept, SJ3339 (SJ6/pSJ3339) and SJ3340 (SJ6/pSJ3340) (FIG. 24).

C) Construction of a res-kan-res fragment.

The 0.2 kb EcoRI-MluI fragment from pSJ3326 was purified from an agarose gel, and ligated to EcoRI+MluI digested pSJ3340. The ligation mixture was introduced into *E. coli* SJ6 by electroporation, and transformants selected on plates with ampicillin (100 µg/ml) and kanamycin (10 µg/ml). Two transformants were kept, SJ3356 (SJ6/pSJ3356) and SJ3357 (SJ6/pSJ3357) (FIG. 25).

D) Construction of a res-kan-res containing transposon donor plasmid.

i) Cloning of a transposon IR sequence.

The "downstream" transposon IR sequence was PCR amplified from pMOL553 as template, using primers LWN8760: 5'-GACGGAATTCTCTAGAGTCGACAGATCCGAACCATTTGATCATATGACAAGATGTG-3' (SEQ ID NO: 32) and LWN8761: 5'-GACGGAATTCGCGGCCGCGGTAAATAGCAATAAATTGGCC-3' (SEQ ID NO: 33). The purified fragment was digested with EcoRI, ligated to EcoRI digested pUC19, and introduced by electroporation into *E. coli* SJ2, selecting ampicillin resistance (100 µg/ml) on plates with IPTG and X-gal. About 20 white colonies among 500 was obtained. Plasmid from three was DNA sequenced using as primer LWN4123: 5'-AGCGGATAACAATTTCACACAGGA-3' (SEQ ID NO: 34). Two correct clones were kept as SJ3385 (SJ2/pSJ3385) (FIG. 26) and SJ3386 (SJ2/pSJ3386).

ii) Combination of one IR with res-kan-res sequence.

The IR sequence was excised from pSJ3385 as a 0.3 kb NotI-XbaI fragment, ligated to NotI+XbaI digested, phosphatase treated pSJ3356, and introduced into SJ6 by electroporation, selecting ampicillin (100 µg/ml) and kanamycin (10 µg/ml) resistance. Two transformants were kept as SJ3459 (SJ6/pSJ3459) and SJ3460 (SJ6/pSJ3460) (FIG. 27).

iii) Construction of the final transposon donor plasmid.

In this step, the spc-res segment from donor plasmid pSJ3476 was replaced with the corresponding kan-res segment from pSJ3459. Thus, this 1.15 kb fragment was excised from pSJ3459 using MluI and BamHI, and the purified fragment ligated to the 8.2 kb MluI-BamHI fragment from pSJ3476. The mixture was introduced into *E. coli* SJ6 by electroporation, selecting ampicillin (100 µg/ml) and kanamycin (10 µg/ml) resistance. Two transformants were kept as SJ3586 (SJ6/pSJ3586) and SJ3587 (SJ6/pSJ3587) (FIG. 28).

EXAMPLE 18

Use of the Transposon Delivery Vector of Example 16 for Transposition of an Amylase Gene into the *B. subtilis* Genome The *B. licheniformis* amylase gene (amyL) gene was excised from pDN1981 as a 3.2 kb BglII-BclI fragment, and ligated to BamHI digested pSJ3476. The ligation mixture was transformed into *B. subtilis* DN1885, selecting erythromycin resistance (5 µg/ml) at 30° C. Four amylase positive colonies were reisolated on erythromycin (5 µg/ml) and spectinomycin (60 µg/ml) plates, and kept as SJ3524 (DN1885/pSJ3524), SJ3525 (DN1885/pSJ3525), SJ3526 (DN1885/pSJ3526), and SJ3527 (DN1885/pSJ3527) (FIG. 29).

Strains SJ3524–SJ3527 were tested for transposition. Each was inoculated in LB with erythromycin (5 µg/ml) and spectinomycin (60 µg/ml), incubated overnight at 30° C., and aliquots transferred to LB with spectinomycin (60 µg/ml). These cultures were shaken at 50° C. for 5 hours, then plated on spectinomycin plates (60 µg/ml) and incubated at 30° C. overnight. Plates from SJ3524–3526 were almost overgrown; 8 colonies from each were tested and found erythromycin resistant. The plate from SJ3527 was replica plated, and several erythromycin sensitive, spectinomycin resistant and amylase postivive colonies were found. One was kept as SJ3549.

EXAMPLE 19

Resolvase Mediated Marker Deletion from the Strain of Example 18

The resolvase-expressing plasmid was introduced into SJ3549 by conjugation from SJ3309 as previously described. Transconjugants were selected on kanamycin (10 µg/ml) and spectinomycin (60 µg/ml), and reisolated on kanamycin (10 µg/ml) with or without spectinomycin (60 µg/ml). Growth was poor on plates with both antibiotics, good on kanamycin plates. 10 colonies from kanamycin plates were reisolated on LBPSG, and subsequently replica plated. 8 spectinomycin sensitive, kanamycin resistant kolonies thus isolated were inoculated in TY and incubated at 50° C. overnight, then plated on LBPSG, and these plates replicated after overnight incubation at 37° C. All colonies, except some from culture 1, were kanamycin sensitive. Reisolation confirmed sensitivity to kanamycin (10 µg/ml) and erythromycin (5 µg/ml). Three strains were kept:

SJ3558 (Spc$^S$, Erm$^S$, Kan$^S$, Amy$^+$)
SJ3559 (Spc$^S$, Erm$^S$, Kan$^S$, Amy$^+$)
SJ3560 (Spc$^S$, Erm$^S$, Kan$^S$, Amy$^+$)

The three strains were tetracycline sensitive, indicating absence of pBC16, which is present in the conjugation donor strain.

EXAMPLE 20

Construction of a Donor Strain for Conjugative Transfer of the Transposon Delivery Vector of Example 18

Plasmids pSJ3524 and pSJ3526 were transformed into competent cells of a *B. subtilis* donor strain (dal$^-$, pXO503 (erm$^R$), pBC16 (tet$^R$)) for conjugation, plated on LBPSG with erythromycin (5 µg/ml), tetracycline (5 µg/ml), spectinomycin (60 µg/ml) and D-alanine (100 µg/ml) at 30° C., and one strain containing each plasmid was kept: SJ3547, containing pSJ3524, and SJ3548, containing pSJ3526.

EXAMPLE 21

Reintroduction of the Transposon Delivery Vector of Example 18 into the Marker Free Strains of Example 19, and Isolation of Strains in which Transposition has Occured Plasmid pSJ3524 was transferred into SJ3559, a marker free amyL expressing strain constructed in example 19, by conjugation from SJ3547 as previously described. One tetracycline sensitive transconjugant was kept as SJ3592. This strain was incubated with shaking in TY with spectinomycin (60 µg/ml) at 30° C. overnight, diluted 100 times into a new TY culture with spectinomycin (60 µg/ml), and incubated with shaking for 3 hours at 30° C. It was then diluted 50 times into a new TY culture with spectinomycin (60 µg/ml), incubated with shaking for 3 hours at 50° C., and subsequently plated on LBPSG with spectinomycin (60 µg/ml) at 50° C. Almost all of the resulting colonies were found to be erythromycin sensitive by replica plating. Four were kept, as SJ3626–SJ3629.

In a similar experiment, pSJ3524 was transferred into SJ3560 by conjugation from SJ3547, and two tetracycline sensitive transconjugants kept as SJ3593 and SJ3594. These were incubated with shaking in TY with spectinomycin (60 µg/ml) at 30° C. overnight, diluted 100 times into a new TY culture with spectinomycin (60 µg/ml), incubated with shaking for 6 hours at 50° C., and plated on LBPSG with spectinomycin (60 µg/ml) at 50° C. By replica plating, one spectinomycin resistant and erythromycin sensitive colony was found from SJ3593 (kept as SJ3599), and two such colonies were found from SJ3594 (kept as SJ3600 and SJ3601).

EXAMPLE 22
Resolvase Mediated Marker Deletion from the Strains of Example 21

Strains SJ3626–3629 were used as recipients to recieve the resolvase expressing plasmid by conjugation from strain SJ3309. Transconjugants were selected on LBPSG with kanamycin (10 µg/ml). Colonies from these plates were replicated to kanamycin (10 µg/ml) and spectinomycin (60 µg/ml), and all were found to be spectinomycin sensitive. 4 colonies derived from each recipient strain were transferred three consecutive times through overnight TY cultures at 30° C., plated on LBPSG at 30° C., and replica plated to LBPSG with erythromycin. Sensitive colonies were obtained in each case, and these were subsequently checked for kanamycin resistance. One erythromycin, kanamycin, and spectinomycin sensitive isolate derived from each recipient was kept: SJ3634 (from SJ3626), SJ3635 (from SJ3627), SJ3636 (from SJ3628), and SJ3637 (from SJ3629).

Strains from both 1. and 2. transposition round were inoculated in BPX shake flasks and incubated with shaking for 6 days at 37° C. Alpha-amylase activity was determined using the Phadebas Amylase Test from Kabi Pharmacia. The results are given here in relative, arbitrary units:

|  |  | Units/ml |
|---|---|---|
| B. subtilis DN1885 host strain | | 0.4 |
| (in triplicate) | | 0.26 |
|  | | 0.25 |
| SJ3549 (1. transposition, Spc$^R$) | | 2.45 |
| (in duplicate) | | 2.42 |
| SJ3559 (1. transposition, Spc$^S$) | | 2.4 |
| (in triplicate) | | 2.16 |
|  | | 2.35 |
| SJ3626 | (2. transposition, SPC$^R$) | 3.28 |
| SJ3627 | | 3.6 |
| SJ3628 | | 3.25 |
| SJ3629 | | 3.14 |
| SJ3634 | (2. transposition, SPC$^S$) | 3.21 |
| SJ3635 | | 3.3 |
| SJ3636 | | 3.38 |
| SJ3637 | | 3.1 |

It is evident that a certain production of alpha-amylase is obtained from the 1. transposition strain, this level is unaffected by the subsequent deletion of the spectinomycin resistance gene mediated by resolvase, the level is increased in the 2. transposition strains, and this increased level is maintained upon deletion of the spectinomycin resistance gene mediated by resolvase.

In a similar experiment, strains SJ3599–3601 were used as recipients to recieve the resolvase expressing plasmid by conjugation from strain SJ3309. Transconjugants were selected on LBPSG with kanamycin (10 µg/ml). Colonies from these plates were replicated to kanamycin (10 µg/ml), spectinomycin (60 µg/ml), and tetracycline (5 µg/ml). From each recipient, kanamycin resistant but spectinomycin and tetracycline sensitive colonies could be isolated.

The resolvase expressing plasmid, conferring resistance to both kanamycin and erythromycin, could subsequently be cured from the cells by a few successive transfers of strains in liquid TY medium at 30° C. (without antibiotics), and plasmid free cells isolated by replica plating to plates with erythromycin (5 µg/ml). One such erythromycin sensitive strain isolated from a kanamycin resistant transconjugant of SJ3600 was kept as SJ36–40.

EXAMPLE 23
Introduction of the Transposon Delivery Vector of Example 18 into the Marker Free Strains of Example 13, and Isolation of Strains in which Transposition has Occured In this and the following example, the tools developed in previous examples are combined to create a *Bacillus subtilis* strain, free of antibiotic resistance markers, containing two copies of the SAVINASE® gene and one copy of the *B. licheniformis* amylase gene in its genome.

Strains SJ3565 and SJ3566, each containing two copies of the SAVINASE® gene, were used as recipients in a conjugation with strain SJ3547. Transconjugants were selected on LBPSG with spectinomycin (60 µg/ml) and erythromycin (5 µg/ml). All were amylase-positive and protease-positive. About half were tetracycline sensitive, indicating absence of pBC16. Two tetracycline sensitive colonies derived from each recipient were kept: SJ3595 and SJ3596, from SJ3565, and SJ3597 and SJ3598, from SJ3566.

These strains were incubated with shaking in TY with spectinomycin (60 µg/ml) at 30° C. overnight, diluted 100 times into a new TY culture with spectinomycin (60 µg/ml), incubated with shaking for 6 hours at 50° C., and plated on LBPSG with spectinomycin (60 µg/ml) at 50° C. These plates were subsequently replicated to plates with either spectinomycin (60 µg/ml) or erythromycin (5 µg/ml). No erythromycin sensitive colonies were obtained from SJ3598, whereas about 90% of the colonies from the other three strains were spectinomycin resistant, but erythromycin sensitive. One such colony from each strain was kept: SJ3602 (from SJ3595), SJ3603 (from SJ3596), and SJ3604 (from SJ3597).

EXAMPLE 24
Resolvase Mediated Marker Deletion from the Strains of Example 23

The resolvase expressing plasmid was transferred from strain SJ3309 into each of strains SJ3602–SJ3604 by conjugation as previously described. Transconjugants were selected on LBPSG plates with kanamycin (10 µg/ml) at 30° C., and replica plated to plates with either kanamycin (10 µg/ml), spectinomycin (60 µg/ml), or tetracycline (5 µg/ml). Spectinomycin and tetracycline sensitive colonies were obtained derived from each recipient strain.

The resolvase expressing plasmid, conferring resistance to both kanamycin and erythromycin, could subsequently be cured from the cells by a few successive transfers of strains in liquid TY medium at 30° C. (without antibiotics), and plasmid free cells isolated by replica plating to plates with erythromycin (5 µg/ml). One such erythromycin sensitive strain isolated from a kanamycin resistant transconjugant from each of strains SJ3602–3604 were kept as SJ3641 (from SJ3602), SJ3642 (from SJ3603) and SJ3643 (from SJ3604).

EXAMPLE 25
Construction and use of a Transposon Donor Plasmid Containing the Transposase Gene, Together with a Marker Gene, Flanked by res Sequences.

The purpose of this example is to create and use a transposon donor plasmid, in which transposase and marker together resides between res sequences. This plasmid is then used to isolate strains where transposition has taken place, and the donor plasmid has been lost. The transposed fragment is able to undergo further transpositions, which can be selected for by increased antibiotic resistance. When desired strains are obtained, resistance genes and transposases can be deleted using resolvase, as described in previous examples.

Previously constructed res-marker-res cassettes (examples 16 and 17) contain a unique MluI site, into which transposase can be inserted.

(1) Transposase is PCR amplified from pHV1248, using as primers

BamHI    MluI      <-pHV1248    125-142->
Tnase1: 5'-TGACGGATCCACGCGTGGCGCACTCCCGTTCTGG-3' (SEQ ID NO:35) and BamHI    MluI      <-pHV1248    1550-1531->
Tnase2: 5'-GTACGGATCCACGCGTAAAGGCACCTTTGGTCACGG-3' (SEQ ID NO:36)

The PCR fragment is gel purified, digested with BamHI, and cloned into pUC19 digested with BamHI. Some clones are DNA sequenced, and a correct one used in further work.

(2) A spectinomycin resistance cassette with transposase is constructed by cloning of the MluI fragment from (1), above, into pSJ3444.

(3) A kanamycin resistance cassette with transposase is constructed in two steps: i) The HindIII fragment from pSJ3586 is cloned into pUC19. ii) The MluI fragment from (1) is cloned into i).

The HindIII fragments can then be cloned into pSJ3476 or pSJ3282. The resulting plasmid will have two transposase genes, and clones with these genes in antiparallel orientation can be used as transposon delivery vectors, into which e.g. *B. licheniformis* amylase or SAVINASE® genes may be inserted.

Vector plasmids with only one transposase gene may be prepared as follows:

(4) The NheI-XbaI fragment from pSJ3475, containing the coli-vector part of this plasmid, and the transposase, is deleted. This plasmid is then used as vector for cloning of the HindIII fragments containing the res-marker-transposase-res segments described above.

(5) The ScaI-HindIII fragment from pSJ3282 is replaced by the ScaI-HindIII fragment from pUC18 (this deletes the entire transposon part). Subsequently this new plasmid is used for cloning of HindIII fragments, as above.

---

I claim:

1. A method of constructing a bacterial cell, wherein the cell has integrated two or more copies of a DNA sequence of interest in the genomic DNA of the cell, and wherein the cell is free from a DNA sequence encoding an undesired selectable marker, which method comprises
   a) introducing into a host cell a first vector comprising a DNA construct comprising the structure IR(1)-P-R-M2-R-IR(2) or IR(1)-R-M2-R-P-IR(2), wherein
      IR(1) and IR(2) denote transposase target sequences,
      P is a DNA sequence of interest,
      R is a target sequence for a site-specific recombination enzyme, and
      M2 is a selectable marker gene,
      wherein said structure is in association with a transposase gene T located on either side of and outside said structure, and optionally a selectable marker gene M1;
   b) selecting for a M1$^-$, M2$^+$ cell, wherein said cell contains the structure IR(1)-P-R-M2-R-IR(2) or IR(1)-R-M2-R-P-IR(2) integrated into the cell genome;
   c) introducing a second vector comprising a DNA sequence encoding a site specific recombinase into the cell selected in step b), wherein the structure R-M2 or M2-R is excised from the genome of the cell having said integrated structure IR(1)-R-P-IR(2) or IR(1)-P-R-IR(2),
   d) curing the cells resulting from step c) for the second plasmid, and
   e) repeating steps a)–d) one or more times to produce bacterial cells comprising one or more additional copies of the structure IR(1)-R-P-IR(2) or IR(1)-P-R-IR(2).

2. A method of constructing a bacterial cell, wherein the cell has integrated two or more copies of a DNA sequence of interest in the genomic DNA of the cell, and wherein the cell is free from a DNA sequence encoding an undesired selectable marker, which method comprises
   a) introducing into a host cell a first vector comprising a DNA construct comprising the structure IR(1)-R-M2-T-R-P-IR(2), IR(1)-P-R-M2-T-R-IR(2), IR(1)-R-T-M2-R-P-IR(2) or IR(1)-P-R-T-M2-R-IR(2), wherein
      IR(1) and IR(2) denote transposase target sequences,
      P is a DNA sequence of interest,
      R is a target sequence for a site-specific recombination enzyme,
      M2 is a selectable marker gene, and T a transposase gene T, and optionally in association with a selectable marker gene M1;
   b) selecting for a M1$^-$, M2$^+$ cell, wherein said selected cell contains one of said structures integrated into the cell genome,
   c) selecting for a cell having an increased number of copies of the marker gene M2,
   d) introducing a second vector comprising a DNA sequence encoding a site specific recombinase into the cell selected in step b) wherein the structure R-M2-T, R-T-M2, M2-T-R or T-R-M2 is excised from the genome of the cell whereby cells are obtained having integrated the structure IR(1)-R-P-IR(2) or IR(1)-P-R-IR(2),
   e) curing the cells resulting from step d) for the second plasmid, and
   f) repeating steps a–e one or more times to produce bacterial cells comprising one or more additional copies of the structure IR(1)-R-P-IR(2) or IR(1)-P-R-IR(2).

3. A method for constructing a bacterial cell, wherein the cell has integrated more than two copies of a DNA sequence of interest in the genomic DNA of the cell, and wherein the cell is free from a DNA sequence encoding an undesired selectable marker, which method comprises
   a) introducing into a host cell a first vector comprising a DNA construct comprising the structure IR(1)-P-R'-M2-R"-IR(2) or IR(1)-R'-M2-R"-P-IR(2), wherein
      IR(1) and IR(2) denote transposase target sequences,
      P is a DNA sequence of interest,
      R' and R" are parallel repeat sequences, and
      M2 is a selectable marker gene,
      wherein said structure is in association with a transposase gene T located on either side of and outside said structure, and optionally a selectable marker gene M1;
   b) selecting a M1$^-$, M2$^+$ cell, said cell containing the structure IR(1)-P-R'-M2-R"-IR(2) or IR(1)-R'-M2-R"-P-IR(2);
   c) allowing homologous recombination between the DNA sequences R' and R" to take place so as to excise the selectable marker gene M2, whereby cells are obtained having integrated the structure IR(1)-R'/R"-P-IR(2) or IR(1)-P-R'/R"-IR(2), wherein R'/R" denotes the common recombination sequence; and
   d) repeating steps a–c one or more times to produce bacterial cells comprising one or more additional copies of the DNA structure IR(1)-R'/R"-P-IR(2) or IR(1)-P-R'/R"-IR(2).

4. A method for constructing a bacterial cell, wherein the cell has integrated more than two copies of a DNA sequence of interest in the genomic DNA of the cell, and wherein the cell is free from a DNA sequence encoding an undesired selectable marker, which method comprises
   a) introducing into a host cell a first vector comprising a DNA construct comprising the structure IR(1)-R'-M2-T-R"-P-IR(2), IR(1)-P-R'-M2-T-R"-IR(2), IR(1)-R'-T-M2-R"-P-IR(2) or IR(1)-P-R'-T-M2-R"-IR(2), wherein
      IR(1) and IR(2) denote transposase target sequences,
      P is a DNA sequence of interest,
      R' and R" are parallel repeat sequences,
      M2 is a selectable marker gene, and
      T a transposase gene T, optionally in association with a selectable marker gene M1 into the host cell,
   b) selecting for a M1$^-$, M2$^+$ cell, said cell containing the structure identified in a),
   c) selecting for a cell having an increased number of copies of the selectable marker gene M2,
   d) allowing homologous recombination between the DNA sequences R' and R" to take place so as to excise the selectable marker gene M2 and the transposase gene T, whereby cells are obtained having integrated the structure IR(1)-R'/R"-P-IR(2) or IR(1)-P-R'/R"-IR(2), wherein R'/R" denotes the common recombination sequence, and
   e) repeating steps a–d one or more times to produce bacterial cells comprising one or more additional copies of the DNA structure IR(1)-R'/R"-P-IR(2) or IR(1)-P-R'/R"-IR(2).

5. A bacterial cell, wherein said cell has integrated into the cell genomic DNA at least two copies of a DNA construct comprising the following structure IR(1)-P-IR(2), wherein
   IR(1) and IR(2) denote transposase target sequences, and
   P is a DNA sequence of interest, the structure further comprising a DNA sequence R comprising a target sequence for a site-specific recombination enzyme which is present as a result of excision of a DNA fragment between two R sequences by the action of a resolvase enzyme or by excision the DNA sequence resulting from the homologous recombination between the DNA sequences R'/R".

6. A method of producing a protein of interest encoding by a DNA sequence P, which method comprises cultivating a cell according to claim 5, which cell comprises more than one copy of the DNA sequence P, under conditions suitable for producing the polypeptide, and recovering the polypeptide from the resulting cell broth.

* * * * *